(12) United States Patent
Meksem et al.

(10) Patent No.: US 10,070,614 B2
(45) Date of Patent: Sep. 11, 2018

(54) SOYBEAN RESISTANT TO CYST NEMATODES

(71) Applicants: Khalid Meksem, Carbondale, IL (US); Shiming Liu, Carbondale, IL (US); Pramod Kaitheri Kandoth, Columbia, MO (US); Melissa G. Mitchum, Columbia, MO (US)

(72) Inventors: Khalid Meksem, Carbondale, IL (US); Shiming Liu, Carbondale, IL (US); Pramod Kaitheri Kandoth, Columbia, MO (US); Melissa G. Mitchum, Columbia, MO (US)

(73) Assignees: BOARD OF TRUSTEES OF SOUTHERN ILLINOIS UNIVERSITY, Carbondale, IL (US); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 543 days.

(21) Appl. No.: 14/404,559

(22) PCT Filed: May 30, 2013

(86) PCT No.: PCT/US2013/043392
§ 371 (c)(1),
(2) Date: Nov. 28, 2014

(87) PCT Pub. No.: WO2013/181411
PCT Pub. Date: Dec. 5, 2013

(65) Prior Publication Data
US 2016/0032315 A1 Feb. 4, 2016

Related U.S. Application Data

(60) Provisional application No. 61/653,227, filed on May 30, 2012.

(51) Int. Cl.
| | | |
|---|---|---|
| *A01H 5/10* | (2018.01) |
| *A01H 6/54* | (2018.01) |
| *A01H 1/04* | (2006.01) |
| *C12N 15/82* | (2006.01) |

(52) U.S. Cl.
CPC .............. *A01H 6/542* (2018.05); *A01H 1/04* (2013.01); *A01H 5/10* (2013.01); *C12N 15/8218* (2013.01); *C12N 15/8227* (2013.01); *C12N 15/8285* (2013.01)

(58) Field of Classification Search
None
See application file for complete search history.

(56) References Cited

U.S. PATENT DOCUMENTS

| | | |
|---|---|---|
| 5,378,619 A | 1/1995 | Rogers |
| 6,054,635 A | 4/2000 | Bestwick et al. |
| 2002/0115850 A1 | 8/2002 | Chung et al. |
| 2008/0282431 A1 | 11/2008 | Dasgupta et al. |
| 2008/0313776 A1 | 12/2008 | Li |
| 2011/0083234 A1 | 4/2011 | Nguyen et al. |

FOREIGN PATENT DOCUMENTS

| | | |
|---|---|---|
| JP | 2002-238564 | 8/2002 |
| WO | WO 2000/037662 | 6/2000 |
| WO | WO 2001/051627 | 7/2001 |
| WO | WO 2007/011736 | 1/2007 |

OTHER PUBLICATIONS

Bernard et al 1998 Crop Science 28: 1027.*
Wu et al 2016 Frontiers in Plant Science vol. 7 article 998, 8 pages.*
Meksem et al 2001, Theor. Appl. Genet. 103: 710-717.*
Acedo et al., Nematode Population Attrition and Histopathology of Heterodera glycines-Soybean Associations, Journal of Nematology, 1984, vol. 16, No. 1, pp. 48-57.
Benfey et al., The cauliflower mosaic virus 35S promoter: combinatorial regulation of transcription in plants, Science, 1990, vol. 250, pp. 959-966.
Bernard et al., Registration of 'Williams 82' soybean, Registration of Crop Cultivars, Crop Science, 1988, vol. 28, pp. 1027-1028.
Brown et al., A high-throughput automated technique for counting females of Heterodera glycines using a fluorescence-based imaging system, Journal of Nematology, 2010, vol. 42, No. 3, pp. 201-206.
Cai et al., Positional cloning of a gene for nematode resistance in sugar beet, Science, 1997, vol. 275, pp. 832-834.
Caldwell et al., Inheritance of resistance of soybeans to the cyst nematode, Heterodera Glycines, Agronomy Journal, 1960, pp. 635-636.
Christensen et al., Mitochondrial one-carbon metabolism is adapted to the specific needs of yeast, plants and mammals, BioEssays, 2006, vol. 28, pp. 595-605.
Concibido et al., Review & Interpretation: A decade of QTL mapping for cyst nematode resistance in soybeans, Crop Science, 2004, vol. 44, pp. 1121-1131.
Cooper et al., Tilling to detect induced mutations in soybean, BMC Plant Biology, 2008, vol. 8, No. 9, 10 pages.
De Almeida Engler et al., Nematode-Induced Endoreduplication in Plant Host Cells: Why And How?, MPMI, 2013, vol. 26, No. 1, pp. 17-24.
Dillon et al., RNAi as an experimental and therapeutic tool to study and regulate physiological and disease processes, Annu. Rev. Physiol., 2005, vol. 67, pp. 147-173.
Dong et al., Genetic analysis of parasitism in the soybean cyst nematode Heterodera glycines, Genetics Society of America, 1997, vol. 146, pp. 1311-1318.

(Continued)

*Primary Examiner* — David H Kruse
(74) *Attorney, Agent, or Firm* — Dentons US LLP

(57) ABSTRACT

A transgenic soybean resistant to soybean cyst nematode (SCN), or parts thereof, including an artificial DNA construct encoding a serine hydroxymethyltransferase protein (e.g., GmSHMT). Also provided are GmSHMT alleles containing mutations R130P and Y358N along with research and breeding methods and compositions including such.

3 Claims, 10 Drawing Sheets

Specification includes a Sequence Listing.

(56) References Cited

OTHER PUBLICATIONS

Dykxhoorn et al., The silent revolution: RNA interference as basic biology, research tool, and therapeutic, Annu. Rev. Med., 2005, vol. 56, pp. 401-423.

Elhai et al., Conjugal transfer of DNA to cyanobacteria, Methods in Enzymology, 1988, vol. 167, pp, 747-754.

Endo, Histological responses of resistant and susceptible soybean varieties, and backcross progeny to entry and development of Heterodera glycines, Phytopathology, 1965, vol. 55, pp. 249-372.

Ernst et al., The broad-spectrum potato cyst nematode resistance gene (Hero) from tomato is the only member of a large gene family of NBS-LRR genes with an unusual amino acid repeat in the LRR region, The Plant Journal, 2002, vol. 31, No. 2, pp. 127-136.

Fanning et al., Gene-Expressed RNA as a Therapeutic: Issues to Consider, Using Ribozymes and Small Hairpin RNA as Specific Examples, HEP, 2006, vol. 173, pp. 289-303.

GenBank Accession No. JQ714083, Glycine max cultivar Forrest serine hydroxymethyltransferase (SHMT) gene, promoter region and complete cds, 2012, 2 pages.

Genbank Accession No. JQ714084, Glycine max cultivar Essex serine hydroxymethyltransferase (SHMT) gene, promoter region and complete cds, 2012, 2 pages.

Ghadessy et al., Directed evolution of polymerase function by compartmentalized self-replication, PNAS, 2001, vol. 98, No. 8, pp. 4552-4557.

Hartwig et al., Registration of 'Forrest' soybeans, Registration of Cultivars, Crop Sci., 1973, 1 page.

Heil et al., Is mutated serine hydroxymethyltransferase (SHMT) involved in the etiology of neural tube defects?, Molecular Genetics and Metabolism, 2001, vol. 73, pp. 164-172.

Helene et al., Control of gene expression by triple helix-forming oligonucleotides, Annals of New York Academy of Sciences, 1992, vol. 660, pp. 27-36.

Hofmann et al., Metabolic profiling reveals local and systemic responses of host plants to nematode parasitism, The Plant Journal, 2010, vol. 62, pp. 1058-1071.

Holtorf et al., Promoter subfragments of the sugar beet V-type H+-ATPase subunit c isoform drive the expression of transgenes in the moss Physcomitrella patens, Plant Cell Rep, 2002, vol. 21, No. 4, pp. 341-346.

Horstmann et al., Quantitative promoter analysis in Physcmitrella patens: a set of plant vectors activating gene expression within three orders of magnitude, BMC Biotechnology, 2004, vol. 4, 13 pages.

International Search Report and Written Opinion dated Nov. 1, 2013 in related PCT Application No. PCT/US2013/043392 filed May 30, 2013, 13 pages.

Ithal et al., Developmental transcript profiling of cyst nematode feeding cells in soybean roots, Molecular Plant-Microbe Interactions, 2007, vol. 20, No. 5, pp. 510-525.

Jefferson, Assaying chimeric genes in plants: the GUS gene fusion system, Plant Molecular Biology Reporter, 1987, vol. 5, No. 4, pp. 387-405.

Jost et al., Isolation and characterisation of three moss-derived beta-tubulin promoters suitable for recombinant expression, Curr Genet, 2005, vol. 47, pp. 111-120.

Kandoth et al., The soybean Rhg1 locus for resistance to the soybean cyst nematode heterodera glycines regulates the expression of a large number of stress- and defense-related genes in degenerating feeding cells, Plant Physiology, 2011, vol. 155, pp. 1960-1975.

Kim, Role of folate in colon cancer development and progression, The Journal of Nutrition, 2003, pp. 3731-3739.

Koenning et al., Suppression of soybean yield potential in the continental United States by plant diseases from 2006 to 2009, Plant Health Progress, 2010, 5 pages.

Kumar et al., Predicting the effects of coding non-synonymous variants on protein function using the SIFT algorithm, Nature Protocols, 2009, vol. 4, No. 8, pp. 1073-1082.

Lee et al., Aptamer therapeutics advance, Curr Opin Chem Biol., 2006, vol. 10, pp. 282-289.

Lim et al., Polymorphisms in cytoplasmic serine hydroxymethyltransferase and methylenetetrahydrofolate reductase affect the risk of cardiovascular disease in men, The Journal of Nutrition, 2005, 1989-1994.

Link et al., Beyond toothpicks: new methods for isolating mutant bacteria, Nature Reviews, 2007, vol. 5, pp. 680-688.

Liu et al., Soybean cyst nematode resistance in soybean is independent of the Rhg4 locus LRR-RLK gene, Funct Integr Genomics, 2011, vol. 11, pp. 539-549.

Maher, DNA triple-helix formation: an approach to artificial gene repressors?, BioEssays, 1992, vol. 14, No. 12, pp. 807-815.

Malik et al., A constitutive gene expression system derived from the tCUP cryptic promoter elements, Theoretical and Applied Genetics, 2002, vol. 105, No. 4, pp. 505-514.

Matson et al., Evidence of a fourth gene for resistance to the soybean cyst nematode, Crop Science, 1965, p. 477.

McClung et al., Integrated temporal regulation of the photorespiratory pathway. Circadian regulation of two *Arabidopsis* genes encoding serine hydroxymethyltransferase, Plant Physiology, 2000, vol. 123, pp. 381-391.

Meksem et al., Two large-insert soybean genomic libraries constructed in a binary vector: applications in chromosome walking and genome wide physical mapping, Theor Appl Gene, 2000, vol. 101, pp. 747-755.

Meksem et al., 'Forrest' resistance to the soybean cyst nematode is bigenic: saturation mapping of the Rhg1 and Rhg4 loci, Theor Appl Genet, 2001, vol. 103, pp. 710-717.

Meksem et al., Tilling: A reverse genetics and a functional genomics tool in soybean, The Handbook of Plant Functional Genomics: Concepts and Protocols, 2008, pp. 251-265.

Melito et al., A nematode demographics assay in transgenic roots reveals no significant impacts of the Rhg1 locus LRR-Kinase on soybean cyst nematode resistance, BMC Plant Biology, 2010, vol. 10, No. 104, 14 pages.

Meyer et al., Identification and analyses of candidate genes for Rpp4-Mediated resistance to Asian soybean rust in soybean, Plant Physiology, 2009, vol. 150, pp. 295-307.

Milligan et al., The root knot nematode resistance gene Mi from tomato is a member of the leucine zipper, nucleotide binding, leucine-rich repeat family of plant genes, The Plant Cell, 1998, vol. 10, pp. 1307-1319.

Moreno et al., *Arabidosis* SHMT1, a serine hydroxymethyltransferase that functions in the photorespiratory pathway influences resistance to biotic and abiotic stress, The Plant Journal, 2005, vol. 41, pp, 451-463.

Niblack et al., Distribution, density, and diversity of Heterodera glycines in Missouri, Supplement to Journal of Nematology, 1993, vol. 25, No. 4S, pp. 880-886.

Niblack et al., Shift in virulence of soybean cyst nematode is associated with use of resistance from PI 88788, Plant Health Progress, Plant Management Network, 2008, 7 pages.

Novakovic et al., Effects of folate deficiency on gene expression in the apoptosis and cancer pathways in colon cancer cells, Carcinogenesis, 2006, vol. 27, No. 5, pp. 916-924.

Paal et al., Molecular cloning of the potato Gro 1-4 gene conferring resistance to pathotype Ro1 of the root cyst nematode Globodera rostochiensis, based on a candidate gene approach, The Plant Journal, 2004, vol. 38, pp. 285-297.

Pandey et al., Functional analysis of the Asian soybean rust resistance pathway mediated by Rpp2, Molecular Plant-Microbe Interactions, 2011, vol. 24, No. 2, pp. 194-206.

Pushparaj et al., Short interfering RNA (siRNA) as a novel therapeutic, Clin Exp Pharmacol Physiol., 2006, vol. 33, No. 5-6, pp. 504-510.

Renwick et al., The crystal structure of human cytosolic serine hydroxymethyltransferase: a target for cancer chemotherapy, Structure, 1998, vol. 6, No. 9, pp. 1105-1116.

Reynolds et al., Rational siRNA design for RNA interference, Nature Biotechnology, 2003, vol. 22, No. 3, pp. 326-330.

Riggs et al., Ultrastructural changes in Peking soybeans infected with Heterodera glycines, Phytopathology, 1973, vol. 63, pp. 76-84.

(56) References Cited

OTHER PUBLICATIONS

Sagner et al., Rapid filter assay for the detection of DNA polymerase activity: direct identification of the gene for the DNA polymerase from Thermus aquaticus, Gene, 1991, vol. 97, No. 1, pp. 119-126.
Saidi et al., Controlled expression of recombinant proteins in Physcomitrella patens by a conditional heat-shock promoter: a tool for plant research and biotechnology, Plant Molecular Biology, 2005, vol. 59, pp. 697-711.
Sali et al., Comparative protein modelling by satisfaction of spatial restraints, J. Mol. Biol., 1993, pp. 779-815.
Scarsdale et al., Crystal structure at 2.4 Å resolution of *E. coli* serine hydroxymethyltransferase in complex with glycine substrate and 5-formyl tetrahydrofolate, J. Mol. Biol., 2000, vol. 296, pp. 155-168.
Skibola et al., Polymorphisms in the thymidylate synthase and serine hydroxymethyltransferase genes and risk of adult acute lymphocytic leukemia, Blood, 2002, vol. 99, No. 10, pp. 3786-3791.
Smith et al., Registration of essex soybean, Crop Science, 1973, p. 495.
Stavolone et al., Cestrum yellow leaf curling virus (CmYLCV) promoter: a new strong constitutive promoter for heterologous gene expression in a wide variety of crops, Plant Molecular Biology, 2003, vol. 53, pp. 703-713.
Studier, Protein production by auto-induction in high-density shaking cultures, Protein Expression and Purification, 2005, vol. 41, pp. 207-234.
Sukanya et al., Serine hydroxymethyltransferase from mung bean (*Vigna radiata*) is not a pyridoxal-5'-phosphate-dependent enzyme, Plant Physiol., 1991, vol. 95, 351-357.
Van Der Vossen et al., Homologues of a single resistance-gene cluster in potato confer resistance to distinct pathogens: a virus and a nematode, The Plant Journal, 2000, vol. 23, No. 5, pp. 567-576.
Wang et al., Dual roles for the variable domain in protein trafficking and host-specific recognition of Heterodera glycines CLE effector proteins, New Phytologist, 2010, vol. 187, pp. 1003-1007.
Weise et al., Use of Physcomitrella patens actin 5' regions for high transgene expression: importance of 5' introns, Applied Microbiology and Biotechnology, 2006, vol. 70, pp. 337-345.
Xiao et al., Analysis of the cDNAs of hypothetical genes on *Arabidopsis* chromosome 2 reveals numerous transcript variants, Plant Physiology, 2005, vol. 139, pp. 1323-1337.
You et al., Use of bacterial quorum-sensing components to regulate gene expression in plants, Plant Physiology, 2006, vol. 140, pp. 1205-1212.
Zeidler et al., Tetracycline-regulated reporter gene expression in the moss physcomitrella patens, Plant Molecular Biology, 1996, vol. 30, pp. 199-205.
Zhang et al., The development of an efficient multipurpose bean pod mottle virus viral vector set for foreign gene expression and RNA silencing, Plant Physiology, 2010, vol. 153, pp. 52-65.

\* cited by examiner

FIG. 4A-G
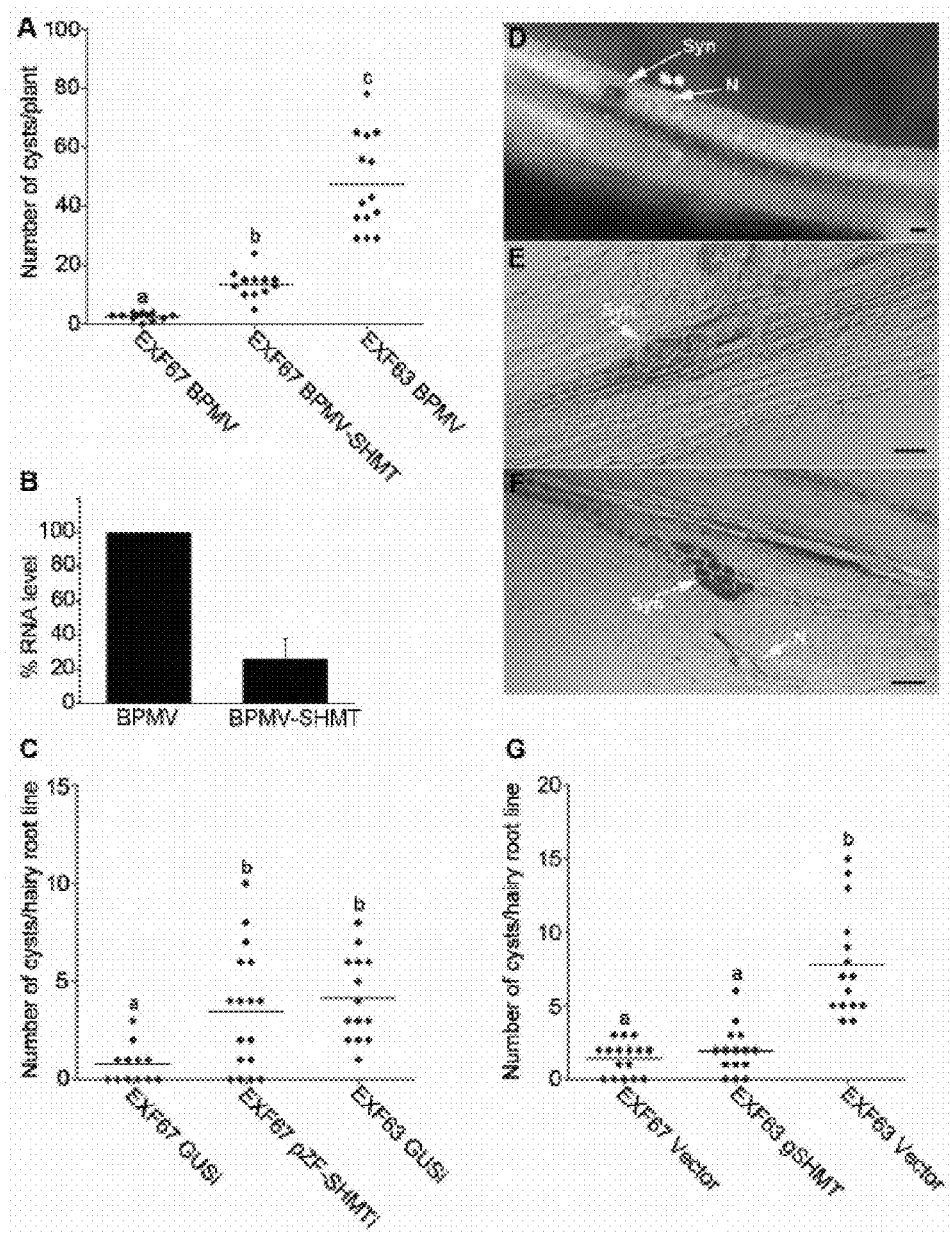

FIG. 5A-B
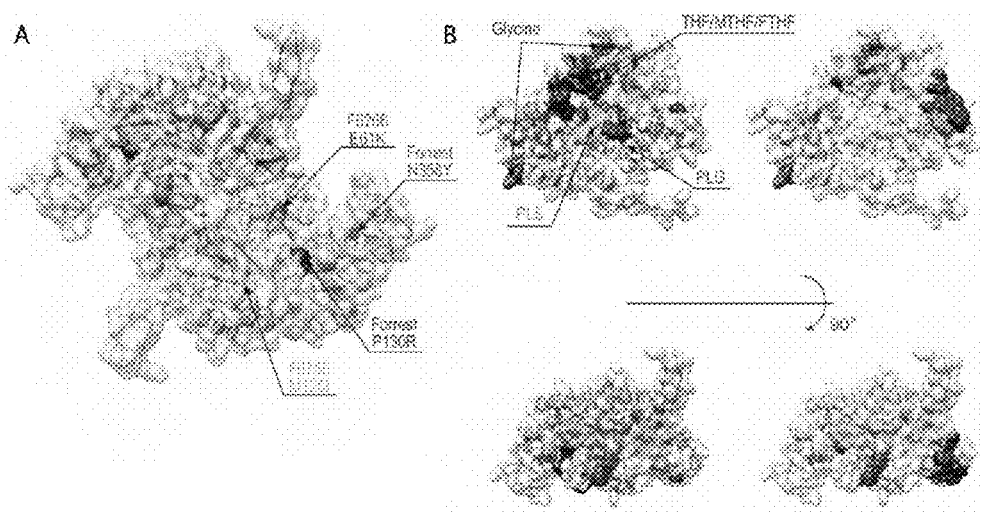

FIG. 6

```
F-GmSUB1-cDNA   cccaaagtgttgtc    tcgagaaccgtgggagaaagctacaccaccactcgatcatgg 360
E-GmSUB1-cDNA   cccaaagtgttgtc    tcgagaaccgtgggagaaagctacaccaccactcgatcatgg 360
W-GmSUB1-cDNA   cccaaagtgttgtc    tcgagaaccgtgggagaaagctacaccaccactcgatcatgg 360
                **************    ******************************************

F-GmSUB1-cDNA   cttggtaacgatattacc  aggggggaaagcttatcagctacaaaattggcacacaag 1140
E-GmSUB1-cDNA   cttggtaacgatattacc  aggggggaaagcttatcagctacaaaattggcacacaag 1140
W-GmSUB1-cDNA   cttggtaacgatattacc  aggggggaaagcttatcagctacaaaattggcacacaag 1140
                ******************  ***************************************

F-GmSUB1-cDNA   tataaatgccgcaagaaatttagtctcctcaacctgaactatc    atcacagtccca 2040
E-GmSUB1-cDNA   tataaatgccgcaagaaatttagtctcctcaacctgaactatc    atcacagtccca 2040
W-GmSUB1-cDNA   tataaatgccgcaagaaatttagtctcctcaacctgaactatc    atcacagtccca 2040
                *******************************************    ************

F-GmSUB1-cDNA   tacattgctcatgtt    accgtatggaatcaccgtttctgtgaagccaagcatcttg 2160
E-GmSUB1-cDNA   tacattgctcatgtt    accgtatggaatcaccgtttctgtgaagccaagcatcttg 2160
W-GmSUB1-cDNA   tacattgctcatgtt    accgtatggaatcaccgtttctgtgaagccaagcatcttg 2160
                ***************    ****************************************
```

FIG. 7A

```
F-GmSHMT-Promoter  caatggcaccaatgcccaatgggagatttaagtcaagcccaacatcaacctctgaaatta 60
E-GmSHMT-Promoter  caatggcaccaatgcccaatgggagatttaagtcaagcccaacatcaacctctgaaatta 60
W-GmSHMT-Promoter  caatggcaccaatgcccaatgggagatttaagtcaagcccaacatcaacctctgaaatta 60
                   ************************************************************

F-GmSHMT-Promoter  tgaattatgaaattaaaatgcttcctagtaagtgaactagttgcatctcatttatatcat 120
E-GmSHMT-Promoter  tgaattatgaaattaaaatgcttcctagtaagtgaactagttgcatctcatttatatcat 120
W-GmSHMT-Promoter  tgaattatgaaattaaaatgcttcctagtaagtgaactagttgcatctcatttatatcat 120
                   ************************************************************

F-GmSHMT-Promoter  aaatttcgaactacgactttcttggccatgttagtaaagtttgggggattgttcaaaatt 180
E-GmSHMT-Promoter  aaatttcgaactacgactttcttggccatgttagtaaagtttgggggattgttcaaaatt 180
W-GmSHMT-Promoter  aaatttcgaactacgactttcttggccatgttagtaaagtttgggggattgttcaaaatt 180
                   ************************************************************

F-GmSHMT-Promoter  ggtggagtggttcagcttaatctccaaattatttgttctaagttgttttggtaggcaggt 240
E-GmSHMT-Promoter  ggtggagtggttcagcttaatctccaaattatttgttctaagttgttttggtaggcaggt 240
W-GmSHMT-Promoter  ggtggagtggttcagcttaatctccaaattatttgttctaagttgttttggtaggcaggt 240
                   ************************************************************

F-GmSHMT-Promoter  ttaattttttcctgatcctgggaaaaaaattattgataccatattaacatctcttgacga 300
E-GmSHMT-Promoter  ttaattttttcctgatcctgggaaaaaaattattgataccatattaacatctcttgacga 300
W-GmSHMT-Promoter  ttaattttttcctgatcctgggaaaaaaattattgataccatattaacatctcttgacga 300
                   ************************************************************

F-GmSHMT-Promoter  tgctacgagatttctcatgattatagaactgagtagggtggcttaaaaggttttatttta 360
E-GmSHMT-Promoter  tgctacgagatttctcatgattatagaactgagtagggtggcttaaaaggttttatttta 360
W-GmSHMT-Promoter  tgctacgagatttctcatgattatagaactgagtagggtggcttaaaaggttttatttta 360
                   ************************************************************

F-GmSHMT-Promoter  aatataatttcaccacattgaattgggtattagtaaactggttactggtatgcctgtaaa 420
E-GmSHMT-Promoter  aatataatttcaccacattgaattgggtattagtaaactggttactggtatgcctgtaaa 420
W-GmSHMT-Promoter  aatataatttcaccacattgaattgggtattagtaaactggttactggtatgcctgtaaa 420
                   ************************************************************

F-GmSHMT-Promoter  gtggacaatgataaatgtttttatagaagttggtatggattttaaaatagctcatgtata 480
E-GmSHMT-Promoter  gtggacaatgataaatgtttttatagaagttggtatggattttaaaatagctcatgtata 480
W-GmSHMT-Promoter  gtggacaatgataaatgtttttatagaagttggtatggattttaaaatagctcatgtata 480
                   ************************************************************

F-GmSHMT-Promoter  aaatgtgaaaaaggaaacgtgaactaaaatgctaataataaaagataaagactaaattaa 540
E-GmSHMT-Promoter  aaatgtgaaaaaggaaacgtgaactaaaatgctaataataaaagataaagactaaattaa 540
W-GmSHMT-Promoter  aaatgtgaaaaaggaaacgtgaactaaaatgctaataataaaagataaagactaaattaa 540
                   ************************************************************

F-GmSHMT-Promoter  ttaaagttaaaggataaaatgcttgttacatcaagtcattttaaaggtgcactattagag 600
E-GmSHMT-Promoter  ttaaagttaaaggataaaatgcttgttacatcaagtcattttaaaggtgcactattagag 600
W-GmSHMT-Promoter  ttaaagttaaaggataaaatgcttgttacatcaagtcattttaaaggtgcactattagag 600
                   ************************************************************

F-GmSHMT-Promoter  gctgcacagtaaaagttaacactgatatattttaaagatgttcttagttaaatagcttt 660
E-GmSHMT-Promoter  gctgcacagtaaaagttaacactgatatattttaaagatgttcttagttaaatagcttt 660
W-GmSHMT-Promoter  gctgcacagtaaaagttaacactgatatattttaaagatgttcttagttaaatagcttt 660
                   ************************************************************

F-GmSHMT-Promoter  tgacttgatggggtgaagacacaagaggttgttgttgcgatgtgattttggctgaatatg 720
E-GmSHMT-Promoter  tgacttgatggggtgaagacacaagaggttgttgttgcgatgtgattttggctgaatatg 720
W-GmSHMT-Promoter  tgacttgatggggtgaagacacaagaggttgttgttgcgatgtgattttggctgaatatg 720
                   ************************************************************

F-GmSHMT-Promoter  catgcctgctgaacattgacttcattgttaaatcaaaattaatcccatagacctattgta 780
E-GmSHMT-Promoter  catgcctgctgaacattgacttcattgttaaatcaaaattaatcccatagacctattgta 780
W-GmSHMT-Promoter  catgcctgctgaacattgacttcattgttaaatcaaaattaatcccatagacctattgta 780
                   ************************************************************

F-GmSHMT-Promoter  ttatttaagggatcaatttcataaatcaaaatttattggttgggaaaaaaacaatgtt 840
E-GmSHMT-Promoter  ttatttaagggatcaatttcataaatcaaaatttattggttgggaaaaaaacaatgtt 840
W-GmSHMT-Promoter  ttatttaagggatcaatttcataaatcaaaatttattggttgggaaaaaaacaatgtt 840
                   ************************************************************
```

FIG. 7A (continued)

```
F-GmSHMT-Promoter  tagtagttcccagtcatattcagaaacctacaaattaactatcccccatgttaatgaagc  900
E-GmSHMT-Promoter  tagtagttcccagtcatattcagaaacctacaaattaactatcccccatgttaatgaagc  900
W-GmSHMT-Promoter  tagtagttcccagtcatattcagaaacctacaaattaactatcccccatgttaatgaagc  900
                   ************************************************************

F-GmSHMT-Promoter  aaggtgtgggggaaggaaagagtcagcatcagtgaagtagagaggggggttggtgatttt  960
E-GmSHMT-Promoter  aaggtgtgggggaaggaaagagtcagcatcagtgaagtagagaggggggttggtgatttt  960
W-GmSHMT-Promoter  aaggtgtgggggaaggaaagagtcagcatcagtgaagtagagaggggggttggtgatttt  960
                   ************************************************************

F-GmSHMT-Promoter  ggtgggaataaattggctatattgcccccaccaacctcgttgctaccaaataccaacaac  1020
E-GmSHMT-Promoter  ggtgggaataaattggctatattgcccccaccaacctcgttgctaccaaataccaacaac  1020
W-GmSHMT-Promoter  ggtgggaataaattggctatattgcccccaccaacctcgttgctaccaaataccaacaac  1020
                   ************************************************************

F-GmSHMT-Promoter  actgactcactgagaattgggaaagaaacttaaaaccaagtcttgcagtgacgtacatg   1080
E-GmSHMT-Promoter  actgactcactgagaattgggaaagaaacttaaaaccaagtcttgcagtgacgtacatg   1080
W-GmSHMT-Promoter  actgactcactgagaattgggaaagaaacttaaaaccaagtcttgcagtgacgtacatg   1080
                   ***********************************************************

F-GmSHMT-Promoter  agtgtgtgcatcacacattcaggtttccagtcaaattgtagaacaaatgaatttcttgct  1140
E-GmSHMT-Promoter  agtgtgtgcatcacacattcaggtttccagtcaaattgtagaacaaatgaatttcttgct  1140
W-GmSHMT-Promoter  agtgtgtgcatcacacattcaggtttccagtcaaattgtagaacaaatgaatttcttgct  1140
                   ************************************************************

F-GmSHMT-Promoter  ttaacttaagttgaagtttaagaagtgaagctgatgcttgttttgaatgaaaagccttt   1200
E-GmSHMT-Promoter  ttaacttaagttgaagtttaagaagtgaagctgatgcttgttttgaatgaaaagccttt   1200
W-GmSHMT-Promoter  ttaacttaagttgaagtttaagaagtgaagctgatgcttgttttgaatgaaaagccttt   1200
                   ***********************************************************

F-GmSHMT-Promoter  gatagtttgatgtaagcattttccaaatttaactcttcccatgcttgacagagccaatta  1260
E-GmSHMT-Promoter  gatagtttgatgtaagcattttccaaatttaactcttcccatgcttgacagagccaatta  1260
W-GmSHMT-Promoter  gatagtttgatgtaagcattttccaaatttaactcttcccatgcttgacagagccaatta  1260
                   ************************************************************

F-GmSHMT-Promoter  agctaactggtttgataacaagtaaacttctaaatctatgagtatgagtgcatgcagcac  1320
E-GmSHMT-Promoter  agctaactggtttgataacaagtaaacttctaaatctatgagtatgagtgcatgcagcac  1320
W-GmSHMT-Promoter  agctaactggtttgataacaagtaaacttctaaatctatgagtatgagtgcatgcagcac  1320
                   ************************************************************

F-GmSHMT-Promoter  accttttaaacacaagccactgttttgtctttttatcaacagaaagagaatcctactaa  1380
E-GmSHMT-Promoter  accttttaaacacaagccactgttttgtctttttatcaacagaaagagaatcctactaa  1380
W-GmSHMT-Promoter  accttttaaacacaagccactgttttgtctttttatcaacagaaagagaatcctactaa  1380
                   ***********************************************************

F-GmSHMT-Promoter  taacactaatcaagatcgctgctcttttctgtttattttcttaataaattaactttgt    1440
E-GmSHMT-Promoter  taacactaatcaagatcgctgctcttttctgtttattttcttaataaattaactttgt    1440
W-GmSHMT-Promoter  taacactaatcaagatcgctgctcttttctgtttattttcttaataaattaactttgt    1440
                   **********************************************************

F-GmSHMT-Promoter  tttgtactcctgttaaacaactgctctatttgtttcatgtgttgcattaaataacatggt  1500
E-GmSHMT-Promoter  tttgtactcctgttaaacaactgctctatttgtttcatgtgttgcattaaataacatggt  1500
W-GmSHMT-Promoter  tttgtactcctgttaaacaactgctctatttgtttcatgtgttgcattaaataacatggt  1500
                   ************************************************************

F-GmSHMT-Promoter  tttattcacatctacaagcaaaatttcctaaaaactgtgaatgatgtagaagcaagtcat  1560
E-GmSHMT-Promoter  tttattcacatctacaagcaaaatttcctaaaaactgtgaatgatgtagaagcaagtcat  1560
W-GmSHMT-Promoter  tttattcacatctacaagcaaaatttcctaaaaactgtgaatgatgtagaagcaagtcat  1560
                   ************************************************************

F-GmSHMT-Promoter  ttatgttttgaaattcacgcattggagtttctaacgcccaaccaaccaaacggtaatatg  1620
E-GmSHMT-Promoter  ttatgttttgaaattcacgcattggagtttctaacgcccaaccaaccaaacggtaatatg  1620
W-GmSHMT-Promoter  ttatgttttgaaattcacgcattggagtttctaacgcccaaccaaccaaacggtaatatg  1620
                   ************************************************************

F-GmSHMT-Promoter  aatatcgtgtttggaacaaattagaatttaggacataattttcacatcagaataaaatgt  1680
E-GmSHMT-Promoter  aatatcgtgtttggaacaaattagaatttaggacataattttcacatcagaataaaatgt  1680
W-GmSHMT-Promoter  aatatcgtgtttggaacaaattagaatttaggacataattttcacatcagaataaaatgt  1680
                   ************************************************************
```

FIG. 7A (continued)

```
F-GmSHMT-Promoter    taggaattttttgcttttacgttttttcgcattaaaataatgtgatttatcggttgttcctg  1740
E-GmSHMT-Promoter    taggaattttttgcttttacgttttttcgcattaaaataatgtgatttatcggttgttcctg  1740
W-GmSHMT-Promoter    taggaattttttgcttttacgttttttcgcattaaaataatgtgatttatcggttgttcctg  1740
                     ************************************************************

F-GmSHMT-Promoter    aacaataaccatcgatgtaattataaaattctaatttgtcctatcctggggcgtcaacgt  1800
E-GmSHMT-Promoter    aacaataaccatcgatgtaattataaaattctaatttgtcctatcctggggcgtcaacgt  1800
W-GmSHMT-Promoter    aacaataaccatcgatgtaattataaaattctaatttgtcctatcctggggcgtcaacgt  1800
                     ************************************************************

F-GmSHMT-Promoter    ccagccaaatgcgtaacatttattctgatgtaaaaattattattattattatagataat  1860
E-GmSHMT-Promoter    ccagccaaatgcgtaacatttattctgatgtaaaaattattattattattatagataat  1860
W-GmSHMT-Promoter    ccagccaaatgcgtaacatttattctgatgtaaaaattattattattattatagataat  1860
                     ************************************************************

F-GmSHMT-Promoter    aaaatcttgttcctgaacaataaccatcaatgtaattataaaattgaatcttagactcaa  1920
E-GmSHMT-Promoter    aaaatcttgttcctgaacaataaccatcaatgtaattataaaattgaatcttagactcaa  1920
W-GmSHMT-Promoter    aaaatcttgttcctgaacaataaccatcaatgtaattataaaattgaatcttagactcaa  1920
                     ************************************************************

F-GmSHMT-Promoter    aactagttattaatctggaacaatgtttactcaaaactagttattaatagtattttttaag  1980
E-GmSHMT-Promoter    aactagttattaatctggaacaatgtttactcaaaactagttattaatagtattttttaag  1980
W-GmSHMT-Promoter    aactagttattaatctggaacaatgtttactcaaaactagttattaatagtattttttaag  1980
                     ************************************************************

F-GmSHMT-Promoter    ttaatttgaaattttttttttcggcgttaaacaaatactagatgtttatactacaaatatt  2040
E-GmSHMT-Promoter    ttaatttgaaattttttttttcggcgttaaacaaatactagatgtttatactacaaatatt  2040
W-GmSHMT-Promoter    ttaatttgaaattttttttttcggcgttaaacaaatactagatgtttatactacaaatatt  2040
                     ************************************************************

F-GmSHMT-Promoter    gattattgattataaatttataaatgtt aaaaaaaaaaaagagaaaacaaagaattga  2099
E-GmSHMT-Promoter    gattattgattataaatttataaatgtt aaaaaaaaaaaaagagaaaacaaagaattga  2100
W-GmSHMT-Promoter    gattattgattataaatttataaatgtt aaaaaaaaaaaaagagaaaacaaagaattga  2100
                     ****************************  *****************************

F-GmSHMT-Promoter    agttgtggttggtagtaaaccagcaccaggcgaacaagtggacacaatttacctacaagt  2159
E-GmSHMT-Promoter    agttgtggttggtagtaaaccagcaccaggcgaacaagtggacacaatttacctacaagt  2160
W-GmSHMT-Promoter    agttgtggttggtagtaaaccagcaccaggcgaacaagtggacacaatttacctacaagt  2160
                     ************************************************************

F-GmSHMT-Promoter    aactaaccaaccggaagcacaggctacaacggtcctttcacacccggtctcaaagctttt  2219
E-GmSHMT-Promoter    aactaaccaaccggaagcacaggctacaacggtcctttcacacccggtctcaaagctttt  2220
W-GmSHMT-Promoter    aactaaccaaccggaagcacaggctacaacggtcctttcacacccggtctcaaagctttt  2220
                     ************************************************************

F-GmSHMT-Promoter    aaaaacgaacacatacgcactca atttccattccacctcaacaaacacaacaacactct  2279
E-GmSHMT-Promoter    aaaaacgaacacatacgcactca atttccattccacctcaacaaacacaacaacactct  2280
W-GmSHMT-Promoter    aaaaacgaacacatacgcactca atttccattccacctcaacaaacacaacaacactct  2280
                     *********************** ************************************

F-GmSHMT-Promoter    ctcttctcgctcttggcttttcgctcttcactcactctcattcattcatttccaccgttc  2339
E-GmSHMT-Promoter    ctcttctcgctcttggcttttcgctcttcactcactctcattcattcatttccaccgttc  2340
W-GmSHMT-Promoter    ctcttctcgctcttggcttttcgctcttcactcactctcattcattcatttccaccgttc  2340
                     ************************************************************
```

SOYBEAN RESISTANT TO CYST NEMATODES

CROSS-REFERENCE TO RELATED APPLICATIONS

The present application claims the benefit of PCT International Application No. PCT/US13/43392, filed 30 May 2013; which claims the benefit of U.S. Provisional Application Ser. No. 61/653,227, filed 30 May 2012; all of which are incorporated herein by reference in their entireties.

STATEMENT REGARDING FEDERALLY SPONSORED RESEARCH OR DEVELOPMENT

This invention was made with government support under grant number 0820642 awarded by National Science Foundation Plant Genome Research Program and DBI-0845196 awarded by National Science Foundation. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to methods of conferring resistance to nematodes in soybeans.

BACKGROUND OF THE INVENTION

Soybean cyst nematode causes more than one billion dollars in annual yield losses to US soybean producers and is a continuing problem in soybean producing regions throughout the world. Virulent populations of *Heterodera glycines*, the nematode responsible for this yield loss, have been identified on most known resistance sources. But the soybean genes which confer resistance to soybean cyst nematode have not been previously cloned.

Cyst nematodes belonging to genera *Heterodera* and *Globodera* include some of the most economically important classes of plant-parasitic nematodes. Different species of these nematodes feed selectively on certain host plants as obligate sedentary endoparasites by inducing specialized feedings sites (syncytia) within host roots. The soybean cyst nematode (SCN) *Heterodera glycines* Ichinohe has a host range limited to plants in the family Leguminosae and some weeds. It is consistently the most economically important pathogen on soybean (*Glycine max* (L.) Merr.) (Koenning and Wrather, 2010). Infective second-stage juveniles (J2) hatch from eggs in the soil and penetrate plant roots utilizing a hollow mouth spear (stylet) to mechanically perforate the plant cell wall and to secrete cell wall digesting enzymes that facilitate intracellular migration through the root cortex to a pericycle or endodermal cell near the vasculature. Once a cell has been selected for feeding, the nematode delivers a suite of effector proteins into the cell leading to its transformation into a unique, highly metabolically active feeding cell. The now sedentary juvenile feeds from this cell as it progresses through a 25-30 day life cycle divided into four juvenile (J1-J4) and the sexually dimorphic adult life stages. After fertilization by a male, the adult female retains hundreds of eggs in her uterus and following her death forms a protective cyst that allows the eggs to survive for years in the soil in the absence of a host. The host plant suffers from loss of nutrients and reduced transport through the vasculature, manifested as less vigorous growth and reduced yield.

Its amphimictic lifestyle and unique survival strategy complicate current measures to control SCN. The use of nematicides is restricted and not cost-effective for soybean producers. Current methods to control SCN include a combination of nonhost crop rotation and planting of resistant cultivars. Soybean breeders have been successful in developing SCN resistant cultivars. The first Rhg (for resistance to *Heterodera glycines*) genes were identified in the early 1960's (Caldwell et al., 1960; Matson and Williams, 1965) and since then numerous papers on the identification and localization of QTL (quantitative trait loci) underlying resistance to SCN from a variety of different germplasm sources have been published. QTL on chromosome 18 (rhg1) and chromosome 8 (Rhg4) have been consistently mapped in a variety of germplasm sources (Concibido et al., 2004). In some sources, such as PI88788, rhg1 is sufficient for full resistance and displays incomplete dominance (Concibido et al., 2004). In other cases, such as the soybean cultivar (cv.) Forrest, full resistance to SCN requires both rhg1 and Rhg4, with Rhg4 exhibiting dominant gene action (Meksem et al., 2001).

Plants carrying Rhg genes display an incompatible interaction between host and parasite. The roots of plants carrying Rhg genes are penetrated by infective J2s, but feeding cells ultimately degenerate and most of the nematodes die before reaching adult stages (Endo, 1965; Riggs et al., 1973). Genetic variability in *H. glycines* is prevalent and nematodes that survive on resistant cultivars carry the undefined ror (reproduction on a resistant host) alleles (Dong and Opperman, 1997) leading to population shifts in the field as a consequence of soybean resistance monoculture (Niblack et al., 2008). Understanding of resistance to SCN is limited because the genes underlying identified SCN resistance QTL have not been cloned (Melito et al., 2010; Liu et al., 2010).

SUMMARY OF THE INVENTION

Among the various aspects of the present disclosure is the provision of a soybean plant having resistance to soybean cyst nematode (SCN).

One aspect of the present disclosure provides a transgenic soybean resistant to soybean cyst nematode (SCN). The SCN resistant soybean includes a serine hydroxymethyltransferase gene (GmSHMT) conferring the resistant phenotype. In some embodiments, the GmSHMT gene is exogenous to the soybean and thereby provides SCN resistance. In some embodiments, the GmSHMT gene is endogenous to the soybean and transformation increases expression of GmSHMT, thereby increasing SCN resistance.

In some embodiments, the soybean plant is transformed with an artificial DNA construct comprising, as operably associated components in the 5' to 3' direction of transcription: a promoter that functions in soybean; a polynucleotide comprising a sequence selected from the group consisting of (a) SEQ ID NO: 1 or a sequence 95% identical thereto having serine hydroxymethyltransferase activity; (b) a nucleotide sequence encoding a polypeptide of SEQ ID NO: 2 or a sequence 95% identical thereto having serine hydroxymethyltransferase activity; (c) a nucleotide sequence that hybridizes under stringent conditions to a nucleic acid sequence of SEQ ID NO: 1, wherein the polynucleotide encodes a polypeptide having serine hydroxymethyltransferase activity, wherein said stringent conditions comprise incubation at 65° C. in a solution comprising 6×SSC (0.9 M sodium chloride and 0.09 M sodium citrate); and (d) a polynucleotide complementary to the polynucleotide sequence of (a), (b), or (c); and a transcriptional termination sequence; wherein the transgenic soybean exhibits increased SCN resistance.

In some embodiments, the soybean plant is an agronomically elite soybean variety with soybean cyst nematode (SCN) resistance, comprising an GmSHMT allele containing mutations R130P and Y358N. In some embodiments, the soybean plant is prepared by (a) crossing first and second soybean plants, wherein the first and second plants collectively comprise a GmSHMT allele containing mutations R130P and Y358N resulting in an SCN resistant phenotype, and wherein the first and second plants collectively comprise germplasm capable of conferring agronomically elite characteristics to a progeny plant of said plants; and (b) assaying progeny soybean plants resulting from the crossing for agronomically elite characteristics and for SCN resistance; and (c) selecting at least a first progeny plant comprising said SCN resistant phenotype and agronomically elite characteristics to obtain the desired plant.

Another aspect of the present disclosure is a plant part of any SCN resistant soybean plant described herein.

Another aspect of the present disclosure is an artificial DNA construct including a promoter that functions in soybean; a polynucleotide encoding a polypeptide having serine hydroxymethyltransferase activity; and a transcriptional termination sequence.

Another aspect of the present disclosure is a method of increasing soybean cyst nematode (SCN) of a soybean including transforming a plant an artificial DNA construct of the present disclosure.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A shows a high density genetic map of the Rhg4 locus. The black horizontal line represents approximately 300 Kbp of the Rhg4 chromosomal interval. The arrows under the black horizontal line designate the position of each DNA marker and its name. Numbers above the black horizontal line denote the position of each marker relative to the LRR-RLK marker (an LRR-RLK gene at the Rhg4 locus described previously in Liu et al. 2011), which was assigned the position '0'. Solid arrows designate polymorphic alleles between Essex (E) or Williams 82 (W) and Forrest (F), dashed arrows represent the DNA markers with Forrest (F) alleles found in the double recombinants ExF74 and FxW5093. FIG. 1B shows that a BAC clone 100B10 was identified by screening three soybean BAC libraries (HindIII, EcoRI and BamHI BAC libraries; Meksem et al., 2000) using a GmSHMT probe. The BAC clone 100B10 encompasses the markers LRR-RLK, SHMT and partial sequence of GmSHMT (the first two exons and part of the $2^{nd}$ intron). FIG. 1C shows a gene model for the GmSHMT genomic DNA sequence. The gene is 2189 bp from start codon to stop codon and contains three exons (boxes) and two introns (solid black lines). The numbers above the solid black lines indicate the nucleotide position relative to the first nucleotide of the start codon. Comparison of the GmSHMT gene sequences between Forrest and Essex identified three SNPs (G389C, T1165A and G1473C) and two InDels (at position −1384C and −1385T). FIG. 1D shows comparison of the predicted GmSHMT protein sequence between Forrest and Essex (SEQ ID NO: 2) with the amino acids differences (R130P and Y358N) highlighted.

FIG. 2A shows an EMS-mutagenized population of soybean cv. Forrest was used to screen for mutations in GmSHMT by TILLING. The gene was divided into 3 TILLING intervals (1, 2 and 3) for screening. Two missense mutants, F6266 (E61K) and F6756 (M125I), were identified. FIG. 2B shows an amino acid alignment of GmSHMT sequences including the resistant wild type allele from Forrest (SEQ ID NOs: 99-101), the resistant allele from the donor parent PI548402 (Peking) (SEQ ID NOs: 102-104), the F6266 (SEQ ID NO: 105) and F6756 SEQ ID NO: 106) Forrest mutant alleles, and the susceptible alleles from cultivars Essex (SEQ ID NO: 2) and Williams 82 (SEQ ID NOs: 107-109). The numbers above the alignment correspond to the amino acid position within the Forrest GmSHMT protein sequence. The arrows denote the position of two amino acids that differ between SCN resistant and susceptible lines (R130P and Y358N) and the position of the mutations in the two new Forrest alleles (E61K and M125I) induced by EMS. FIG. 2C shows a SCN phenotype of the GmSHMT TILLING mutants. Compared to the SCN resistant cv. Forrest (wild type) and the SCN susceptible cv. Essex, both the E61K and M125I mutations produced a shift from resistant to moderately susceptible (FI≥20% in homozygote mutant lines) and from resistant (FI≤10%) to moderately resistant (FI between 10-20% in heterozygote mutant lines).

FIG. 4 is a series of graphs and images demonstrating the functional validation of GmSHMT by VIGS, RNAi and complementation. FIG. 4A shows SCN reproduction in soybean roots silenced for GmSHMT using virus-induced gene silencing. Nematode reproduction was measured on SCN resistant RIL ExF67 inoculated with either BPMV (Bean pod mottle virus) or BPMV containing a fragment of the SHMT gene sequence (BPMV-SHMT) and SCN susceptible RIL ExF63 inoculated with BPMV only. Diamonds represent the number of cysts on a single root system. At least twelve plants per treatment were used. Four independent experiments were performed showing similar results. Representative data from one experiment are presented. Different letters denote a significant difference at P<0.0001. FIG. 4B shows qPCR analysis of GmSHMT transcript levels in control and GmSHMT-silenced roots. The value for GmSHMT-silenced roots represents the mean±SE of five samples, normalized relative to soybean ubiquitin and calibrated to the expression in the BPMV control sample. FIG. 4C shows SCN reproduction in soybean roots silenced for GmSHMT using RNA interference. Nematode reproduction was measured on transgenic ExF67 hairy root lines transformed with a GmSHMT RNAi construct under control of a nematode-inducible promoter, pZF (Kandoth et al., 2011; pZF-SHMTi). Transgenic ExF67 and ExF63 hairy root lines transformed with the vector containing a portion of the GUS gene (GUSi) were used as resistant and susceptible controls, respectively. At least twelve independent transgenic hairy root lines were generated per genotype treatment. Diamonds represent the number of cysts on a single hairy root line. Three independent experiments were performed showing similar results. Data from one experiment are presented. Different letters denote a significant difference at P<0.01. FIG. 4D, FIG. 4E, and FIG. 4F show GmSHMT promoter-GUS analysis in SCN resistant ExF67 (FIG. 4D and FIG. 4E) and SCN susceptible ExF63 (FIG. 4F) showing expression in syncytial feeding cells at 3 days post-inoculation with SCN (FIG. 4G) SCN reproduction on SCN susceptible ExF63 hairy root lines transformed with the a full length GmSHMT gene fragment under control of the native promoter. Transgenic ExF67 and ExF63 hairy root lines transformed with the vector containing only promoter sequence were used as resistant and susceptible controls, respectively. At least fourteen independent transgenic hairy root lines were generated per genotype treatment. Diamonds represent the number of cysts on a single hairy root. Four independent experiments were performed showing similar results. Data from one experiment are presented. Different letters denote a significant difference at P<0.001. N=nematode; Syn=syncytium. In graphs, the bars indicate the mean values.

FIG. 5 is a series of views of the computer-modeled structure of GmSHMT. FIG. 5A shows a homology model of the Essex GmSHMT homodimer showing that the corresponding Forrest mutations, P130R and N358Y are located on the surface of the dimer, whereas the position of F6266 (E61K) mutation is buried in the dimeric interaction interface and the F6756 (M125I) mutation is located in the core of each monomeric subunit. FIG. 5B shows that three of the four mutations overlap with GmSHMT ligand binding sites. The ligand binding sites are mapped on each of the two monomers forming the dimer. When two ligand binding sites overlap only the highlighted surface for one of the sites is shown. Both Forrest mutations, P130R and N358Y, overlap with the THF/MTHF/FTHF binding site and are in close proximity to the PLS and PLG binding sites. In addition, Forrest P130R is in a close proximity to one of the two glycine binding sites. The F6266 (E61K) mutation overlaps with both the THF/MTHF/FTHF and PLS binding sites and is in a close proximity to PLG binding site.

FIG. 6 depicts the sequence analysis of the GmSUB gene mapped to the Rhg4 locus. FIG. 6 shows a comparison of GmSUB cDNA and predicted protein sequences between the SCN resistant soybean cv. Forrest (F) (SEQ ID NOs: 110-113) and the SCN susceptible cvs. Essex (E) (SEQ ID NOs: 114-117) and Williams 82 (W) (SEQ ID NOs: 118-121). The nucleotide differences and the corresponding amino acid differences are boxed. An alignment of GmSUB promoter sequences from soybean cvs. Forrest, Essex, and Williams 82 identified no nucleotide differences in 1,766 bp of sequence 5' of the start codon.

FIG. 7A shows an alignment of GmSHMT promoter sequences from soybean cvs. Forrest (SEQ ID NO: 122), Essex (SEQ ID NO: 4), and Williams 82 (SEQ ID NO: 123). Nucleotide differences are highlighted.

DETAILED DESCRIPTION OF THE INVENTION

Figure 1:
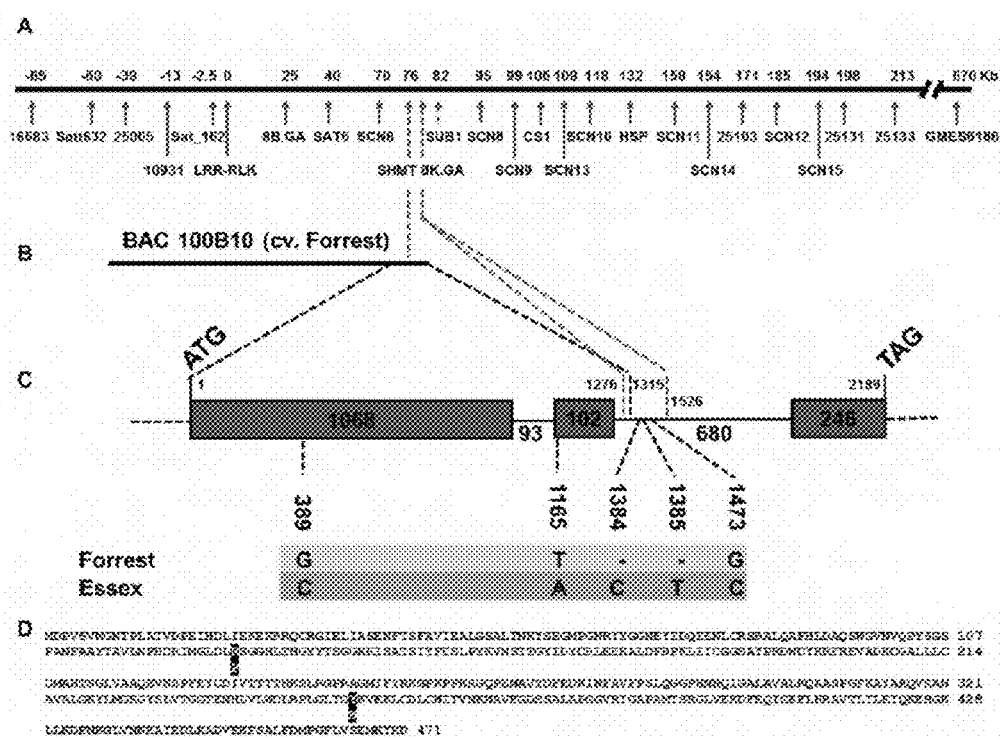
FIG. 1 is a series of drawings and a sequence listing illustrating the positional cloning of the Rhg4 gene.

The present disclosure is based, at least in part, on the discovery that a serine hydroxymethyltransferase (GmSHMT) gene mapped to the Rhg4 locus confers resistance to the soybean cyst nematode, *Heterodera glycines*. While the Rhg4 locus was previously identified as a major quantitative trait locus contributing to resistance of this pathogen, the present disclosure is the first report of map-based cloning of the gene at the Rhg4 locus responsible for conferring a resistance phenotype.

The GmSHMT gene encodes a serine hydroxymethyltransferase, an enzyme responsible for interconversion of serine and glycine and essential for one-carbon folate metabolism. As reported herein, alleles of Rhg4 conferring resistance or susceptibility differ by two genetic polymorphisms predicted to compromise folate binding affinity. Also as reported herein, two independent point mutations identified by TILLING, gene knockdown by VIGS and RNAi, and transgenic complementation of the susceptible line confirmed that the GmSHMT gene confers resistance to soybean cyst nematode.

According to the approach described herein, a soybean cell or plant can be transformed so as to provide for SCN resistance. In some embodiments, a soybean host cell or plant can be transformed with a nucleic acid molecule encoding a polypeptide having serine hydroxymethyltransferase activity. A nucleic acid encoding a polypeptide having serine hydroxymethyltransferase activity can have a substantial effect on the resistance of a plant to SCN.

Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment.

Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Transformed Organism

Provided herein is a soybean plant genetically engineered to be resistant to soybean cyst nematode (e.g., *Heterodera glycines*). The host genetically engineered to resist SCN can be any soybean plant or cell.

Assays to assess SCN resistance are well known in the art (see Examples). Except as otherwise noted herein, therefore, SCN resistance of a plant can be carried out in accordance with such assays.

One aspect of the current invention is therefore directed to the aforementioned plants and parts thereof and methods for using these plants and plant parts. The term "plant" can include plant cells, plant protoplasts, plant cells of tissue culture from which a plant can be regenerated, plant calli, plant clumps and plant cells that are intact in plants or parts of plants such as pollen, flowers, seeds, leaves, stems, and the like. Each of these terms can apply to a soybean "plant". Plant parts (e.g., soybean parts) include, but are not limited to, pollen, an ovule and a cell. The invention further provides tissue cultures of regenerable cells of these plants, which cultures regenerate soybean plants capable of expressing all the physiological and morphological characteristics of the starting variety. Such regenerable cells may include embryos, meristematic cells, pollen, leaves, roots, root tips or flowers, or protoplasts or callus derived therefrom. Also provided by the invention are soybean plants regenerated from such a tissue culture, wherein the plants are capable of expressing all the physiological and morphological characteristics of the starting plant variety from which the regenerable cells were obtained.

Such SCN resistant plants can have a commercially significant yield, for example, a yield of at least 90% to at least 110% (e.g., at least 95%, 100%, 105%) of a soybean check line. Plants are provided comprising the GmSHMT alleles and SCN resistance and a grain yield of at least about 90%, at least about 94%, at least about 98%, at least about 100%, at least about 105% or at least about 110% of these lines.

As reported herein, transformation of a SCN susceptible soybean (RIL ExF63) with a GmSHMT gene construct (2.3-kb of sequence upstream of the start through 0.57-kb downstream of the stop codon) so as to express GmSHMT within syncytia provided SCN resistance in hairy roots according to the nematode infection assays with *H. glycines*.

Further experiments showed that silencing of the GmSHMT gene in the SCN-resistant RIL ExF67 resulted in a 74% reduced GmSHMT expression in the roots of plants and a 29% increase in susceptibility to SCN. Addition of a complementary targeted RNAi gene silencing approach increased nematode reproduction on hairy roots of the SCN resistant RIL ExF67.

In various embodiments, a gene encoding a polypeptide having serine hydroxymethyltransferase activity is engineered in a host plant (e.g., a soybean plant) so as to result in an SCN resistant phenotype. In some embodiments, the gene encoding a polypeptide having serine hydroxymethyltransferase activity is expressed in the host plant. In some embodiments, the gene encoding a polypeptide having serine hydroxymethyltransferase activity is overexpressed in the host plant.

A gene encoding a polypeptide having serine hydroxymethyltransferase activity can be endogenous or exogenous to the host plant. Transformation of a plant to express polypeptide having serine hydroxymethyltransferase activity can convey SCN resistance to a host lacking such phenotype. Transformation of a plant to express polypeptide having serine hydroxymethyltransferase activity can increase SCN resistance to a host already possessing such phenotype.

A transformed plant or plant cell can be analyzed for the presence of a gene of interest and the expression level or profile conferred by the construct of the present disclosure. Those of skill in the art are aware of the numerous methods available for the analysis of transformed hosts. For example, methods for host analysis include, but are not limited to Southern blots or northern blots, PCR-based approaches, biochemical analyses, phenotypic screening methods, and immunodiagnostic assays.

In some embodiments, a host plant transformed to express a polypeptide having serine hydroxymethyltransferase activity can exhibit at least about 10% decrease in susceptibility to SCN. For example, a host plant transformed to express a polypeptide having serine hydroxymethyltransferase activity can exhibit at least about 20%, at least about 30%, at least about 40%, at least about 50%, at least about 60%, at least about 70%, at least about 80%, at least about 90%, or at least about 100% decrease in susceptibility to SCN as compared to a non-transformed control. As another example, a host plant transformed to express a polypeptide having serine hydroxymethyltransferase activity can exhibit at least about 100%, at least about 200%, at least about 300%, at least about 400%, at least about 500%, at least about 600%, at least about 700%, at least about 800%, at least about 900%, or at least about 1000% decrease in susceptibility to SCN as compared to a non-transformed control.

A gene of particular interest for engineering a soybean plant to exhibit SCN resistance is GmSHMT (SEQ ID NO: 1). As described herein, GmSHMT has been mapped to the Rhg4 locus and confers resistance to the soybean cyst nematode, *Heterodera glycines*.

In some embodiments, a transformed host soybean plant comprises an GmSHMT polynucleotide of SEQ ID NO: 1, or a functional fragment thereof. In some embodiments, a transformed host soybean plant comprises an GmSHMT polynucleotide of SEQ ID NO: 3, or a functional fragment thereof. In some embodiments, a soybean plant is transformed with a nucleotide sequence encoding GmSHMT polypeptide of SEQ ID NO: 2, or a functional fragment thereof.

In further embodiments, a transformed host soybean plant comprises a nucleotide sequence having at least about 80% sequence identity to a GmSHMT polynucleotide of SEQ ID NO: 1 or SEQ ID NO: 3, or a functional fragment thereof, or a nucleotide sequence encoding a polypeptide having serine hydroxymethyltransferase activity and at least about 80% sequence identity to the GmSHMT polypeptide SEQ ID NO: 2, or a functional fragment thereof. As an example, a transformed host soybean plant can comprise a nucleotide sequence having at least about 85%, at least about 90%, at least about 95%, or at least about 99% sequence identity to a GmSHMT polynucleotide of SEQ ID NO: 1 or SEQ ID NO: 3, or a functional fragment thereof, wherein the transformed soybean exhibits SCN resistance or serine hydroxymethyltransferase activity. As an example, a transformed soybean can comprise a nucleotide sequence encoding a polypeptide having at least about 85%, at least about 90%, at least about 95%, or at least about 99% sequence identity to a GmSHMT polypeptide of SEQ ID NO: 2, or a functional fragment thereof, wherein the transformed soybean exhibits SCN resistance or serine hydroxymethyltransferase activity.

As another example, a transformed soybean can comprise a nucleotide sequence that hybridizes under stringent conditions to a GmSHMT polynucleotide of SEQ ID NO: 1 or SEQ ID NO: 3 over the entire length of SEQ ID NO: 1 or SEQ ID NO: 3, respectively, or a functional fragment thereof, and which encodes a polypeptide having serine hydroxymethyltransferase activity.

As a further example, a transformed soybean can comprise the complement to any of the above sequences.

Variant Sequences

As describe above, a plant can be transformed with a variant of the GmSHMT polynucleotide SEQ ID NO: 1 or SEQ ID NO: 3 or with a polynucleotide encoding a variant of the GmSHMT polypeptide SEQ ID NO: 2. The species of SEQ ID NO: 1, SEQ ID NO: 3, and SEQ ID NO: 2 are representative of the genus of variant nucleic acid and polypeptides, respectively, because all variants must possess the specified catalytic activity (e.g., serine hydroxymethyltransferase activity) and must have the percent identity required above to the reference sequence.

Furthermore, the present disclosure provides guidance as to regions of the sequences important to activity.

As reported herein, genomic DNA sequences of GmSHMT from Forrest and Essex showed 5 nucleotides differences (3 SNPs and 2 Ins/Dels) between the resistant and susceptible alleles. Two of the nucleotide differences found between the Forrest and Essex GmSHMT cDNAs resulted in an amino acid change in the predicted protein sequences (R130P and Y358N). The amino acid sequence at these two positions in Williams 82 was consistent with that of Essex.

Also reported herein are two mutations in the GmSHMT gene on chromosome 8 that lead to missense mutations at E61K and M125I. SIFT predictions were performed on both mutations. Based on SIFT predictions (i.e., whether an amino acid substitution affects protein function based on sequence homology and the physical properties of amino acids), the M125I mutation was predicted to be deleterious to the protein and both mutants were more susceptible to SCN in nematode infection assays. Additionally, the F6756 (M125I) mutation was correlated with the SCN resistance phenotype of individual plants.

Based on SCN female index score and SNP-based GmSHMT haplotype, 13 polymorphisms were identified in the coding regions and 6 in the non coding DNA sequences. Two coding polymorphisms, R130P and Y358N substitutions, were shown to produce amino acid changes responsible for the "Peking type resistance" SCN phenotype. Eight different GmSHMT haplotypes were identified.

Homology modeling of the structure of GmSHMT provides guidance as to how variant genotypes affect structural and functional properties. Mapping of ligand binding sites of SHMT homologs onto the surface of a GmSHMT model identified five putative binding sites, including two glycine ($GS_1$ and $GS_2$), one PLP-serine (PLS), one PLP-glycine (PLG), and one THF/MTHF/5-formylTHF (FTHF) binding site, with the latter three binding sites physically co-localized in the binding pocket formed by the SHMT dimer molecule. Both Forrest mutations and TILLING mutation F6266 E61K were shown to be in close proximity to the tentative ligand binding sites.

Forrest mutations P130R and N358Y were co-localized with the THF/MTHF/FTHF binding site and in close proximity to PLS, PLG and one of the two glycine binding sites. The position of the F6266 E61K mutation overlapped with the PLS and THF/MTHF/FTHF binding sites. Thus, the three mutations may directly affect the reversible interconversion of L-serine and THF to glycine and MTHF. TILLING mutation F6756 M125I was shown to be in an interior beta sheet, suggesting structural instability of the GmSHMT region affected by the TILLING mutation.

Variant polynucleic acid molecules and corresponding encoded polypeptides discussed herein can contain one or more of the above described mutations.

Thus is provided guidance as to regions of the sequences important to activity.

Promoters

One or more of the nucleotide sequences discussed above (e.g., GmSHMT or a variant thereof) can be operably linked to a promoter that can function in a plant, such as soybean. Promoter selection can allow expression of a desired gene product under a variety of conditions.

Promoters can be selected for optimal function in a soybean host cell into which the vector construct will be inserted. Promoters can also be selected on the basis of their regulatory features. Examples of such features include enhancement of transcriptional activity and inducibility.

Numerous promoters functional in a soybean plant will be known to one of skill in the art (see e.g., Weise et al. Applied Microbiology and Biotechnology 70(3), 337-345; Saidi et al. 2005 Plant Molecular Biology 59(5), 697-711; Horstmann et al. 2004 BMC Biotechnology 4; Holtorf et al. 2002 Plant Cell Reports 21(4), 341-346; Zeidler et al. 1996 Plant Molecular Biology 30(1), 199-205). Except as otherwise noted herein, therefore, the processes and compositions of the present disclosure can be carried out in accordance with such known promoters. Examples of promoters than can be used in accord with methods and compositions described herein include, but are not limited to, factor EF1α gene promoter (US App Pub No. 2008/0313776); rice tungro bacilliform virus (RTBV) gene promoter (US App Pub No. 2008/0282431); cestrum yellow leaf curling virus (CmYLCV) promoter (Stavolone et al. Plant Molecular Biology 53(5), 663-673); tCUP cryptic promoter system (Malik et al. 2002 Theoretical and Applied Genetics 105(4), 505-514); T6P-3 promoter (JP2002238564); S-adenosyl-L-methionine synthetase promoter (WO/2000/037662); Raspberry E4 gene promoter (U.S. Pat. No. 6,054,635); cauliflower mosaic virus 35S promoter (Benfey et al. 1990 Science 250(4983), 959-966); figwort mosaic virus promoter (U.S. Pat. No. 5,378,619); conditional heat-shock promoter (Saidi et al. 2005 Plant Molecular Biology 59(5), 697-711); promoter subfragments of the sugar beet V-type H+-ATPase subunit c isoform (Holtorf et al. 2002 Plant Cell Reports 21(4), 341-346); beta-tubulin promoter (Jost et al. 2005 Current Genetics 47(2), 111-120); and bacterial quorum-sensing components (You et al. 2006 Plant Physiology 140 (4), 1205-1212).

The promoter can be an inducible promoter. For example, the promoter can be induced according to temperature, pH, a hormone, a metabolite (e.g., lactose, mannitol, an amino acid), light (e.g., wavelength specific), osmotic potential (e.g., salt induced), a heavy metal, or an antibiotic. In some embodiments, the promoter comprises a nematode-inducible promoter (e.g., Glyma15g04570.1, see Example 8). Numerous standard inducible promoters will be known to one of skill in the art.

The promoter can be a tissue-specific promoter. For example, a transcribable nucleic acid molecule described herein can be operably linked to a pollen-, flower-, seed-, leaf-, or stem-specific promoter. As another example, a transcribable nucleic acid molecule described herein can be operably linked to a seed-specific promoter. For example, the promoter can be a root-specific promoter. Numerous standard tissue-specific promoters will be known to one of skill in the art.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

The promoter can be any promoter endogenously associated with SHMT, or a variant thereof. In some embodiments, the promoter can comprises SEQ ID NO: 4, which is the native Essex Gm08-A2 SHMT promoter. In other embodiments, the promoter can comprise a variant of SEQ ID NO: 4 having at least about 80% identity thereto (e.g., at least about 85%, at least about 90%, at least about 95%, at least about 99%) and retaining promoter function.

Inclusion of a termination region control sequence is optional, and if employed, then the choice is be primarily one of convenience, as the termination region is relatively interchangeable. The termination region may be native to the transcriptional initiation region (the promoter), may be native to the nucleic acid sequence of interest, or may be obtainable from another source.

A promoter of the present disclosure can be incorporated into a construct using marker genes as described and tested for an indication of gene expression in a stable host system. As used herein the term "marker gene" refers to any transcribable nucleic acid molecule whose expression can be screened for or scored in some way.

Constructs

Any of the transcribable polynucleotide molecule sequences described above can be provided in a construct. Constructs of the present invention generally include a promoter functional in the host plant, such as soybean, operably linked to a transcribable polynucleotide molecule encoding a polypeptide with serine hydroxymethyltransferase activity (e.g., GmSHMT), such as provided in SEQ ID NO: 1, and variants thereof as discussed above.

Exemplary promoters are discussed above. One or more additional promoters may also be provided in the recombinant construct. These promoters can be operably linked to any of the transcribable polynucleotide molecule sequences described above.

The term "construct" is understood to refer to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. The term "vector" or "vector construct" is understood to refer to any recombinant polynucleotide construct that may be used for the purpose of transformation, i.e., the introduction of heterologous DNA into a host plant, such as a soybean.

In addition, constructs may include, but are not limited to, additional polynucleotide molecules from an untranslated region of the gene of interest. These additional polynucleotide molecules can be derived from a source that is native or heterologous with respect to the other elements present in the construct.

Host cells developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Molecular Engineering

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the gmSHMT sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[Na$^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Breeding

The present disclosure provides genetic markers and methods for the introduction of GmSHMT alleles into agronomically elite soybean plants. The invention therefore allows the creation of plants that combine these GmSHMT alleles that confer SCN resistance with a commercially significant yield and an agronomically elite genetic background. Using the methods of the invention, loci conferring the SCN phenotype may be introduced into a desired soybean genetic background, for example, in the production of new varieties with commercially significant yield and SCN resistance.

Marker assisted introgression involves the transfer of a chromosome region defined by one or more markers from one germplasm to a second germplasm. The initial step in that process is the localization of the trait by gene mapping, which is the process of determining the position of a gene relative to other genes and genetic markers through linkage analysis. The basic principle for linkage mapping is that the closer together two genes are on the chromosome, the more likely they are to be inherited together. Briefly, a cross is generally made between two genetically compatible but divergent parents relative to traits under study. Genetic markers can then be used to follow the segregation of traits under study in the progeny from the cross, often a backcross (BC1), $F_2$, or recombinant inbred population.

The term quantitative trait loci, or QTL, is used to describe regions of a genome showing quantitative or additive effects upon a phenotype. The Rhg4 loci, containing GmSHMT alleles, represent exemplary QTL because GmSHMT alleles result in SCN resistance. Herein identified are genetic markers for non-transgenic, GmSHMT alleles that enable breeding of soybean plants comprising the GmSHMT alleles with agronomically superior plants, and selection of progeny that inherited the mutant GmSHMT alleles. Thus, the invention allows the use of molecular tools to combine these QTLs with desired agronomic characteristics.

Processes for marker assisted breeding are well known in the art. Except as otherwise noted herein, therefore, the process of the present disclosure can be carried out in accordance with such processes.

Research Tool

The SHMT gene can be used to find or characterize related (interactive) genes or identify or further characterize the cascade for SCN resistance. The discovery of a SHMT as part of the resistance signaling pathway against SCN provides novel insight into this complex host-pathogen interaction. Insights reported herein can be used to discern the relationship between SHMT and metabolism.

In some embodiments, the SHMT gene can be used in a genomics, proteomics, bioinformatics, or statistical modeling approach to fish or isolate candidate genes or encoded proteins or other molecules with a direct or indirect function in mediating disease resistance to SCN in soybeans. In some embodiments, the SHMT gene can be used in a genomics, proteomics, bioinformatics, or statistical modeling approach to fish or isolate candidate genes or encoded proteins or other molecules with a direct or indirect function in mediating compatible or incompatible responses of soybeans to SCN (e.g., to a nematode or any intermediate). Thus is provided various methods to find or characterize related (interactive) genes involved with SCN resistance.

With the exception of Hs1$^{pro-1}$, a gene for *H. schachtii* resistance in sugar beet that encodes a 282-aa transmembrane protein with imperfect leucine-rich repeats (Cai et al., 1997), all other genes for nematode resistance identified to date belong to the canonical NB-LRR (nucleotide binding site, leucine-rich repeat) class of plant resistance genes (Milligan et al., 1998; van der Vossin et al., 2000; Ernst et al., 2002; Paal et al., 2004). Conversely, SHMT is a metabolic enzyme with a key role in one-carbon folate metabolism. Although the enzyme has multiple catalytic activities, one of its main roles is to catalyze the reversible conversion of serine and tetrahydrofolate (THF) to glycine and 5,10-methyleneTHF (MTHF) to supply one-carbon units for de novo purine, thymidylate, and methionine synthesis underlying its importance in DNA synthesis and cellular methylation reactions.

SHMT is a ubiquitous enzyme in nature that is structurally conserved across kingdoms. With the exception of a mung bean SHMT (Sukanya et al., 1991), all other SHMTs characterized to date require pyridoxal 5'-phosphate (PLP), the active form of vitamin B6. The 3-D structures of SHMT from a variety of organisms including humans, rabbit, mouse, and *E. coli* have been determined (Renwick et al., 1998; Scarsdale et al, 2000). Dimeric SHMTs are mainly found in prokaryotes, while eukaryotic SHMTs form a dimer of dimers.

*Arabidopsis* has seven SHMT family members that encode predicted mitochondrial, plastid or cytoplasmic localized enzymes which exhibit organ-specific expression patterns during plant development (McClung et al., 2000; Moreno et al., 2004). SHMT1 is highly expressed in leaves, stems and flowers, and is undetectable in roots, consistent with its role as a photorespiratory mitochondrial family member (Moreno et al., 2004). In mitochondria, glycine is decarboxylated by the glycine decarboxylase complex (GDC) to form MTHF. SHMT1 then transfers a one-carbon unit from MTHF to glycine for the production of serine which gets recycled into the chloroplast Calvin cycle. *Arabidopsis* plants harboring a null allele in SHMT1 are dwarf and chlorotic and die before producing progeny. Additionally, an *Arabidopsis* EMS mutant exhibiting reduced SHMT1 activity were not able to mount an efficient defense response to limit invasion by biotrophic and necrotrophic foliar pathogens, highlighting the importance of the photorespiratory pathway in plant resistance to pathogens. The role of plant cytosolic SHMTs and one-carbon flux in the cytoplasm, however, is not well understood. It is also not known how alterations in one-carbon flux in one compartment may influence one-carbon flux in other compartments. The compartmentalization of nucleotide synthesis in the plastids and mitochondria of plants suggests that one-carbon flux in the cytoplasm may be biased toward the re-methylation of homocysteine to methionine and highly active in cells types actively producing methylated compounds such as lignins and alkaloids (Christensen and MacKenzie, 2006).

Within a few days after establishment, feeding cells induced in plants carrying Rhg genes began to degenerate by what has been described as a hypersensitive response (HR), a form of localized programmed cell death (PCD) in plants to ward off invading pathogens. The mechanism could be attributed to the plant activating HR-like PCD to kill the feeding cell causing the nematode to starve and die or the nematode death occurs prior to activation of HR-like PCD. Localized necrosis at the feeding site in response to SCN is a common theme among resistant soybean cultivars, but the timing of necrosis and the degeneration of syncytia vary depending on the source of resistance (Acedo et al., 1984). Extensive histological studies have documented the cellular changes associated with degenerating syncytia in soybean, including the deposition of secondary cell wall material and formation of lipid-like globules (Endo, 1965; Riggs et al., 1973; Acedo et al., 1984). Comparative analyses of syncytia transcriptional profiles in resistant and susceptible soybean have identified increased defense-related gene expression associated with apoptotic cell death and the plant hypersensitive response in syncytia formed in resistant plants (Kandoth et al., 2011).

A biochemical analysis of the Essex and Forrest SHMTs can be used to determine more specifically how the observed amino acid differences may be altering GmSHMT function to contribute to resistance against SCN. The evidence herein suggests that altered folate metabolism is likely a contributing factor in soybean resistance to SCN, providing new insight into the molecular basis of this agronomically important pathosystem.

Active Organism Suppression

Folate (vitamin B) is critical for nematode health. If expression of the SHMT or its regulation is impacting the folate pathway in a plant tissue, then it may impact a nematode feeding on that plant tissue. It is hypothesized that a nematode may acquire folate or a precursor or derivative thereof from the soybean plant itself. It is further hypothesized that the SHMT gene or gene product may interfere with the nematode's folate pathway.

In humans, mutations in SHMT have been linked with a wide range of disease states including adult lymphocytic leukemia (Skibola et al., 2002), cardiovascular disease (Lim et al, 2005), and neural tube defects (Heil et al., 2001). This is not surprising considering the importance of SHMT in supplying one-carbon units for multiple folate pathways. A reduction in the availability of one-carbon units as a result of altered SHMT protein expression, stability, or activity could mimic a folate deficiency. Folate is essential for the maintenance of DNA integrity and stability and a cellular deficiency in this important B vitamin can lead to an imbalance of DNA precursors and altered DNA synthesis and repair. Consequently, folate deficiency has been shown to mediate a variety of malignancies (Kim, 2003). Under folate sufficient conditions, thymidylate synthase utilizes MTHF as a methyl donor to convert dUMP (deoxyuridylate monophosphate) to the pyrimidine nucleotide dTMP (deoxythymidylate monophosphate). However, if MTHF is limited under folate deficient conditions this reaction is blocked and increased dUMP levels lead to uracil misincorporation into DNA resulting in strand breaks and chromosomal aberrations. Such cellular alterations have been shown to induce apoptosis in mammals (Novakovic et al., 2006). Folate deficiency can also alter normal DNA methylation. Low levels of MTHF lead to a reduction in availability of 5-methylTHF required for homocysteine conversion into methionine. Reductions in methionine deplete the pool of S-adenosylmethionine which results in hypomethylation of DNA and other cellular compounds, leading to improper gene expression and other cellular abnormalities.

The role of SHMTs and one-carbon folate metabolism in plants is much less characterized than in yeast and mammals, nonetheless significant differences among these organisms have been recognized (reviewed in Christensen and MacKenzie, 2006). In yeast and mammals, one-carbon folate metabolism is divided between the mitochondrial and cytoplasmic compartments. In contrast, one-carbon folate metabolism is divided among the cytoplasmic, plastid, and mitochondrial compartments in plants. Consistent with this compartmentalization, cytoplasmic, mitochondrial and plastid isoforms of one-carbon folate enzymes, including SHMT, have been identified. These observations suggest that there are likely to be differences in the metabolic roles of these enzymes, as well as one-carbon flux among these organisms.

The GmSHMT identified and demonstrated herein to play a role in soybean resistance to SCN is predicted to be a cytosolic enzyme. LCM-microarray analysis of developing syncytia (Ithal et al., 2007) and the promoter-GUS analyses described herein indicate that GmSHMT is upregulated in feeding cells formed in SCN-susceptible soybean cultivars. The feeding cells induced by cyst nematode undergo dramatic changes in gene expression, organelles proliferate, and they become metabolically highly active nutrient sinks. Syncytia contain multiple large and amoeboid nuclei as a consequence of repeated rounds of DNA synthesis (i.e., endoreduplication) in the absence of mitosis and it has been demonstrated that blocking DNA synthesis negatively affects the establishment and development of syncytia (de Almeida Engler et al., 2011). Transcriptional and metabolic profiling studies of syncytia support increased rates of amino acid, DNA, and secondary cell wall biosynthesis (Ithal et al., 2007; Hofmann et al., 2010). Thus, one might predict a high demand on folate one-carbon metabolism for syncytium development and maintenance.

Computational analysis predicted that the mutations in Forrest SHMT may negatively impact its activity, which could ultimately lead to folate deficiency, especially in a cell type with a higher demand for one-carbon metabolism. The nematode's nutritional requirements may also be influencing folate metabolism in developing syncytia. Although the nutritional requirements of plant-parasitic nematodes are not well defined, it is assumed that like other animals, they acquire folate from their diet. Folate deficiency, which has been shown to induce apoptosis in mammalian cells (Novakovic et al., 2006), may ultimately lead to HR-like PCD or nematode starvation. The ability, however, to restore resistance in a genetic background containing a functional Essex GmSHMT by transformation of a full length genomic clone corresponding to the Forrest GmSHMT resistance allele, also supports a model wherein a host-pathogen recognition event must occur for resistance to be triggered.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Haplotyping of Plant Introductions (PIs) at Rhg4 and Rhg1 Loci

A total of 81 soybean lines (plant introductions, landraces and elite cultivars) were scored for their SCN phenotype and SNP-genotyped at the rhg1 and Rhg4 loci. Lines were classified resistant (R) to SCN if the FI was ≤10% and susceptible (S) if the FI was ≥10%. Soybean lines were genotyped at the Rhg4 locus using the DNA markers Sat_162, SHMT and SUB1 and at the rhg1 locus using the DNA markers 560, 570 and Satt309 (see e.g., TABLE 1).

TABLE 1

| | Haplotyping of plant introductions (PIs) at Rhg4 and rhg1 loci | | | | | |
|---|---|---|---|---|---|---|
| | SCN Infection | Rhg 4 Locus | | rhg 1 Locus | | |
| PI Name | phenotype | Sat_162 | SUB1 | 560 | 570 | Satt309 |
| PI 90406 | S | S | S | | | R |
| PI 59845 | S | S | S | | | R |
| PI 594788 | S | S | 5 | | | R |
| PI 594829 | S | S | S | | | R |
| PI 603521 | S | S | S | | | S |
| PI 603596 | S | S | S | | | R |
| PI 408342 | S | S | S | | | S |
| PI 594871 | S | $ | S | | | R |
| PI 594562 A | S | S | S | | | S |
| PI 594707 | S | S | S | | | R |
| PI 603428 C | S | R | R | S | S | R |
| PI 587849 | S | S | S | | | S |
| PI 602991 | S | R | R | S | S | S |
| PI 567503 | S | S | S | | | S |
| PI 603698 G | S | S | S | | | R |
| PI 594451 | S | S | s | | | R |
| PI 603516 | S | S | S | | | S |
| PI 587752 | S | S | S | | | R |
| PI 594770 A | S | R | R | S | S | R |
| PI 603785 | S | S | S | | | S |
| PI 603424 A | S | S | S | | | S |
| PI 594777 | S | S | S | | | R |
| PI 603502 A | S | S | S | s | S | R |
| PI 603318 | S | S | S | | | S |
| PI 603384 | S | S | S | R | R | S |
| PI 603712 | S | S | S | | | S |
| PI 588040 | S | S | S | | | R |
| PI 587666 | 5 | 8 | S | | | S |
| PI 567359 | S | R | R | S | 3 | R |
| PI 587799 | S | S | S | | | S |
| PI 603704 A | S | S | S | | | R |
| PI 567368 | S | S | S | S | S | R |
| PI 603420 | S | R | R | S | S | R |
| PI 587993 | S | S | S | S | S | S |
| PI 407801 | S | S | S | | | S |
| PI 603408 | S | S | S | | | S |
| PI 587700 C | S | S | S | | | S |
| PI 587552 | S | S | S | | | R |
| PI 587823 | S | S | S | | | S |
| PI 567568 B | S | S | S | R | R | S |
| PI 603357 | S | S | S | S | S | R |
| PI 603337 B | S | S | S | | | R |
| PI 79691 | S | S | S | | | S |
| PI 567293 | S | S | S | | | S |
| PI 567364 | S | S | S | | | R |
| PI 567395 | S | S | S | | | R |
| PI 567631 | S | S | S | | | R |
| PI 86145 | S | S | S | | | S |
| PI 567481 | S | S | S | S | S | R |
| PI 567525 | S | S | S | | | S |
| PI 567700 | S | S | S | | | S |
| PI 594615 | $ | S | S | | | R |
| PI 603147 | S | S | S | | | R |
| PI 603336 | S | S | S | | | R |
| PI 603372 | S | R | R | R | R | S |
| PI 603419 B | S | S | S | | | R |
| PI 603479 | S | S | S | | | S |
| PI 603587 A | R | R | R | R | R | S |
| PI 603656 | S | R | R | S | S | S |
| PI 603675 | S | S | S | | | R |
| PI 603756 | S | S | S | | | R |
| PI 603784 | S | S | S | | | R |
| PI 97094 | S | S | S | R | R | R |
| PI 228056 | S | S | S | | | R |
| PI 594773 | $ | R | R | S | S | R |
| PI 588000 | S | S | S | | | S |
| PI 588047 | S | S | S | | | R |
| PI 594554 | S | S | S | | | S |
| PI 594597 | S | S | S | | | S |
| PI 416937 | S | S | S | | | R |
| RESSEQ | R | R | R | R | R | R |
| Essex | S | S | S | S | S | S |
| Forrest | R | R | R | R | R | R |
| Willams 82 | S | S | S | S | S | S |
| PI 548402 (Peking) | R | R | R | R | R | R |
| PI 88788 | R | R | R | R | S | S |
| PI 90763 | R | R | R | R | R | R |

TABLE 1-continued

Haplotyping of plant introductions (PIs) at Rhg4 and rhg1 loci

| PI Name | SCN Infection phenotype | Rhg 4 Locus | | rhg 1 Locus | | |
|---|---|---|---|---|---|---|
| | | Sat_162 | SUB1 | 560 | 570 | Satt309 |
| PI 437654 | R | R | R | R | R | R |
| PI 209332 | R | S | S | R | R | S |
| PI 89772 | R | R | R | R | R | R |
| PI 548316 (Cloud) | R | R | R | R | S | S |

Example 2

Primers

References are listed below for primers described herein. I. Primers for the initial screening of Rhg4 recombinants; II. Primers for high resolution genetic mapping of Rhg4 recombinants and haplotyping of plant introductions (PIs); III. Primers for TILLING, SHMT cloning, and sequencing and IV. Primers for promoter cloning, complementation, RNAi, VIGS and qPCR

TABLE 2

Primers.

| Primers Name | Forward Primer | Reverse Primer | Annealing Temp | Comments |
|---|---|---|---|---|
| I. Primers for screening of Rhg4 recombinants | | | | |
| Satt632 [4] | GGGCTATGAAGGGAAT GGAAAGGA [SEQ ID NO.: 5] | CCCATATTGAAGATTT GAAGTAAT [SEQ ID NO.: 6] | 50 | For Rhg4 |
| Sat_162 [4] | GCGTGGTTTTTCGCTG GATAT [SEQ ID NO.: 7] | GCGCATTTCGTAACAT ATTTTTCAC [SEQ ID NO.: 8] | 50 | |
| GMES6186 [3] | AGCGGGAATTGAAGGT TTTT [SEQ ID NO.: 9] | GGAATCTCATCTGAAA ATAATGGA [SEQ ID NO.: 10] | 50 | |
| Sat_210 [4] | GCGCCAGCAACAAAGT TCCTGACAAA [SEQ ID NO.: 11] | GCGCATGCAAATGAAA TAATAA [SEQ ID NO.: 12] | 50 | For rhg4 |
| Satt309 [4] | GCGCCTTCAAATTGGC GTCTT [SEQ ID NO.: 13] | GCGCCTTAAATAAAAC CCGAAACT [SEQ ID NO.: 14] | 50 | |
| SIUC-SAT143 | TGTTACTTAGTAATTA TGAAG [SEQ ID NO.: 15] | AATAATGATTTGTTGA TCGAT [SEQ ID NO.: 16] | 50 | |
| II. Primers for high resolution genetic mapping of Rhg4 recombinants and haplotyping of soybean lines | | | | |
| 16683 [2] | GCGAAGCCCATACTCC GAACCTGCCA [SEQ ID NO.: 17] | GCCTCCAAAAACTCAA CCCCATCAA [SEQ ID NO.: 18] | 58 | For Rhg4 |
| Satt632 [2] | GGGCTATGAAGGGAAT GGAAAGGA [SEQ ID NO.: 19] | CCCATATTGAAGATTT GAAGTAAT [SEQ ID NO.: 20] | 50 | |
| 25005 [2] | GATGCCTTACGCCTGT CACTAAC [SEQ ID NO.: 21] | GCAGAACAGTAGAACA AGTCCAGT [SEQ ID NO.: 22] | 58 | |
| 10931 [2] | GCCCACCAGTTGTTGT GTAAGAC [SEQ ID NO.: 23] | GCGTGCGATGAGAAAC TCAGAC [SEQ ID NO.: 24] | 60 | |
| Sat_162 [4] | GCGTGGTTTTTCGCTG GATATA [SEQ ID NO.: 25] | GCGCATTTCGTAACAT ATTTTTCAC [SEQ ID NO.: 26] | 50 | |
| LRR-RLK [1] | GAAGTTGGTGACTGCG GAAATGC [SEQ ID NO.: 27] | TTCAATGCACCGATCC AACAAGGA [SEQ ID NO.: 28] | 65 | |
| 8B.GA | TACAAGTCAGTAATAT AACCT [SEQ ID NO.: 29] | CTGAGTAGATAGCAGT GACAT [SEQ ID NO.: 30] | 55 | |
| SAT6 | ACTGCTTATGGTTGCA GAATC [SEQ ID NO.: 31] | GAGTATGTAAATGACA TCTT [SEQ ID NO.: 32] | 55 | |
| SCN6 | TATGACTGCAGAAGTC AAGTC [SEQ ID NO.: 33] | TGACCTTGAAGAGGAG ATAGA [SEQ ID NO.: 34] | 60 | |
| SHMT | ACAACACTCTCTCTTC TCGC [SEQ ID NO.: 35] | CAGATTATGAGTTTTG GCCTG [SEQ ID NO.: 36] | 60 | |
| 8K.GA | ATTTCACTTATATAAA TATGC [SEQ ID NO.: 37] | TCTCTTTTATATGCTA CAATA [SEQ ID NO.: 38] | 55 | |

TABLE 2-continued

Primers.

| | | | | |
|---|---|---|---|---|
| SUB1 | GGTACCATCTTCCTTAGAATGG [SEQ ID NO.: 39] | TGTGGGAAAGAGACAAGAAACC [SEQ ID NO.: 40] | 60 | |
| SCN8 | TTCGTTGGCTCCCACTGCTC [SEQ ID NO.: 41] | TCTGGTACACGTCAATGGGC [SEQ ID NO.: 42] | 60 | |
| SCN9 | ACGAAGAGATCCTGAAGGAG [SEQ ID NO.: 43] | ATTCCCAAGGGTTGGAAGGC [SEQ ID NO.: 44] | 60 | |
| SC1 | TCAAGCATTGTTTGGAGATGC [SEQ ID NO.: 45] | ACAGAAGCATTTGCAGGGCAG [SEQ ID NO.: 46] | 60 | |
| SCN13 | ACCTTCGTTGGATGCAAGGC [SEQ ID NO.: 47] | CTTGGTCCAAAATTGCGGGTC [SEQ ID NO.: 48] | 60 | |
| SCN10 | CGTGGCAATTTTTCGAAGGTAG [SEQ ID NO.: 49] | CAACTCAAAACCACATTGAGGC [SEQ ID NO.: 50] | 60 | |
| HSP1 | AGCAACACACGCAAACCAAATC [SEQ ID NO.: 51] | TGCAATTCATCCTACGGTGGC [SEQ ID NO.: 52] | 60 | |
| SCN11 | TCAGGACATGTTTGTTGGTGG [SEQ ID NO.: 53] | CACACTCAGTTCAGCTTATAG [SEQ ID NO.: 54] | 60 | |
| SCN14 | ATACGTGGGCCCAACTAAGAC [SEQ ID NO.: 55] | TGTCGTCTTAGGTGAGAGGC [SEQ ID NO.: 56] | 60 | |
| 25103[(2)] | TGGCTGTTCCTAGAAGGCTGTG [SEQ ID NO.: 57] | TGGAGTTGGATCGGAGGATTAAGG [SEQ ID NO.: 58] | 65 | |
| SCN12 | AAGGGAGACTGGATAACCATC [SEQ ID NO.: 59] | CCGCTCATTTGGTGAGTCATG [SEQ ID NO.: 60] | 60 | |
| SCN15 | ATGTGCTCGCTGTTGGTGATG [SEQ ID NO.: 61] | GCACCATGGAGGTGAAAAAATA [SEQ ID NO.: 62] | 60 | |
| 25131[(2)] | GGACGGTTCGCTGGCTAAGA [SEQ ID NO.: 63] | TCACTGCCTTCCTCTTCTTCTTCA [SEQ ID NO.: 64] | 58 | |
| 25133[(2)] | TCCACCGAGCAACTACCATATCTT [SEQ ID NO.: 65] | ACGAGCACATAGCCAGGCATTA [SEQ ID NO.: 66] | 58 | |
| Satt309[(4)] | GCGCCTTCAAATTGGCGTCTT [SEQ ID NO.: 67] | GCGCCTTAAATAAAACCCGAAACT [SEQ ID NO.: 68] | 50 | For rhg1 |
| 560 | TTACTTTTGGTCAGCATTTTGGC [SEQ ID NO.: 69] | TATTGTTGATATATTATATTGTCC [SEQ ID NO.: 70] | 55 | |
| 570 | ACCCTTTTTGCAGTATTTATGC [SEQ ID NO.: 71] | CTAGGTAACTCTTTTAGCCGTGA [SEQ ID NO.: 72] | 55 | |

IIII. Primers for TILLING, SHMT cloning, and sequencing

| | | | | |
|---|---|---|---|---|
| SHMT | ACAACACTCTCTCTTCTCGC [SEQ ID NO.: 73] | CAGATTATGAGTTTTGGCCTG [SEQ ID NO.: 74] | 60 | For TILLING 1 and sequencing. |
| SHMT2 | CAGGCCAAAACTCATAATCTG [SEQ ID NO.: 75] | CAGATTATGAGTTTTGGCCTG [SEQ ID NO.: 76] | 60 | For TILLING 2 and sequencing. |
| SHMT3 | TAATTTTGGTTGGAGAACAATG [SEQ ID NO.: 77] | CTAATCCTTGTACTTCATTTC [SEQ ID NO.: 78] | 60 | For TILLING 3 and sequencing. |
| SHMTcDNA | ATGGATCCAGTAAGCGTGTGG [SEQ ID NO.: 79] | CTAATCCTTG TACTTC ATTT CAG [SEQ ID NO.: 80] | 60 | For SHMT cDNA cloning |

TABLE 2-continued

Primers.

IV. Primers for promoter cloning, complementation, RNAI, VIGS, and qPCR

| Primers Name | Forward Primer* | Reverse Primer* | Comments |
|---|---|---|---|
| Promoting cloning | | | |
| GmSUB1 promoter | GTTAACCTTCAAGTCC CAATCTG [SEQ ID NO.: 81] | AGAAGAATTTGGAGC AGAAAGTG [SEQ ID NO.: 82] | |
| SHMT promoter-1 | AATTGAGCTCCAATGG CACCAATGCCCA [SEQ ID NO.: 83] | AATTGGTACCGAACGG TGGAAATGAATGAATG [SEQ ID NO.: 84] | |
| SHMT promoter-2 | AAAAAAGCAGGCTATC AATGGCACCAATGCCCA [SEQ ID NO.: 85] | AAGAAAGCTGGGTAGA ACGGTGGAAATGAATG AATG [SEQ ID NO.: 86] | Gateway cloning |
| attB1 and attB2 | GGGGACAAGTTTGTAC AAAAAAGCAGGCT [SEQ ID NO.: 87] | GGGGACCACTTTGTAC AAGAAAGCTGGGT [SEQ ID NO.: 88] | Gateway cloning |
| gDNA construct for complementation | | | |
| gSHMT-5' | AATTGGCGCGCCTGCAG GCAATGGCACCAATGCC CA [SEQ ID NO.: 89] | AATTGAGCTCGATTCC GCGGCA [SEQ ID NO.: 90] | Fragment 1 (5') cloning |
| gSHMT-3' | AATTGAGCTCATCGCCT CCGAGA [SEQ ID NO.: 91] | AATTGGTACCTGCAGG CCAGATTTTATGGTGC CCAA [SEQ ID NO.: 92] | Fragment 2 (3') cloning |
| RNAI cloning | | | |
| SHMT-Ri | AAAAAAGCAGGCTATTA CGGCGGCAATGAATACAT [SEQ ID NO.: 93] | AAGAAAGCTGGGTACT GAAGTCTAGGGCTTTT TCT [SEQ ID NO.: 94] | Gateway cloning |
| VIGS cloning | | | |
| SHMT-VIGS | ATGCGGATTCGGCAAT GAATACATCGACCAG [SEQ ID NO.: 95] | TTGGGTACCTGTCTAG GGCTTTTTCTTCCAAG [SEQ ID NO.: 96] | |
| qPCR primers | | | |
| qSHMT | TGAAAAAGACTTTGAG CAGATTGG [SEQ ID NO.: 97] | TTGCCATGCTCCTTCT GGAT [SEQ ID NO.: 98] | |

*Restriction sites/recombination sites are underlined
References:
[1] Liu et al. Functional and Integrative Genomics, 2011, 11: 539-549
[2] Hyten et al. Genetics, 2007, 175: 1937-1944
[3] Hwang et al. DNA Research, 2009, 16: 213-225
[4] http://soybase.org Example 3

Nematode and Plant Material

The SCN (*Heterodera glycines* 'Ichinohe') inbred population PA3 (Hg type 0) used was mass-selected on soybean cv. Williams 82 according to standard procedures (Niblack et al., 1993) at the University of Missouri. The soybean cultivar Forrest (Hartwig and Epps, 1973) is resistant to SCN PA3. The soybean cultivars Essex (Smith and Camper, 1973) and Williams 82 (Bernard and Cremeens, 1988) are susceptible to SCN PA3. Forrest was used to develop an ethylmethane sulphonate (EMS)-mutagenized M2 population of 2,000 lines for TILLING. The two F2:6 RIL lines, ExF67 (rhg1$_F$rhg1$_F$Rhg4$_F$Rhg4$_F$) and ExF63 (rhg1$_F$rhg1$_F$Rhg4$_E$Rhg4$_E$), are resistant and susceptible to PA3, respectively. These two RIL lines differed at the majority of markers assigned to the Rhg4 region and appeared to be nearly opposite recombination events. The collection of plant introductions used in this study was obtained from Dr. Randal Nelson, USDA Soybean Germplasm curator, UI, Urbana, Ill.

Example 4

Map-based Positional Cloning of the Rhg4 Gene

Three genetic populations segregating for resistance to SCN PA3 (Hg type 0) were used for mapping. These included an F2:6 recombinant inbred line (RIL) population from a cross between Forrest and Essex (98 individuals; Meksem et al., 2001), and two large F2 populations generated from crosses between Forrest and either Essex (1,755 lines) or Williams 82 (2,060 lines), to enrich the chromosomal interval carrying the Rhg4 gene with recombinants. SCN phenotyping was conducted according to Brown et al. (2010).

Because Forrest resistance to SCN requires both rhg1 and Rhg4 (Meksem et al., 2001), genotyping was conducted using DNA markers flanking both loci to detect informative recombinants at the Rhg4 locus (see e.g., TABLE 2). The SSR markers, Satt632, Sat_162 and GMES6186 (website soybase.org and Hwang et al., 2009) were used to identify chromosomal breakpoints at the Rhg4 locus. PCR amplifications were performed using DNA from individuals for each of the three genetic populations. Cycling parameters were as follows: 35 cycles of 94° C. 30 sec, 50° C. 30 sec and 72° C. 30 sec with 7 min of extension at 72° C. The PCR products were separated on 3%-4% metaphor agarose gels. The identified recombinants were subject to a second screening using SSR markers, Sat_210 and Satt309 (website soybase.org), and SIUC-SAT143 to identify the rhg1 genotype of each recombinant.

To enrich the chromosomal regions carrying the Rhg4 locus with DNA markers, the Genbank published sequences AX196297 and AX197417 were used to design PCR primers every 5 to 10 Kbp of the 300 Kbp carrying the Rhg4 locus (see e.g., TABLE 2). DNA from Forrest and Essex were tested with each primer using a modified EcoTILLING protocol to find and map polymorphic sequences at the Rhg4 locus (Meksem et al., 2008; Liu et al., 2011). The identified SNP and InDel DNA markers were integrated into the informative recombinants to identify chromosomal breakpoints and the interval that carried the Rhg4 gene.

The closest DNA markers harboring the Rhg4 locus were used to screen a Forrest BAC library (Meksem et al., 2001, Liu et al., 2011). The BAC clone 100B10 was identified, integrated with the developed genetic map and partially sequenced.

Example 5

Isolation of the GmSHMT Genomic and cDNA Sequences

A 5.103 kb Forrest SHMT genomic DNA fragment (Genbank Accession No. JQ714083) spanning 2.339 kb of sequence 5' of the ATG start site, 2.189 kb of sequence from start to stop including 3 exon and 2 introns, and 0.675 kb of sequence 3' of the stop codon was cloned and sequenced. Because the 100B10 BAC clone contained only a partial SHMT gene sequence that included the 2.339 kb of sequence 5' of the ATG start site and 1.315 bp downstream of the ATG start site (see e.g., FIG. 1), an internal Sac I site at position 108 from the ATG start was used for a PCR-based cloning approach of the full length genomic sequence. First, a 2.447 kb fragment including the 2.339 kb of sequence 5' of the ATG start site and 108 bp of exon 1 was PCR amplified using a forward primer designed with an Asc I site and a reverse primer spanning the internal Sac I site. The fragment was digested and cloned into the CGT35S vector (Wang et al., 2010) using Asc I and Sac I. An Sbf I site was also introduced into the forward primer internal to Asc I for subsequent subcloning for complementation analysis (see e.g., TABLE 2). The remainder of the SHMT gDNA fragment, including the unique internal Sac I site, was amplified from Forrest genomic DNA by PCR with a forward primer spanning the internal Sac I site and a reverse primer designed with a Kpn I site. The fragment was digested and cloned into the Sac I and Kpn I sites downstream of the 5'fragment in the above CGT35S clone. The reverse primer was designed with a Sbf I site internal to Kpn I for the purpose of subsequent subcloning for complementation analysis (see e.g., TABLE 2). The fragments were ligated together utilizing the internal Sac I restriction site to generate the 5.103 kb SHMT genomic DNA fragment and sequenced. Primers designed to the Forrest genomic DNA sequence were used to clone the Essex SHMT genomic DNA sequence. PCR primers designed based on the Forrest and Essex genomic DNA sequences were used to amplify the corresponding cDNA sequences. Genomic DNA was isolated from young leaves using the DNeasy Plant Mini Kit (Qiagen Science, USA). Total RNA was isolated from roots using the RNeasy Plant Mini Kit (Qiagen) and cDNA was synthesized using a cDNA synthesis kit (Invitrogen).

Example 6

Mutation Screening of GmSHMT

Figure 2:
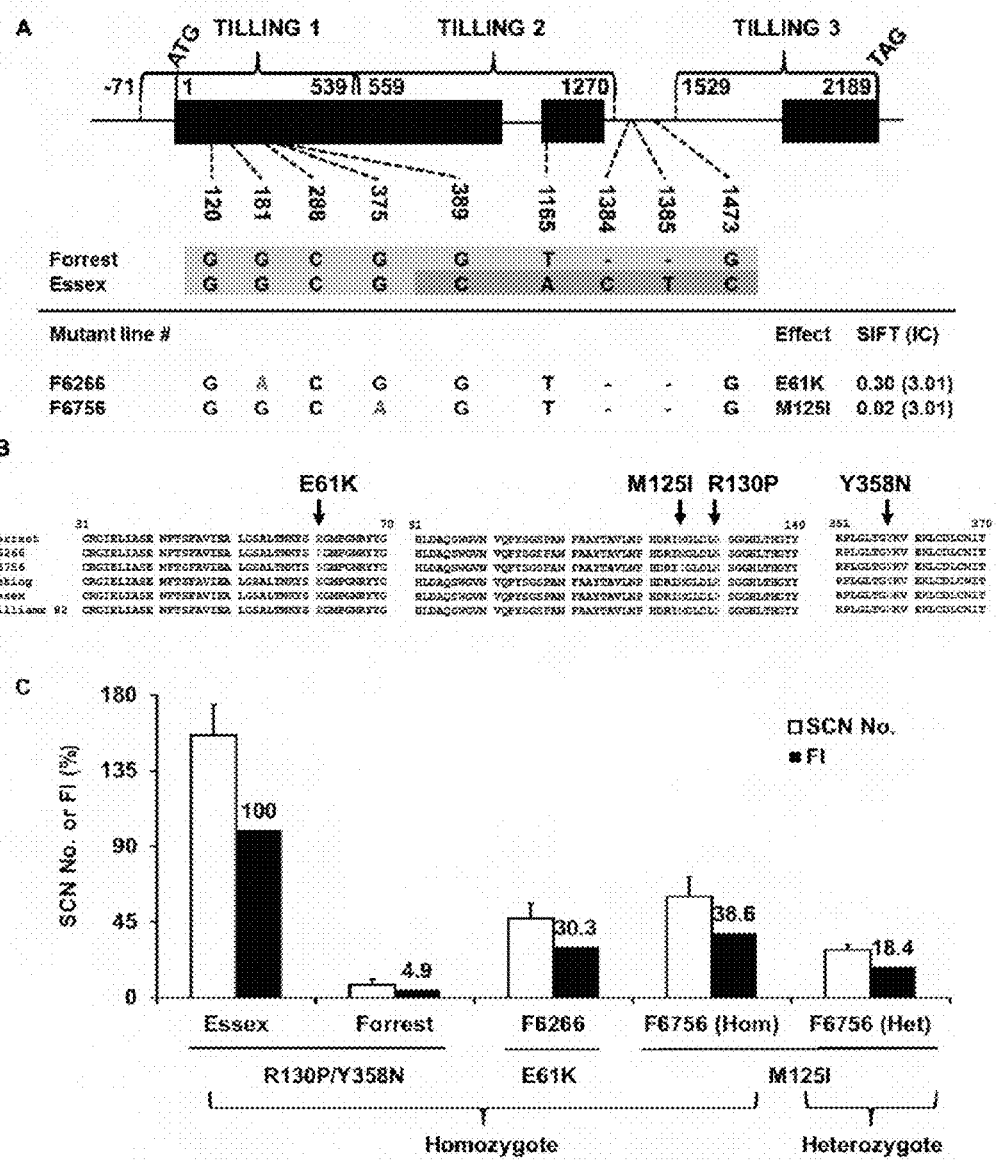
FIG. 2 is a drawing, sequence listing, and bar graph demonstrating the functional validation of GmSHMT by mutational analysis.

An EMS-mutagenized M2 population from SCN resistant cultivar Forrest containing 1,920 M2 families (Cooper et al., 2008, Meksem et al., 2008) was used to screen for mutations within the GmSHMT gene sequence. The gene was divided into 3 intervals (see e.g., FIG. 2) and TILLING was performed as previously described (Meksem et al., 2008). The GmSHMT gene of each mutant was sequenced to characterize the identified allele and its subsequent amino acid changes within the predicted protein sequences.

Example 7

Phenotype and Zygosity Analyses of GmSHMT TILLING Mutants

Mutants seeds were planted and scored for their SCN female index according to Brown et al. (2010). DNA from each plant was subjected to TILLING analysis without adding the reference wild type DNA of Forrest to the reaction tube before mismatch analyses to detect the zygosity level of the identified mutant.

Example 6

Haplotyping of Plant Introductions

A total of 81 soybean lines (plant introductions, landraces and elite cultivars) representing 90% of the genetic variability in soybean were scored for their SCN female index. Lines were classified resistant (R) to SCN if the FI was ≤10% and susceptible (S) if the FI was ≥10%. Soybean lines were genotyped at the Rhg4 locus using the DNA markers Sat_162, SHMT and SUB1 and at the rhg1 locus using the DNA markers 560, 570 and Satt309. The coding region of GmSHMT for 28 lines was sequenced. Common SNPs and Indels were identified and used to determine the different GmSHMT haplotypes.

Example 7

Virus-Induced Gene Silencing (VIGS)

Bean pod mottle virus (BPMV) VIGS vectors, pBPMV IA-R1M and pBPMV-IA-D35 were used in this example (Zhang et. al., 2010). pBPMV-IA-D35 is a derivative of pBPMV-IA-R2 containing Bam HI and Kpn I restriction sites between the cistrons encoding movement protein and the large coat protein subunit. Briefly, a 328 base pair (bp) fragment (spanning bps 210-537) of the GmSHMT cDNA sequence (Genbank Accession No. JQ714080) was amplified from soybean (cv. Forrest) root cDNA by RT-PCR. PCR products were digested with Bam HI and Kpn I and ligated into pBPMV-IA-D35 digested with the same enzymes to generate pBPMV-IA-SHMT. Gold particles coated with plasmid DNA corresponding to pBPMV-IA-R1M and pBPMV-IA-SHMT were co-bombarded into soybean leaf tissue as described in Zhang et al. (2010). At 3-4 weeks post-inoculation, BPMV-infected leaves were collected, lyophilized, and stored at −20° C. for future experiments. Infected soybean leaf tissues were ground in a mortar and pestle with 0.05 M potassium phosphate buffer (pH 7.0) and used as virus inoculum for VIGS assays.

The SCN-resistant RIL ExF67 was inoculated with pBPMV-IA-SHMT. Control plants were infected with BPMV only. Each treatment consisted of at least 12 plants. Unifoliate leaves of 9-dy-old plants were rub inoculated with virus using carborundum according to Zhang et al. (2010). Plants were grown in a growth chamber set to the following conditions: 20-21° C., 16 h light/8 h dark, and 100 mE $M^{-2}S^{-1}$ light intensity. Twenty-one days post virus inoculation, plants were inoculated with 1500 SCN eggs and maintained at 20° C. for 35 days. Cysts were isolated from the roots systems of individual plants by decanting and sieving and counted under a stereomicroscope. The results were plotted and analyzed for statistical significance by an unpaired t-test using GraphPad PRISM® software. To estimate GmSHMT gene silencing in roots, root tissues were harvested at 21-days post-virus inoculation (the time of nematode inoculation) from two representative plants inoculated with either pBPMV-IA-SHMT or BPMV only and frozen at −80° C. for RNA isolation and qPCR analysis.

Example 8

Hairy Root RNAi Experiments

A 338 bp fragment (spanning bps 205-542) of the GmSHMT cDNA sequence was amplified from soybean (cv. Forrest) root cDNA by RT-PCR, cloned into the pDONR-zeo gateway cloning vector (Invitrogen), and subsequently moved to a gateway RNAi binary vector under the control of the nematode-inducible Glyma15g04570.1 promoter (Kandoth et. al., 2011) (pZF-RNAi vector) to generate pZF-SHMTi. The pZF-RNAi vector was constructed by introducing gateway cloning sites flanking the FADR intron downstream of pZF promoter in the pAKK vector (Wang et al., 2010) which has a GFP selectable marker in planta. Transgenic ExF67 hairy roots transformed with pZF-SHMTi were produced from soybean cotyledons according to Kandoth et al. (2011). ExF63 and ExF67 hairy roots transformed with pZF-GUSi (the pZF-RNAi vector containing a portion of the GUS gene) were used as susceptible and resistant controls, respectively. GFP-positive hairy roots were root tip propagated three times on media containing antibiotic to clear Agrobacterium prior to nematode inoculation as described previously (Kandoth et al., 2011). Briefly, hairy roots (3-4 cm in length) were grown in square Petri plates and infected with approximately 400 sterile infective second-stage nematode juveniles one centimeter above the root tip. The plates were incubated in the dark at room temperature for 30 days. After 30 days, cysts were counted under a stereomicroscope. The experiment was conducted independently three times with a minimum of 12 independent hairy root lines per treatment. The results were plotted and analyzed for statistical significance by an unpaired t-test using GraphPad PRISM® software.

Example 9

Promoter-GUS Analysis

A 2.339 kb fragment corresponding to sequence 5' of the ATG start site of the Forrest SHMT gene (Genbank Accession No. JQ714083) and the same region from the Essex SHMT gene (Genbank Accession No. JQ714084) were amplified by PCR from the 100B10 BAC clone and Essex gDNA, respectively, and cloned into the pYXT1 vector (Xiao et al., 2005) to generate transcriptional fusions with the β-glucuronidase (GUS) gene. Soybean hairy roots transformed with these constructs were generated and infected with SCN. At two and four days post inoculation, root pieces excised from the infection zone were stained for GUS activity (Jefferson et al., 1987). Multiple roots from at least five independent lines were stained for each construct. Root pieces were fixed with 4% v/v paraformaldehyde in phosphate-buffered saline overnight at room temperature, embedded in paraffin, and sectioned longitudinally to a thickness of 10 μm. The sections were observed using differential interference contrast microscopy on a Vanox (Olympus) microscope and photographed with CMOS color digital camera.

Example 10

Genomic Complementation Experiments

The 5.103 kb Forrest SHMT genomic DNA fragment was subcloned into the Sbf 1 restriction site of the pAKK binary vector which has GFP selection for transgenic events. Transgenic hairy roots were produced and infected with SCN as described for RNAi experiments. The SCN-susceptible RIL ExF63 was used for the complementation experiment. Control hairy roots were produced by transforming ExF63 and ExF67 hairy roots with the pAKK binary vector carrying only the SHMT promoter sequence. The experiment was conducted independently five times with a minimum of 15 independent hairy root lines per treatment. The results were plotted and analyzed for statistical significance by an unpaired t-test using GraphPad PRISM® software.

Example 11

RNA Isolation and qPCR Analysis

Total RNA was isolated from root tissues using the RNeasy plant miniprep kit (Qiagen) according to the manufacturer's instructions. Real-time qRT-PCR was conducted as described in Kandoth et al. (2011).

Example 12

Computational Methods

A computational approach was performed to structurally and functionally annotate the identified GmSHMT protein and to estimate the effect of the mutations on GmSHMT function. Our approach consisted of two stages. First, a homology model of GmSHMT was obtained using Essex sequence as a target. Second, functional sites were mapped onto the surface of GmSHMT using the structural information of ligand binding by SHMT homologs. The homology analysis of GmSHMT has determined 43 structurally resolved SMHT homologs from a diverse set of bacterial and mammalian species; no structurally resolved plant SHMTs were found. Among the group of four homologs with the highest sequence similarities, the mouse SHMT (PDB ID 1EJI) with the largest coverage of the GmSHMT sequence (sequence identity 57%, template coverage 100%) was selected as a template for homology modeling of GmSHMT. Homology modeling was done using MODELLER-9 (Sali and Blundell, 1993) and the top-ranked model was selected from the set of candidate models using the building MODELLER scoring function. To determine the ligand binding sites for PLP-serine, PLP-glycine, and THF/MTHF)/FTHF, the obtained model of GmSHMT was structurally aligned with each of the orthologous SHMTs known to interact with the small ligands, and the ligand binding site from each homolog was mapped onto the surface of GmSHMT model through the structural alignment. The residues constituting the glycine binding sites, GBS1 and GBS2, in the SHMT homologs were identified in the literature and then mapped onto the structure of GmSHMT in a similar way, using the structural alignment of GmSHMT with its homolog.

Example 13

Positional Cloning of the Rhg4 Gene from SCN Resistant Soybean Cv. Forrest

Three genetic populations segregating for resistance to SCN were used for mapping. These included an F6 recombinant inbred line (RIL) population from a cross between Forrest and the SCN susceptible cv. Essex (98 individuals; Meksem et al., 2001), and two large F2 populations generated from crosses between Forrest and either Essex (1,755 lines) or the SCN susceptible cv. Williams 82 (2,060 lines), to enrich the chromosomal interval carrying the Rhg4 gene with recombinants.

Methods were according to Examples 1-12, unless described otherwise.

Because Forrest resistance to SCN requires both rhg1 and Rhg4 (Meksem et al., 2001), genotyping was conducted using DNA markers flanking both loci to detect informative recombinants at the Rhg4 locus (see e.g., TABLE 2). From a total of 355 recombinant lines identified with chromosomal breakpoints at the Rhg4 locus, two recombinants (ExF74 and FxW5093) were used to define the interval carrying the Rhg4 gene. Both lines carried the resistant allele at the rhg1 locus and were double recombinants for an 8 kb interval carrying the Rhg4 resistant allele (see e.g., FIG. 1). Two genes, one coding for a serine hydroxymethyltransferase (GmSHMT) and the other a subtilisin-like protease (GmSUB), were identified in the 8 kb interval. A comparison between the genomic DNA sequences of GmSHMT from Forrest and Essex showed 5 nucleotides differences (3 SNPs and 2 Ins/Dels) between the resistant and susceptible alleles; however, only two of the nucleotide differences found between the Forrest and Essex GmSHMT cDNAs resulted in an amino acid change in the predicted protein sequences (R130P and Y358N) (see e.g., FIG. 1D). The amino acid sequence at these two positions in Williams 82 was consistent with that of Essex (see e.g., FIG. 1D).

Example 14

GmSHMT Characterization

Figure 7B:
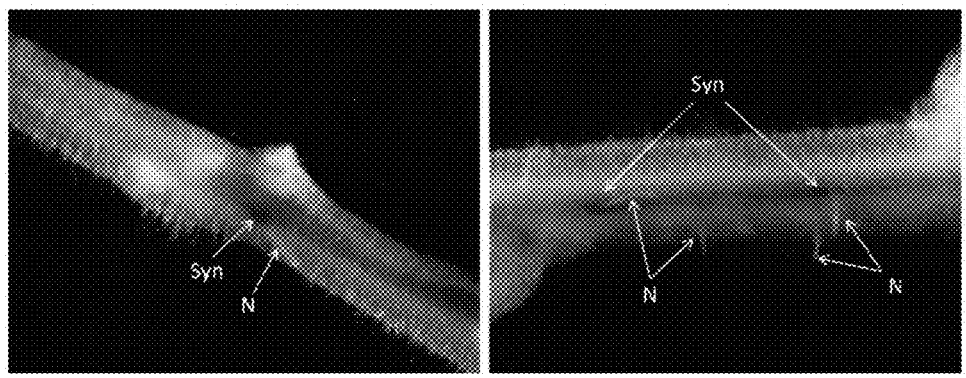
FIG. 7B is an image of Essex pSHMT-GUS.

Three nucleotide differences were identified in 2,339 bp of sequence 5' of the predicted start site for GmSHMT between Forrest and Essex (see e.g., FIG. 7). Based on these findings, GmSHMT was characterized further for a role in SCN resistance.

Methods were according to Examples 1-12, unless described otherwise.

Primers specific for GmSHMT (see e.g., TABLE 2) were used to screen a population of 1920 ethyl methane-sulfonate (EMS)-mutagenized M2 lines from the SCN resistant cultivar Forrest. Using a TILLING (Targeting Induced Local Lesions In Genomes) approach, two mutations in the GmSHMT gene were identified on chromosome 8 that led to missense mutations at E61K and M125I. SIFT predictions were performed on both mutations. SIFT predicts whether an amino acid substitution affects protein function based on sequence homology and the physical properties of amino acids (Kumar et al., 2009). SIFT predictions with IC<3.25 are considered confident. Changes with a SIFT score <0.05 are predicted to be damaging to the protein. Both missense mutations identified had IC values <3.25 (see e.g., FIG. 2), thus the SIFT predictions can be considered confident. Of the two TILLING mutants, the M125I mutation (SIFT score=0.02) was predicted to be deleterious to the protein. Both mutants were more susceptible to SCN in nematode infection assays (see e.g., FIG. 2). Additionally, in the segregating M3 mutant seed, the F6756 (M125I) mutation was correlated with the SCN resistance phenotype of individual plants.

These data indicated that GmSHMT at the Rhg4 locus plays a role in resistance to SCN.

Example 15

Identification of GmSHMT Haplotypes

A link was established between GmSHMT alleles and soybean resistance to SCN by scoring 81 soybean lines (including plant introductions, landraces and elite cultivars) representing 90% of the genetic variability in soybean for their SCN female index and determining their SNP-based GmSHMT haplotype.

Methods were according to Examples 1-12, unless described otherwise.

Figure 3:
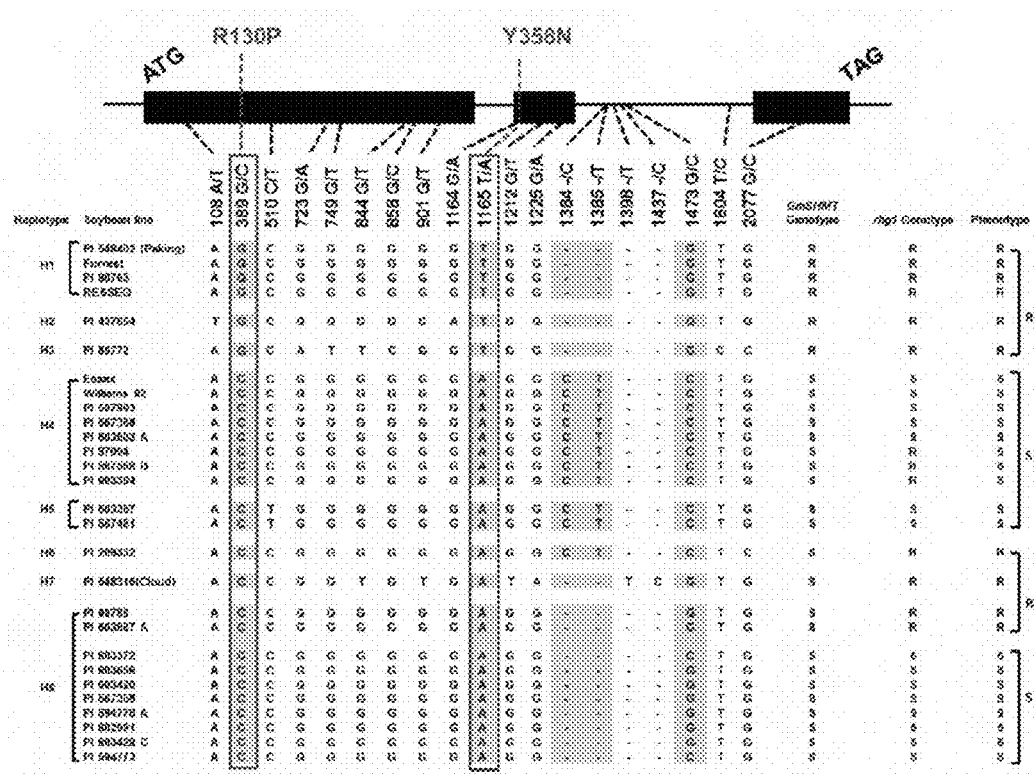
FIG. 3 is a table depicting haplotypes identified at GmSHMT in 28 plant introductions (PIs). A total of 81 soybean lines (plant introductions, landraces and elite cultivars) were scored for their SCN phenotype and SNP-genotyped at the rhg1 and Rhg4 loci (for a list see e.g., TABLE 1). The coding region of GmSHMT for 28 lines shown here was sequenced. Lines were classified resistant (R) to SCN if the FI≤10% and susceptible (S) if the FI≥10%. Polymorphic sites were positioned relative to the first nucleotide of the start codon in Forrest. Boxes indicate the G to C and T to A transitions resulting in the amino acid substitutions R130P and Y358N, respectively linked to SCN phenotype.

The GmSHMT gene was fully sequenced from 28 selected plant introductions including all known SCN reporter lines. 13 polymorphisms were identified in the coding regions and 6 in the non coding DNA sequences. Of the thirteen coding polymorphisms, two produced amino acid changes. The R130P and Y358N substitutions were responsible for the SCN phenotype except when SCN resistance is derived from plant introduction P188788. Eight different GmSHMT haplotypes were identified (see e.g., FIG. 3).

Soybean lines with haplotypes H1-H3 carried resistant alleles at GmSHMT and rhg1, and were resistant to SCN. These included soybean lines P1548402 (Peking), Forrest, P190763, P1437654, and P189772, all previously reported to exhibit what is known as "Peking type resistance" which requires both rhg1 and Rhg4 (Meksem et al., 2001). Soybean lines with haplotypes H4-H5 carried the susceptible allele at GmSHMT, but varied for either the resistant or susceptible allele at the rhg1 locus, those lines were susceptible to SCN regardless of the rhg1 allele, and included soybean cvs. Essex and Williams 82, both well known for their susceptibility to SCN. H6-H8 carried the susceptible allele at GmSHMT, but varied for either the resistant or susceptible allele at the rhg1 locus, those that carried the rhg1 susceptible allele were susceptible and those that carried the rhg1 resistant allele were resistant to SCN. These included P188788, P1209332, and P1548316 (cv. Cloud), all previously reported to exhibit what is known as "P188788 type resistance", which has been shown to require rhg1, but not Rhg4 for resistance to SCN (Concibidio et al., 2004).

In summary, the GmSHMT haplotyping analysis is in agreement with the previous SCN-resistant QTL reports (see e.g., review of Concibido et al., 2004) and confirms the requirement of Rhg4 for the Peking type of resistance to SCN.

Example 16

Validation of GmSHMT by VIGs, RNAi and Complementation

Knock down studies using VIGS (Virus Induced Gene Silencing) and targeted RNAi (RNA interference) provided further evidence that the GmSHMT gene confers resistance to *H. glycines*.

Methods were according to Examples 1-12, unless described otherwise.

It has been shown Bean pod mottle virus (BPMV, genus *Comovirus*) is an effective VIGS vector for soybean (Meyer et al., 2009; Pandey et al., 2011). Further, BPMV has a bipartite positive-strand RNA genome consisting of RNA-1 and RNA-2. A DNA-based system was used to place the cDNAs of BPMV genomic RNA1 and RNA2 under control of the *Cauliflower mosaic* Virus (CaMV 35S) promoter (Zhang et al., 2009) to clone 328-bp of GmSHMT into RNA2 and generate infectious tissue by biolistic delivery into soybean leaf tissues.

Nematode infection assays were conducted on soybean plants either inoculated with BPMV-SHMT or BPMV only. Two RIL lines were used which differed at the majority of markers assigned to the Rhg4 region and appeared to be nearly opposite recombination events. RIL lines, ExF67 (rhg1$_F$rhg1$_F$Rhg4$_F$Rhg4$_F$) and ExF63 (rhg1$_F$rhg1$_F$Rhg4$_E$Rhg4$_E$), are SCN-resistant and SCN-susceptible, respectively (Liu et al., 2011).

Results showed that silencing of the GmSHMT gene in the SCN-resistant RIL ExF67 resulted in a 29% increase in susceptibility to SCN compared to ExF67 inoculated with BPMV only (see e.g., FIG. 4A; P<0.0001). At the time of nematode inoculation of the plants, GmSHMT expression was determined by qRT-PCR to be reduced by an average of 74% in the roots of plants inoculated with BPMV-SHMT compared with those inoculated with BPMV only (see e.g., FIG. 4B).

Given the partial transcript reduction, transient nature, and inability to control spatial silencing of GmSHMT in roots with respect to the nematode using VIGS, a complementary targeted RNAi gene silencing approach was employed to test GmSHMT for a role in resistance to SCN. A 338-bp dsRNA corresponding to GmSHMT was expressed under control of a SCN-inducible zinc finger transcription factor promoter (Kandoth et al., 2011) in soybean hairy roots.

Results showed that nematode reproduction on hairy roots of the SCN resistant RIL ExF67 transformed with pZF-SHMTi was greater than on ExF67 hairy roots transformed with the pZF-GUSi control (see e.g., FIG. 4C; P<0.01). No statistically significant difference in nematode reproduction was observed between ExF67 hairy roots transformed with pZF-SHMTi and ExF63 hairy roots transformed with pZF-GUSi (see e.g., FIG. 4C).

These data further confirmed a role for GmSHMT in conferring SCN resistance.

2.3-kb of putative promoter sequence of GmSHMT from Forrest and Essex was fused with the β-glucuronidase (GUS) reporter gene to determine whether the GmSHMT gene is expressed in syncytial feeding cells induced by SCN and to determine whether the difference in resistance between the susceptible and resistant cultivars is related to the expression level of Rhg4, (Jefferson, 1987).

Results from nematode infection assays of soybean hairy roots transformed with the pSHMT-GUS constructs confirmed expression of GmSHMT within syncytia (see e.g., FIG. 4D-F). The same pattern of GUS expression was also observed in nematode-infected soybean hairy roots of ExF63 transformed with the Essex pSHMT-GUS construct (see e.g., FIG. 7B). No visible difference was detected between the resistant and susceptible line, which is in agreement with only three polymorphisms between Forrest and Essex in the putative 2.3-kb promoter region of GmSHMT (see e.g., FIG. 7A).

To confirm that GmSHMT was Rhg4, SCN susceptible RIL ExF63 was transformed with a 5.1-kb genomic fragment that included the Forrest SHMT gene with 2.3-kb of sequence upstream of the start and 0.57-kb downstream of the stop codon (gSHMT).

Results of nematode infection assays with *H. glycines* demonstrated restored resistance in the complemented transformed hairy roots (see e.g., FIG. 4G; P<0.0001), confirming that GmSHMT is the Rhg4 gene.

Example 16

Modeled Structure of GmSHMT

Using homology modeling, the structure of GmSHMT was predicted to examine how the variant genotypes (from the resistant and susceptible cultivars and TILLING mutants) may be affecting its structural and functional properties.

Methods were according to Examples 1-12, unless described otherwise.

The available structural information about small ligand binding by SHMT homologs was analyzed and mapped the ligand binding sites onto the surface of the GmSHMT model. As a result, five putative binding sites were determined, including two glycine ($GS_1$ and $GS_2$), one PLP-serine (PLS), one PLP-glycine (PLG), and one THF/MTHF/5-formylTHF (FTHF) binding site (see e.g., FIG. 5), with the latter three binding sites physically co-localized in the binding pocket formed by the SHMT dimer molecule. When mapping the Forrest and TILLING mutations onto the structural model of GmSHMT, both Forrest mutations and TILLING mutation F6266 E61K were found to be in close proximity to the tentative ligand binding sites. Specifically, it was found that the Forrest mutations P130R and N358Y were co-localized with the THF/MTHF/FTHF binding site and in close proximity to PLS, PLG and one of the two glycine binding sites. The position of the F6266 E61K mutation overlapped with the PLS and THF/MTHF/FTHF binding sites. These findings suggest that the three mutations may directly affect the reversible interconversion of L-serine and THF to glycine and MTHF. On the other hand, TILLING mutation F6756 M125I was found in an interior beta sheet (see e.g., FIG. 5), suggesting that there may be a different mechanism altering the function of GmSHMT in this mutant, perhaps through the structural instability of the region affected by the TILLING mutation. This hypothesis is in agreement with the previous functional genomics analysis using SIFT software (Kumar et al., 2009), which suggested that F6756 M125I is likely to be a deleterious mutation.

Genbank Accession Numbers

Forrest full-length genomic DNA, JQ714083; Essex full-length genomic DNA, JQ714084; Forrest cDNA sequence, JQ714080; Essex cDNA sequence, JQ714079; Forrest TILLING mutant F6266 sequence, JQ714081; Forrest TILLING mutant F6756 sequence, JQ714082.

Sequences

```
Essex Gm08-A2 SHMTcDNA sequence (1416 bases)
                                                        SEQ ID NO: 1
   1  ATGGATCCAG TAAGCGTGTG GGGTAACACG CCCTTGGCGA CGGTGGATCC CGAGATCCAT
      GACCTCATCG AGAAGGAGAA 81  GCGCCGTCAA TGCCGCGGAA TCGAGCTCAT CGCCTCCGAG AACTTCACCT CCTTCGCCGT
      CATCGAGGCC CTCGGCAGCG 161  CTCTCACGAA CAAATACTCC GAGGGCATGC CGGGCAACCG CTACTACGGC GGCAATGAAT
      ACATCGACCA GATCGAAAAC 241  CTCTGCCGCT CACGCGCCCT CCAAGCCTTC CACCTCGACG CCCAATCCTG GGGCGTCAAC
      GTCCAGCCCT ACTCCGGCTC 321  CCCGGCCAAC TTCGCCGCCT ACACCGCCGT CCTCAACCCC CACGACCGCA TCATGGGGCT
      AGATCTCCCC TCCGGCGGCC 401  ACCTCACCCA CGGCTACTAC ACCTCCGGCG AAAGAAGAT CTCCGCCACC TCCATTTACT
      TCGAGAGTCT CCCTTACAAG 481  GTAAACTCCA CCACCGGCTA CATCGACTAC GACCGCTTGG AAGAAAAAGC CCTAGACTTC
      AGGCCAAAAC TCATAATCTG 561  CGGTGGCAGC GCGTACCCTC GCGATTGGGA CTACAAACGT TCAGGGAAG TCGCTGATAA
      GTGCGGAGCA TTGCTTCTCT 641  GCGACATGGC GCACACTAGC GGCCTTGTGG CCGCGCAGGA AGTGAACAGC CCCTTCGAGT
      ATTGCGACAT TGTGACCACC 721  ACGACTCACA AGAGCTTGCG GGGCCCACGT GCGGGGATGA TCTTTTACCG GAAGGGCCCC
      AAGCCGCCGA AGAAGGGGCA 801  GCCGGAGAAC GCGGTTTATG ATTTCGAGGA CAAGATTAAC TTCGCGGTGT TCCCTTCGCT
      GCAGGGTGGG CCCCACAACC 881  ACCAGATCGG TGCTCTCGCC GTGGCGCTGA AGCAGGCCGC GTCGCCCGGG TTTAAGGCCT
      ACGCGAAGCA GGTTAAGGCG 961  AACGCCGTTG CGCTTGGAAA ATACTTGATG GGGAAAGGGT ACAGCCTTGT CACTGGCGGA
      ACGGAGAACC ATCTTGTTTT 1041  GTGGGATCTG AGACCTCTTG GATTGACTGG GAATAAGGTG GAGAAACTCT GTGATCTCTG
      TAACATTACT GTTAACAAGA 1121  ACGCTGTTTT TGGTGATAGC AGTGCCTTGG CCCCTGGTGG AGTGCGAATT GGTGCCCCTG
      CCATGACTTC TAGGGGTTTG 1201  GTTGAAAAAG ACTTTGAGCA GATTGGTGAG TTCCTTCACC GTGCTGTGAC TCTCACACTG
      GAGATCCAGA AGGAGCATGG 1281  CAAACTTCTC AAGGATTTCA ACAAGGGTCT CGTCAACAAC AAGGCTATTG AAGATCTCAA
      AGCTGATGTT GAGAAGTTCT

1361  CTGCCTTGTT TGACATGCCT GGCTTCCTGG TATCTGAAAT GAAGTACAAG GATTAG

Essex Gm08-A2 SHMT protein sequence (471 aa)
                                                        SEQ ID NO: 2
   1  MDPVSVWGNT PLATVDPEIH DLIEKEKRRQ CRGIELIASE NFTSFAVIEA LGSALTNKYS
      EGMPGNRYYG GNEYIDQIEN 81  LCRSRALQAF HLDAQSWGVN VQPYSGSPAN FAAYTAVLNP HDRIMGLDLP SGGHLTHGYY
      TSGGKKISAT SIYFESLPYK 161  VNSTTGYIDY DRLEEKALDF RPKLIICGGS AYPRDWDYKR FREVADKCGA LLLCDMAHTS
      GLVAAQEVNS PFEYCDIVTT 241  TTHKSLRGPR AGMIFYRKGP KPPKKGQPEN AVYDFEDKIN FAVFPSLQGG PHNHQIGALA
      VALKQAASPG FKAYAKQVKA 321  NAVALGKYLM GKGYSLVTGG TENHLVLWDL RPLGLTGNKV EKLCDLCNIT VNKNAVFGDS
      SALAPGGVRI GAPAMTSRGL
```

401 VEKDFEQIGE FLHRAVTLTL EIQKEHGKLL KDFNKGLVNN KAIEDLKADV EKFSALFDMP
    GFLVSEMKYK D

Essex GM08-A2-SHMTgDNA (5105 bases)

SEQ ID NO: 3

```
   1 CAATGGCACC AATGCCCAAT GGGAGATTTA AGTCAAGCCC AACATCAACC TCTGAAATTA
     TGAATTATGA AATTAAAATG

81 CTTCCTAGTA AGTGAACTAG TTGCATCTCA TTTATATCAT AAATTTCGAA CTACGACTTT
     CTTGGCCATG TTAGTAAAGT

161 TTGGGGGATT GTTCAAAATT GGTGGAGTGG TTCAGCTTAA TCTCCAAATT ATTTGTTCTA
     AGTTGTTTTG GTAGGCAGGT

241 TTAATTTTTT CCTGATCCTG GGAAAAAAAT TATTGATACC ATATTAACAT CTCTTGACGA
     TGCTACGAGA TTTCTCATGA

321 TTATAGAACT GAGTAGGGTG GCTTAAAAGG TTTTATTTTA AATATAATTT CACCACATTG
     AATTGGGTAT TAGTAAACTG

401 GTTACTGGTA TGCCTGTAAA GTGGACAATG ATAAATGTTT TTATAGAAGT TGGTATGGAT
     TTTAAAATAG CTCATGTATA

481 AAATGTGAAA AAGGAAACGT GAACTAAAAT GCTAATAATA AAGATAAAG ACTAAATTAA
     TTAAAGTTAA AGGATAAAAT

561 GCTTGTTACA TCAAGTCATT TTAAAGGTGC ACTATTAGAG CTGCACAGT AAAAGTTAAC
     ACTGATATAT TTTTAAAGAT

641 GTTCTTAGTT AAATAGCTTT TGACTTGATG GGGTGAAGAC ACAAGAGGTT GTTGTTGCGA
     TGTGATTTTG GCTGAATATG

721 CATGCCTGCT GAACATTGAC TTCATTGTTA AATCAAAATT AATCCCATAG ACCTATTGTA
     TTATTTAAGG GGATCAATTT

801 CATAAATCAA AATTTATTGG TTGGGGAAAA AAACAATGTT TAGTAGTTCC CAGTCATATT
     CAGAAACCTA CAAATTAACT

881 ATCCCCCATG TTAATGAAGC AAGGTGTGGG GGAAGGAAAG AGTCAGCATC AGTGAAGTAG
     AGAGGGGGGT TGGTGATTTT

961 GGTGGGAATA AATTGGCTAT ATTGCCCCCA CCAACCTCGT TGCTACCAAA TACCAACAAC
     ACTGACTCAC TGAGAATTGG

1041 GAAAGAAACT TAAAACCAAG TCTTGCAGTG ACGTACATGC AGTGTGTGCA TCACACATTC
     AGGTTTCCAG TCAAATTGTA

1121 GAACAAATGA ATTTCTTGCT TTAACTTAAG TTGAAGTTTA AGAAGTGAAG CTGATGCTTG
     TTTTTGAATG AAAAGCCTTT

1201 GATAGTTTGA TGTAAGCATT TTCCAAATTT AACTCTTCCC ATGCTTGACA GAGCCAATTA
     AGCTAACTGG TTTGATAACA

1281 AGTAAACTTC TAAATCTATG AGTATGAGTG CATGCAGCAC ACCTTTTAAA CACAAGCCAC
     TGTTTTGTCT TTTTTATCAA

1361 CAGAAAGAGA ATCCTACTAA TAACACTAAT CAAGATCGCT GCTCTTTTCT GTTTATTTTT
     CTTAATAAAT TAACTTTTGT

1441 TTTGTACTCC TGTTAAACAA CTGCTCTATT TGTTTCATGT GTTGCATTAA ATAACATGGT
     TTTATTCACA TCTACAAGCA

1521 AAATTTCCTA AAAACTGTGA ATGATGTAGA AGCAAGTCAT TTATGTTTTG AAATTCACGC
     ATTGGAGTTT CTAACGCCCA

1601 ACCAACCAAA CGGTAATATG AATATCGTGT TTGGAACAAA TTAGAATTTA GGACATAATT
     TTTCACATCA GAATAAATGT

1681 TAGGAATTTT TGCTTTTACG TTTTTCGCAT TAAAATAATG TGATTTATCG GTTGTTCCTG
     AACAATAACC ATCGATGTAA

1761 TTATAAAATT CTAATTTGTC CTATCCTGGG GCGTCAACGT CCAGCCAAAT GCGTAACATT
     TATTCTGATG TAAAAAATTA

1841 TTATTATTAT TATAGATAAT AAAATCTTGT TCCTGAACAA TAACCATCAA TGTAATTATA
     AAATTGAATC TTAGACTCAA

1921 AACTAGTTAT TAATCTGGAA CAATGTTTAC TCAAAACTAG TTATTAATAG TATTTTTAAG
     TTAATTTGAA ATTTTTTTTT
```

```
                                  -continued
2001  CGGCGTTAAA CAAATACTAG ATGTTTATAC TACAAATATT GATTATTGAT TATAAATTTA
      TAAATGTTAA AAAAAAAAA 2081  AAGAGAAAAC AAAGAATTGA AGTTGTGGTT GGTAGTAAAC CAGCACCAGG CGAACAAGTG
      GACACAATTT ACCTACAAGT 2161  AACTAACCAA CCGGAAGCAC AGGCTACAAC GGTCCTTTCA CACCCGGTCT CAAAGCTTTT
      AAAAACGAAC ACATACGCAC 2241  TCACATTTCC ATTCCACCTC AACAAACACA ACAACACTCT CTCTTCTCGC TCTTGGCTTT
      TCGCTCTTCA CTCACTCTCA 2321  TTCATTCATT TCCACCGTTC ATGGATCCAG TAAGCGTGTG GGGTAACACG CCCTTGGCGA
      CGGTGGATCC CGAGATCCAT 2401  GACCTCATCG AGAAGGAGAA GCGCCGTCAA TGCCGCGGAA TCGAGCTCAT CGCCTCCGAG
      AACTTCACCT CCTTCGCCGT 2481  CATCGAGGCC CTCGGCAGCG CTCTCACGAA CAAATACTCC GAGGGCATGC CGGGCAACCG
      CTACTACGGC GGCAATGAAT 2561  ACATCGACCA GATCGAAAAC CTCTGCCGCT CACGCGCCCT CCAAGCCTTC CACCTCGACG
      CCCAATCCTG GGGCGTCAAC 2641  GTCCAGCCCT ACTCCGGCTC CCCGGCCAAC TTCGCCGCCT ACACCGCCGT CCTCAACCCC
      CACGACCGCA TCATGGGGCT 2721  AGATCTCCCC TCCGGCGGCC ACCTCACCCA CGGCTACTAC ACCTCCGGCG GAAAGAAGAT
      CTCCGCCACC TCCATTTACT 2801  TCGAGAGTCT CCCTTACAAG GTAAACTCCA CCACCGGCTA CATCGACTAC GACCGCTTGG
      AAGAAAAAGC CCTAGACTTC 2881  AGGCCAAAAC TCATAATCTG CGGTGGCAGC GCGTACCCTC GCGATTGGGA CTACAAACGT
      TTCAGGGAAG TCGCTGATAA 2961  GTGCGGAGCA TTGCTTCTCT GCGACATGGC GCACACTAGC GGCCTTGTGG CCGCGCAGGA
      AGTGAACAGC CCCTTCGAGT 3041  ATTGCGACAT TGTGACCACC ACGACTCACA AGAGCTTGCG GGGCCCACGT GCGGGGATGA
      TCTTTTACCG GAAGGGCCCC 3121  AAGCCGCCGA AGAAGGGGCA GCCGGAGAAC GCGGTTTATG ATTTCGAGGA CAAGATTAAC
      TTCGCGGTGT TCCCTTCGCT 3201  GCAGGGTGGG CCCCACAACC ACCAGATCGG TGCTCTCGCC GTGGCGCTGA AGCAGGCCGC
      GTCGCCCGGG TTTAAGGCCT 3281  ACGCGAAGCA GGTTAAGGCG AACGCCGTTG CGCTTGGAAA ATACTTGATG GGGAAAGGGT
      ACAGCCTTGT CACTGGCGGA 3361  ACGGAGAACC ATCTTGTTTT GTGGGATCTG AGACCTCTTG GATTGACTGG TAATATATAT
      AGGATTGGAT CTCTACCTTC 3441  TGGTTTTGAT TTGTTACAAA TGTCTATAAA TCTGACTTGT TCGTTGTGTG ATTGTTTTGC
      AGGGAATAAG GTGGAGAAAC 3521  TCTGTGATCT CTGTAACATT ACTGTTAACA AGAACGCTGT TTTTGGTGAT AGCAGTGCCT
      TGGCCCCTGG TGGAGTGCGA 3601  ATTGGTAACG ATCTTACTTC TCTTTTATAT GCTACAATAC AAATCTTGCT TTACTAACTC
      AATTGGAAAC AAGATCTCAT 3681  TTATAAGATT ATAAAAATGA TTTCCTTAGG CTAGGACTAT ATCCTCTCTC TCTCTCTCTC
      TTTTTCTTTT TTATCATCGC 3761  AGAACTTAGA TGAATTTTCT TACGTAATTT TAGTACTGTT CTCTTATCAG AGTTCGAAAG
      TAAGTTATAA AATTTCTATT 3841  GAAGGCTTGC ATATTTATAT AAGTGAAATT TTAATTTTGG TTGGAGAACA ATGTCCAAAA
      CACCAAAGTG ATTGCATCTA 3921  AGTTTTTTGG ATTTTTTAAT GTATTTGTAT TTTGTACAAG GTATCTTAGT AAGTTGTTGT
      AGATTAGTAT TGAAAGAGAT 4001  TTCATTGAGG ATGTGTTTTT TAGTGCTTTA ACAAAGGAGG TATGTTAGTT CGGGCTAAAG
      CTTGCAGACT GCCTTTGTTA 4081  AAGAATTTCG AGTTGTTGTC GTGCAATATG ATTGGCAAAT CAATTATAAA CTAATCTGTT
      ATTTTGTTTT TCTGATACTT
```

-continued

```
4161  TTCCCTAGAA ATGAATTATT TTGATGTATC AATTACCAAA ATGGTTTTTT TGTGCCCCCG
      TTTCTGTATT TTTCTCTGAT

4241  GTGTTAGATA AATGTGAGTG CCCCTGACTG GAGTTTCTGT GAACAGGTGC CCCTGCCATG
      ACTTCTAGGG GTTTGGTTGA

4321  AAAAGACTTT GAGCAGATTG GTGAGTTCCT TCACCGTGCT GTGACTCTCA CACTGGAGAT
      CCAGAAGGAG CATGGCAAAC

4401  TTCTCAAGGA TTTCAACAAG GGTCTCGTCA ACAACAAGGC TATTGAAGAT CTCAAAGCTG
      ATGTTGAGAA GTTCTCTGCC

4481  TTGTTTGACA TGCCTGGCTT CCTGGTATCT GAAATGAAGT ACAAGGATTA GGTTCAACCA
      TACCACTTTC TACTAAATTG

4561  TGTCACTCAA GTTCGACACA AAGTGCAGAA ATGGAGAAAA AGGAAATATG TGTCTTCCTT
      TCCTGGGAGT GATAGGGTTT

4641  ATCGCCATGG TGTTTCAATT CAAAAGTTTG AAGTTTCTTT GTCTTTGATT TCATGTTTAA
      TTTTGTTAGC CTGATTGATA

4721  TCATATTTTT TTTCTTATTT AACAATTGAA ATAATACGTG CTGCCTTTCT TTCTTTTTTT
      TTCCTCGCTA GCTAGTAGTA

4801  TGTTTCATGA TTTCATCTTC TAATATTGCT CAACAGAACA TCTTAATTCT TAACAACCAT
      GAGTTTTAGT GGAGTTAAGC

4881  AAAAGAAAAA GTTATTCTAA TAAATCTATC GTCTTTCTTA TGCCTCAATG TCCTATGCCT
      CTCCCCCCTA TTTGAAAACC

4961  AAAATGCTCC ATGTCTAATT GTGATAAGCT GACAATACCC GTCTGGCAAA TTATGAAGTC
      AACATTTTTT TTTAGCTCAG

5041  CAATAACAAA TAATATTAAT TGCACAAGTG CTAAATAAC AATTGTTGGG CACCATAAAA
      TCTGG

Essex Gm08-A2 SHMT promoter
                                                               SEQ ID NO: 4
   1  CAATGGCACC AATGCCCAAT GGGAGATTTA AGTCAAGCCC AACATCAACC TCTGAAATTA
      TGAATTATGA AATTAAAATG 81  CTTCCTAGTA AGTGAACTAG TTGCATCTCA TTTATATCAT AAATTTCGAA CTACGACTTT
      CTTGGCCATG TTAGTAAAGT 161  TGGGGGATT GTTCAAAATT GGTGGAGTGG TTCAGCTTAA TCTCCAAATT ATTGTTCTA
      AGTTGTTTTG GTAGGCAGGT 241  TTAATTTTTT CCTGATCCTG GGAAAAAAAT TATTGATACC ATATTAACAT CTCTTGACGA
      TGCTACGAGA TTTCTCATGA 321  TTATAGAACT GAGTAGGGTG GCTTAAAAGG TTTTATTTTA AATATAATTT CACCACATTG
      AATTGGGTAT TAGTAAACTG 401  GTTACTGGTA TGCCTGTAAA GTGGACAATG ATAAATGTTT TTATAGAAGT TGGTATGGAT
      TTTAAAATAG CTCATGTATA 481  AAATGTGAAA AAGGAAACGT GAACTAAAAT GCTAATAATA AAAGATAAAG ACTAAATTAA
      TTAAAGTTAA AGGATAAAAT 561  GCTTGTTACA TCAAGTCATT TTAAAGGTGC ACTATTAGAG GCTGCACAGT AAAAGTTAAC
      ACTGATATAT TTTTAAAGAT 641  GTTCTTAGTT AAATAGCTTT TGACTTGATG GGGTGAAGAC ACAAGAGGTT GTTGTTGCGA
      TGTGATTTTG GCTGAATATG 721  CATGCCTGCT GAACATTGAC TTCATTGTTA AATCAAAATT AATCCCATAG ACCTATTGTA
      TTATTTAAGG GGATCAATTT 801  CATAAATCAA AATTTATTGG TTGGGGAAAA AAACAATGTT TAGTAGTTCC CAGTCATATT
      CAGAAACCTA CAAATTAACT 881  ATCCCCCATG TTAATGAAGC AAGGTGTGGG GGAAGGAAAG AGTCAGCATC AGTGAAGTAG
      AGAGGGGGT TGGTGATTTT 961  GGTGGGAATA AATTGGCTAT ATTGCCCCCA CCAACCTCGT TGCTACCAAA TACCAACAAC
      ACTGACTCAC TGAGAATTGG 1041  GAAAGAAACT TAAAACCAAG TCTTGCAGTG ACGTACATGC AGTGTGTGCA TCACACATTC
      AGGTTTCCAG TCAAATTGTA
```

-continued

```
1121  GAACAAATGA ATTTCTTGCT TTAACTTAAG TTGAAGTTTA AGAAGTGAAG CTGATGCTTG
      TTTTTGAATG AAAAGCCTTT

1201  GATAGTTTGA TGTAAGCATT TTCCAAATTT AACTCTTCCC ATGCTTGACA GAGCCAATTA
      AGCTAACTGG TTTGATAACA

1281  AGTAAACTTC TAAATCTATG AGTATGAGTG CATGCAGCAC ACCTTTTAAA CACAAGCCAC
      TGTTTTGTCT TTTTTATCAA

1361  CAGAAAGAGA ATCCTACTAA TAACACTAAT CAAGATCGCT GCTCTTTTCT GTTTATTTTT
      CTTAATAAAT TAACTTTTGT

1441  TTTGTACTCC TGTTAAACAA CTGCTCTATT TGTTTCATGT GTTGCATTAA ATAACATGGT
      TTTATTCACA TCTACAAGCA

1521  AAATTTCCTA AAAACTGTGA ATGATGTAGA AGCAAGTCAT TTATGTTTTG AAATTCACGC
      ATTGGAGTTT CTAACGCCCA

1601  ACCAACCAAA CGGTAATATG AATATCGTGT TTGGAACAAA TTAGAATTTA GGACATAATT
      TTTCACATCA GAATAAATGT

1681  TAGGAATTTT TGCTTTTACG TTTTTCGCAT TAAAATAATG TGATTTATCG GTTGTTCCTG
      AACAATAACC ATCGATGTAA

1761  TTATAAAATT CTAATTTGTC CTATCCTGGG GCGTCAACGT CCAGCCAAAT GCGTAACATT
      TATTCTGATG TAAAAAATTA

1841  TTATTATTAT TATAGATAAT AAAATCTTGT TCCTGAACAA TAACCATCAA TGTAATTATA
      AAATTGAATC TTAGACTCAA

1921  AACTAGTTAT TAATCTGGAA CAATGTTTAC TCAAAACTAG TTATTAATAG TATTTTTAAG
      TTAATTTGAA ATTTTTTTT

2001  CGGCGTTAAA CAAATACTAG ATGTTTATAC TACAAATATT GATTATTGAT TATAAATTTA
      TAAATGTTAA AAAAAAAAA

2081  AAGAGAAAAC AAAGAATTGA AGTTGTGGTT GGTAGTAAAC CAGCACCAGG CGAACAAGTG
      GACACAATTT ACCTACAAGT

2161  AACTAACCAA CCGGAAGCAC AGGCTACAAC GGTCCTTTCA CACCCGGTCT CAAAGCTTTT
      AAAACGAAC ACATACGCAC

2241  TCACATTTCC ATTCCACCTC AACAAACACA ACAACACTCT CTCTTCTCGC TCTTGGCTTT
      TCGCTCTTCA CTCACTCTCA

2321  TTCATTCATT TCCACCGTTC
```

REFERENCES

S. R. Koenning, J. A. Wrather, Suppression of soybean yield potential in the continental United States from plant diseases estimated from 2006 to 2009. Plant Health Prog. http://dx.doi.org/10.1094/PHP-2010-1122-01-RS (2010).

B. E. Caldwell, C. A. Brim, J. P. Ross, Inheritance of resistance of soybeans to the cyst nematode, *Heterodera glycines*. Agron J. 52,635-636 (1960).

A. L. Matson, L. F. Williams, Evidence of a fourth gene for resistance to the soybean cyst nematode. Crop Sci. 5, 477 (1965).

V. C. Concibido, B. W. Diers, P. R. Arelli, A decade of QTL mapping for cyst nematode resistance in soybean. Crop Sci. 44, 1121 (2004).

K. Meksem et al., Forrest' resistance to the soybean cyst nematode is bigenic: saturation mapping of the Rhg1 and Rhg4 loci. Theor. Appl. Genet. 103,710-717 (2001).

B. Y. Endo, Histological responses of resistant and susceptible soybean varieties, and backcross progeny to entry development of *Heterodera glycines*. Phytopathology 55, 375-381 (1965).

R. D. Riggs, K. S. Kim, I. Gipson, Ultrastructural changes in Peking soybeans infected with *Heterodera glycines*. Phytopathology 63, 76-84 (1973).

K. Dong, C. H. Opperman, Genetic analysis of parasitism in soybean cyst nematode *Heterodera glycines*. Genetics 146 (4), 1311-1318 (1997).

T. L. Niblack, A. L. Colgrove, K. Colgrove, J. P. Bond, Shift in virulence of soybean cyst nematode is associated with use of resistance from PI 88788. Online. Plant Health Progress doi:10.1094/PHP-2008-0118-01-RS. (2008).

S. Melito et al., A nematode demographics assay in transgenic roots reveals no significant impacts of the Rhg1 locus LRR-Kinase on soybean cyst nematode resistance. BMC Plant Biol. 10, 104 (2010).

X. Liu et al., Soybean cyst nematode resistance in soybean is independent of the Rhg4 locus LRR-RLK gene. Func. Integr. Gen. 11(4), 539-549 (2011).

J. D. F. Meyer et al., Identification and analyses of candidate genes for Rpp4-mediated resistance to Asian Soybean Rust in soybean. Plant Physiol. 150, 295-307 (2009).

A. K. Pandey et al., Functional analysis of the Asian Soybean Rust resistance pathway mediated by Rpp2, Mol. Plant-Microbe Interact. 24(2), 194-206 (2011).

P. K. Kandoth et al., The soybean Rhg1 locus for resistance to the soybean cyst nematode *Heterodera glycines* regulates expression of a large number of stress- and defense-related genes in degenerating feeding cells. Plant Physiol. 155:1960-1975 (2011).

R. A. Jefferson, Assaying chimeric genes in plants: the GUS gene fusion system. Plant Mol. Biol. Rep. 5, 387-405 (1987).

D. Cai et al., Positional cloning of a gene for nematode resistance in sugar beet. *Science* 275, 832-834 (1997).

S. B. Milligan et al., The root knot nematode resistance gene Mi from tomato is a member of the leucine zipper, nucleotide binding, leucine-rich repeat family of plant genes. *Plant Cell* 10, 1307-1319 (1998).

E. A. van der Vossen et al., Homologues of a single resistance gene cluster in potato confer resistance to distinct pathogens: a virus and a nematode. *Plant J.* 23, 567-576 (2000).

K. Ernst et al., The broad-spectrum potato cyst nematode resistance gene (Hero) from tomato is the only member of a large gene family of NBS-LRR genes with an unusual amino acid repeat in the LRR region. *Plant J.* 31, 127-136 (2002).

J. Paal et al., Molecular cloning of the potato Gro1-4 gene conferring resistance to pathotype Ro1 of the root nematode *Globodera rostochiensis*, based on a candidate gene approach. *Plant J.* 38, 285-297 (2004).

S. B. Renwick, K. Snell, U. Baumann, The crystal structure of human cytosolic serine hydroxymethyltransferase: a target for cancer therapy. *Structure* 6, 1105 (1998).

J. N. Scarsdale et al., Crystal structure at 2.4 A resolution of *E. coli* serine hydroxymethyltransferase in complex with glycine substrate and 5-formyl tetrahydrofolate. *J Mol. Biol.* 296, 155-168 (2000).

N. Sukanya et al., Serine hydroxymethyltransferase from mung bean (*Vigna radiata*) is not a pyridoxal-5'-phosphate-dependent enzyme. *Plant Physiol.* 95, 351-357 (1991).

P. Kumar, S. Henikoff, P. C. Ng, Predicting the effects of coding non-synonymous variants on protein function using the SIFT algorithm. *Nat Protoc.* 4, 1073-81 (2009).

Y. I. Kim, Role of folate in colon cancer development and progression. *J. Nutr.* 133, 3731S-3739S (2003).

E. F. Hartwig, J. M. Epps, Registration of 'Forrest' soybeans. *Crop Sci.* 13, 287 (1973).

T. J. Smith, H. M. Camper, Registration of Essex soybean. *Crop Sci.* 13, 495 (1973).

R. L. Bernard, C. R. Cremeens, Registration of 'Williams 82' soybean. *Crop Sci.* 28, 1072-1028 (1988).

J. L. Cooper et al., TILLING to detect induced mutations in soybean. *BMC Plant Biol.* 8, 123-132 (2008).

K. Meksem et al., TILLING: A reverse genetics and a functional genomics tool in soybean. In G. Kahl and K. Meksem, eds, The handbook of Plant Functional Genomics: Concepts and Protocols. Wiley-VCH Verlag GmbH & Co. KGaA, Weinheim, pp 251-265 (2008).

Sali, A., T. L. Blundell, Comparative protein modeling by satisfaction of spatial restraints. *J Mol Biol* 234(3), 779-815 (1993).

C. Q. Zhang, J. D. Bradshaw, S. A. Whitham, J. H. Hill, The development of an efficient multipurpose Bean pod mottle Virus viral vector set for foreign gene expression and RNA silencing. *Plant Physiol.* 153, 52-65 (2010).

S. Brown et al., A high-throughput automated technique for counting females of *Heterodera glycines* using a fluorescence-based imaging system. *J. Nematol.* 42(3), 201-201 (2010).

J. Wang et al., Dual roles for the variable domain in protein trafficking and host-specific recognition of *Heterodera glycines* CLE effector proteins. *New Phytol.* 187(4), 1003-1017 (2010).

K. Meksem et al., Two large-inset soybean genomic libraries constructed in a binary vector: Applications in chromosome walking and genome wide physical mapping. *Theor. Appl. Genet.* 101(5-6), 747-755 (2000).

K. E. Christensen, R. E. MacKenzie, Mitochondrial one-carbon metabolism is adapted to the specific needs of yeast, plants, and mammals. *BioEssays* 28(6), 595-605 (2006).

C. R. McClung et al., Integrated temporal regulation of the photorespiratory pathway. Circadian regulation of two *Arabidopsis* gene encoding serine hydroxymethyltransferase. *Plant Physiol.* 123(1), 381-391.

J. I. Moreno, R. Martin, C. Castresana, *Arabidopsis* SHMT1, a serine hydroxymethyltransferase that functions in the photorespiratory pathway influences resistance to biotic and abiotic. *Plant J.* 41(3), 451-463.

N. Ithal et al., Developmental transcript profiling of cyst nematode feeding cells in soybean roots. *Mol. Plant-Microbe Interact.* 20(5), 510-525.

J. Hofmann et al., Metabolic profiling reveal local and systemic responses of host plants to nematode parasitism. *Plant J.* 62(6), 1058-1071.

P. Novakovic, J. M. Stempak, K.-J. Sohn, Y.-I. Kim, Effects of folate deficiency on gene expression in the apoptosis and cancer in colon cancer cells. *Carcinogenesis* 27(5), 916-924.

S. G. Heil, et al., Is mutated serine hydroxymethyltransferase (SHMT) involved in the etiology of neural tube defects. *Mol. Genet. Metab.* 73(2), 164-172.

U. Lim, Polymorphisms in cytoplasmic serine hydroxymethyltransferase and methylenetetrahydrofolate reductase affect the risk of cardiovascular disease in men. *J. Nut.* 135 (8), 1989-1994.

C. F. Skibola et al., Polymorphisms in the thymidylate synthase and serine hydroxymethyltransferase genes and risk of adult acute lymphocytic leukemia. *Blood* 99(10), 3786-3791.

Y-L. Xiao, Analysis of the cDNAs of hypothetical genes on *Arabidopsis* chromosome 2 reveals numerous transcript variants. *Plant Physiol.* 139, 1323-1337.

J. R. Acedo, V. H. Dropkin, V. D. Luedders, Nematode population attrition and histopathology of *Heterodera glycines*-soybean associations. *J. Nematol.* 16, 48-56 (1984).

T. L. Niblack, R. D. Heinz, G. S. Smith, P. A. Donald. Distribution, density, and diversity of *Heterodera glycines* in Missouri. *J. Nematol.* 25, 880-886 (1993).

40

What is claimed is:

1. A plant of an agronomically elite soybean variety with soybean cyst nematode (SCN) resistance, comprising an GmSHMT allele containing mutations P130R and N358Y operably linked to a promoter, wherein the promoter comprises a sequence comprises the entire length of SEQ ID NO: 4 having the nucleic acid substitutions C1080T and C2244T and the nucleic acid deletion −2069A, or a functional fragment thereof, wherein the functional fragment comprises the nucleic acid substitutions C1080T and C2244T and the nucleic acid deletion −2069A.

2. A method of producing the plant of claim 1, the method comprising the steps of:
(a) crossing first and second soybean plants, wherein the first and second plants collectively comprise a GmSHMT allele containing mutations P130R and N358Y resulting in an SCN resistant phenotype, and wherein the first and second plants collectively comprise germplasm capable of conferring agronomically elite characteristics to a progeny plant of said plants;
(b) assaying progeny soybean plants resulting from the crossing for agronomically elite characteristics and for SCN resistance; and
(c) selecting at least a first progeny plant comprising said SCN resistant phenotype and agronomically elite characteristics.

3. A plant part of the plant of claim 1.

* * * * *

SEQUENCE LISTING

```
<160> NUMBER OF SEQ ID NOS: 123

<210> SEQ ID NO 1
<211> LENGTH: 1416
<212> TYPE: DNA
<213> ORGANISM: Glycine max

<400> SEQUENCE: 1
atggatccag taagcgtgtg gggtaacacg cccttggcga cggtggatcc cgagatccat      60
```

```
gacctcatcg agaaggagaa gcgccgtcaa tgccgcggaa tcgagctcat cgcctccgag    120
aacttcacct ccttcgccgt catcgaggcc ctcggcagcg ctctcacgaa caaatactcc    180
gagggcatgc cgggcaaccg ctactacggc ggcaatgaat acatcgacca gatcgaaaac    240
ctctgccgct cacgcgccct ccaagccttc cacctcgacg cccaatcctg ggcgtcaac     300 gtccagccct actccggctc cccggccaac ttcgccgcct acaccgccgt cctcaacccc    360
cacgaccgca tcatggggct agatctcccc tccggcggcc acctcaccca cggctactac    420
acctccggcg gaaagaagat ctccgccacc tccatttact tcgagagtct cccttacaag    480
gtaaactcca ccaccggcta catcgactac gaccgcttgg aagaaaaagc cctagacttc    540
aggccaaaac tcataatctg cggtggcagc gcgtaccctc gcgattggga ctacaaacgt    600
ttcagggaag tcgctgataa gtgcggagca ttgcttctct gcgacatggc gcacactagc    660
ggccttgtgg ccgcgcagga agtgaacagc cccttcgagt attgcgacat tgtgaccacc    720
acgactcaca agagcttgcg gggcccacgt gcggggatga tcttttaccg gaagggcccc    780
aagccgccga agaaggggca gccggagaac gcggtttatg atttcgagga caagattaac    840
ttcgcggtgt tcccttcgct gcagggtggg ccccacaacc accagatcgg tgctctcgcc    900
gtggcgctga agcaggccgc gtcgcccggg tttaaggcct acgcgaagca ggttaaggcg    960
aacgccgttg cgcttggaaa atacttgatg gggaaagggt acagccttgt cactggcgga    1020
acggagaacc atcttgtttt gtgggatctg agacctcttg gattgactgg gaataaggtg    1080
gagaaactct gtgatctctg taacattact gttaacaaga cgctgttttt tggtgatagc    1140
agtgccttgg ccctggtgg agtgcgaatt ggtgccctg ccatgacttc taggggtttg     1200
gttgaaaaag actttgagca gattggtgag ttccttcacc gtgctgtgac tctcacactg    1260
gagatccaga aggagcatgg caaacttctc aaggatttca acaagggtct cgtcaacaac    1320
aaggctattg aagatctcaa agctgatgtt gagaagttct ctgccttgtt tgacatgcct    1380
ggcttcctgg tatctgaaat gaagtacaag gattag                              1416
```

<210> SEQ ID NO 2
<211> LENGTH: 471
<212> TYPE: PRT
<213> ORGANISM: Glycine max

<400> SEQUENCE: 2

```
Met Asp Pro Val Ser Val Trp Gly Asn Thr Pro Leu Ala Thr Val Asp
1               5                   10                  15

Pro Glu Ile His Asp Leu Ile Glu Lys Glu Lys Arg Arg Gln Cys Arg
                20                  25                  30

Gly Ile Glu Leu Ile Ala Ser Glu Asn Phe Thr Ser Phe Ala Val Ile
            35                  40                  45

Glu Ala Leu Gly Ser Ala Leu Thr Asn Lys Tyr Ser Glu Gly Met Pro
        50                  55                  60

Gly Asn Arg Tyr Tyr Gly Gly Asn Glu Tyr Ile Asp Gln Ile Glu Asn
65                  70                  75                  80

Leu Cys Arg Ser Arg Ala Leu Gln Ala Phe His Leu Asp Ala Gln Ser
                85                  90                  95

Trp Gly Val Asn Val Gln Pro Tyr Ser Gly Ser Pro Ala Asn Phe Ala
                100                 105                 110

Ala Tyr Thr Ala Val Leu Asn Pro His Asp Arg Ile Met Gly Leu Asp
            115                 120                 125

Leu Pro Ser Gly Gly His Leu Thr His Gly Tyr Tyr Thr Ser Gly Gly
```

Lys Lys Ile Ser Ala Thr Ser Ile Tyr Phe Glu Ser Leu Pro Tyr Lys
145                 150                 155                 160

Val Asn Ser Thr Thr Gly Tyr Ile Asp Tyr Asp Arg Leu Glu Glu Lys
                165                 170                 175

Ala Leu Asp Phe Arg Pro Lys Leu Ile Ile Cys Gly Gly Ser Ala Tyr
            180                 185                 190

Pro Arg Asp Trp Asp Tyr Lys Arg Phe Arg Glu Val Ala Asp Lys Cys
        195                 200                 205

Gly Ala Leu Leu Leu Cys Asp Met Ala His Thr Ser Gly Leu Val Ala
        210                 215                 220

Ala Gln Glu Val Asn Ser Pro Phe Glu Tyr Cys Asp Ile Val Thr Thr
225                 230                 235                 240

Thr Thr His Lys Ser Leu Arg Gly Pro Arg Ala Gly Met Ile Phe Tyr
            245                 250                 255

Arg Lys Gly Pro Lys Pro Pro Lys Lys Gly Gln Pro Glu Asn Ala Val
            260                 265                 270

Tyr Asp Phe Glu Asp Lys Ile Asn Phe Ala Val Phe Pro Ser Leu Gln
        275                 280                 285

Gly Gly Pro His Asn His Gln Ile Gly Ala Leu Ala Val Ala Leu Lys
        290                 295                 300

Gln Ala Ala Ser Pro Gly Phe Lys Ala Tyr Ala Lys Gln Val Lys Ala
305                 310                 315                 320

Asn Ala Val Ala Leu Gly Lys Tyr Leu Met Gly Lys Gly Tyr Ser Leu
            325                 330                 335

Val Thr Gly Gly Thr Glu Asn His Leu Val Leu Trp Asp Leu Arg Pro
            340                 345                 350

Leu Gly Leu Thr Gly Asn Lys Val Glu Lys Leu Cys Asp Leu Cys Asn
        355                 360                 365

Ile Thr Val Asn Lys Asn Ala Val Phe Gly Asp Ser Ser Ala Leu Ala
        370                 375                 380

Pro Gly Gly Val Arg Ile Gly Ala Pro Ala Met Thr Ser Arg Gly Leu
385                 390                 395                 400

Val Glu Lys Asp Phe Glu Gln Ile Gly Glu Phe Leu His Arg Ala Val
            405                 410                 415

Thr Leu Thr Leu Glu Ile Gln Lys Glu His Gly Lys Leu Leu Lys Asp
            420                 425                 430

Phe Asn Lys Gly Leu Val Asn Asn Lys Ala Ile Glu Asp Leu Lys Ala
        435                 440                 445

Asp Val Glu Lys Phe Ser Ala Leu Phe Asp Met Pro Gly Phe Leu Val
        450                 455                 460

Ser Glu Met Lys Tyr Lys Asp
465                 470

<210> SEQ ID NO 3
<211> LENGTH: 5105
<212> TYPE: DNA
<213> ORGANISM: Glycine max

<400> SEQUENCE: 3
caatggcacc aatgcccaat gggagattta agtcaagccc acatcaacc tctgaaatta        60 tgaattatga aattaaaatg cttcctagta agtgaactag ttgcatctca tttatatcat      120
aaatttcgaa ctacgacttt cttggccatg ttagtaaagt ttgggggatt gttcaaaatt      180

```
ggtggagtgg ttcagcttaa tctccaaatt atttgttcta agttgttttg gtaggcaggt    240 ttaattttt  cctgatcctg ggaaaaaaat tattgatacc atattaacat ctcttgacga    300
tgctacgaga tttctcatga ttatagaact gagtagggtg gcttaaaagg tttttatttta   360 aatataattt caccacattg aattgggtat tagtaaactg gttactggta tgcctgtaaa    420
gtggacaatg ataaatgttt ttatagaagt tggtatggat tttaaaatag ctcatgtata    480
aaatgtgaaa aaggaaacgt gaactaaaat gctaataata aaagataaag actaaattaa    540
ttaaagttaa aggataaaat gcttgttaca tcaagtcatt ttaaaggtgc actattagag    600
gctgcacagt aaaagttaac actgatatat ttttaaagat gttcttagtt aaatagcttt    660
tgacttgatg gggtgaagac acaagaggtt gttgttgcga tgtgattttg gctgaatatg    720
catgcctgct gaacattgac ttcattgtta aatcaaaatt aatcccatag acctattgta    780
ttatttaagg ggatcaattt cataaatcaa aatttattgg ttggggaaaa aaacaatgtt    840
tagtagttcc cagtcatatt cagaaaccta caaattaact atcccccatg ttaatgaagc    900
aaggtgtggg ggaaggaaag agtcagcatc agtgaagtag agaggggggt tggtgattt    960 ggtgggaata aattggctat attgcccca ccaacctcgt tgctaccaaa taccaacaac    1020
actgactcac tgagaattgg gaaagaaact aaaaccaag tcttgcagtg acgtacatgc    1080
agtgtgtgca tcacacattc aggttttccag tcaaattgta gaacaaatga atttcttgct   1140
ttaacttaag ttgaagttta agaagtgaag ctgatgcttg tttttgaatg aaaagccttt    1200
gatagtttga tgtaagcatt ttccaaattt aactcttccc atgcttgaca gagccaatta   1260
agctaactgg tttgataaca agtaaacttc taaatctatg agtatgagtg catgcagcac    1320
acctttaaaa cacaagccac tgttttgtct tttttatcaa cagaaagaga atcctactaa   1380
taacactaat caagatcgct gctcttttct gtttattttt cttaataaat taactttgt    1440 tttgtactcc tgttaaacaa ctgctctatt tgtttcatgt gttgcattaa ataacatggt   1500
tttattcaca tctacaagca aaatttccta aaaactgtga atgatgtaga agcaagtcat    1560 ttatgtttg  aaattcacgc attggagttt ctaacgccca accaaccaaa cggtaatatg    1620
aatatcgtgt ttggaacaaa ttagaattta ggacataatt tttcacatca gaataaatgt    1680 taggaattt  tgcttttacg tttttcgcat taaaataatg tgatttatcg gttgttcctg    1740
aacaataacc atcgatgtaa ttataaaatt ctaatttgtc ctatcctggg gcgtcaacgt    1800
ccagccaaat gcgtaacatt tattctgatg taaaaaatta ttattattat tatagataat   1860
aaaatcttgt tcctgaacaa taaccatcaa tgtaattata aaattgaatc ttagactcaa    1920
aactagttat taatctggaa caatgtttac tcaaaactag ttattaatag tattttaag    1980 ttaatttgaa atttttttt  cggcgttaaa caaatactag atgtttatac tacaaatatt    2040
gattattgat tataaattta taaatgttaa aaaaaaaaaa aagagaaaac aaagaattga    2100
agttgtggtt ggtagtaaac cagcaccagg cgaacaagtg gacacaattt acctacaagt    2160
aactaaccaa ccggaagcac aggctacaac ggtcctttca cacccggtct caaagctttt    2220 aaaacgaac  acatacgcac tcacatttcc attccacctc aacaaacaca acaacactct    2280
ctcttctcgc tcttggcttt tcgctcttca ctcactctca ttcattcatt tccaccgttc    2340
atggatccag taagcgtgtg gggtaacacg cccttggcga cggtggatcc cgagatccat    2400
gacctcatcg agaaggagaa gcgccgtcaa tgccgcggaa tcgagctcat cgcctccgag    2460
aacttcacct ccttcgccgt catcgaggcc ctcggcagcg ctctcacgaa caaatactcc    2520
gagggcatgc cgggcaaccg ctactacggc ggcaatgaat acatcgacca gatcgaaaac    2580
```

```
ctctgccgct cacgcgccct ccaagccttc cacctcgacg cccaatcctg gggcgtcaac    2640
gtccagcccT actccggctc cccggccaac ttcgccgcct acaccgccgt cctcaacccc    2700
cacgaccgca tcatggggct agatctcccc tccggcggcc acctcaccca cggctactac    2760
acctccggcg aaagaagat  ctccgccacc tccatttact tcgagagtct cccttacaag    2820
gtaaactcca ccaccggcta catcgactac gaccgcttgg aagaaaaagc cctagacttc    2880
aggccaaaac tcataatctg cggtggcagc gcgtaccctc gcgattggga ctacaaacgt    2940 ttcaggaag  tcgctgataa gtgcggagca ttgcttctct gcgacatggc gcacactagc    3000
ggccttgtgg ccgcgcagga agtgaacagc cccttcgagt attgcgacat tgtgaccacc    3060
acgactcaca agagcttgcg gggcccacgt gcggggatga tcttttaccg aagggccccc   3120
aagccgccga agaaggggca gccggagaac gcggtttatg atttcgagga caagattaac    3180
ttcgcggtgt tcccttcgct gcagggtggg ccccacaacc accagatcgg tgctctcgcc    3240
gtggcgctga agcaggccgc gtcgcccggg tttaaggcct acgcgaagca ggttaaggcg    3300
aacgccgttg cgcttggaaa atacttgatg gggaagggt  acagccttgt cactggcgga    3360
acggagaacc atcttgtttt gtgggatctg agacctcttg gattgactgg taatatatat    3420
aggattggat ctctaccttc tggttttgat ttgttacaaa tgtctataaa tctgacttgt    3480
tcgttgtgtg attgttttgc agggaataag gtggagaaac tctgtgatct ctgtaacatt    3540
actgttaaca agaacgctgt ttttggtgat agcagtgcct tggcccctgg tggagtgcga    3600
attggtaacg atcttacttc tcttttatat gctacaatac aaatcttgct ttactaactc    3660
aattggaaac aagatctcat ttataagatt ataaaaatga tttccttagg ctaggactat    3720
atcctctctc tctctctctc ttttttcttt ttatcatcgc agaacttaga tgaattttct    3780
tacgtaattt tagtactgtt ctcttatcag agttcgaaag taagttataa aatttctatt    3840
gaaggcttgc atatttatat aagtgaaatt ttaattttgg ttggagaaca atgtccaaaa    3900
caccaaagtg attgcatcta agttttttgg atttttttaat gtatttgtat tttgtacaag    3960
gtatcttagt aagttgttgt agattagtat tgaaagagat ttcattgagg atgtgttttt    4020
tagtgcttta acaaaggagg tatgttagtt cgggctaaag cttgcagact gcctttgtta    4080
aagaatttcg agttgttgtc gtgcaatatg attggcaaat caattataaa ctaatctgtt    4140
attttgttTt tctgatactt ttccctagaa atgaattatt ttgatgtatc aattaccaaa    4200
atggtttttt tgtgcccccg tttctgtatt tttctctgat gtgttagata aatgtgagtg    4260
cccctgactg gagtttctgt gaacaggtgc ccctgccatg acttctaggg gtttggttga    4320 aaagacttt  gagcagattg gtgagttcct tcaccgtgct gtgactctca cactggagat    4380
ccagaaggag catggcaaac ttctcaagga tttcaacaag ggtctcgtca acaacaaggc    4440
tattgaagat ctcaaagctg atgttgagaa gttctctgcc ttgtttgaca tgcctggctt    4500
cctggtatct gaaatgaagt acaaggatta ggttcaacca taccactttc tactaaattg    4560
tgtcactcaa gttcgacaca aagtgcagaa atggagaaaa aggaaatatg tgtcttcctt    4620
tcctgggagt gatagggttt atcgccatgg tgtttcaatt caaagtttg  aagtttcttt    4680 gtctttgatt tcatgtttaa ttttgttagc ctgattgata tcatattttt ttcttattt    4740 aacaattgaa ataatacgtg ctgcctttct ttctttttttt ttcctcgcta gctagtagta    4800
tgtttcatga tttcatcttc taatattgct caacagaaca tcttaattct taacaaccat    4860
gagttttagt ggagttaagc aaaagaaaaa gttattctaa taaatctatc gtctttctta    4920
```

```
tgcctcaatg tcctatgcct ctccccccta tttgaaaacc aaaatgctcc atgtctaatt      4980
gtgataagct gacaataccc gtctggcaaa ttatgaagtc aacattttt tttagctcag       5040 caataacaaa taatattaat tgcacaagtg ctaaataac aattgttggg caccataaaa       5100
tctgg                                                                  5105
```

<210> SEQ ID NO 4
<211> LENGTH: 2340
<212> TYPE: DNA
<213> ORGANISM: Glycine max

<400> SEQUENCE: 4

```
caatggcacc aatgcccaat gggagattta agtcaagccc acatcaacc tctgaaatta        60 tgaattatga aattaaaatg cttcctagta agtgaactag ttgcatctca tttatatcat      120
aaatttcgaa ctacgacttt cttggccatg ttagtaaagt ttgggggatt gttcaaaatt      180
ggtggagtgg ttcagcttaa tctccaaatt atttgttcta agttgttttg gtaggcaggt      240
ttaatttttt cctgatcctg ggaaaaaaat tattgatacc atattaacat ctcttgacga      300
tgctacgaga tttctcatga ttatagaact gagtagggtg gcttaaaagg ttttatttta      360
aatataattt caccacattg aattgggtat tagtaaactg gttactggta tgcctgtaaa      420
gtggacaatg ataaatgttt ttatagaagt tggtatggat tttaaaatag ctcatgtata      480
aaatgtgaaa aaggaaacgt gaactaaaat gctaataata aaagataaag actaaattaa      540
ttaaagttaa aggataaaat gcttgttaca tcaagtcatt ttaaaggtgc actattagag      600
gctgcacagt aaaagttaac actgatatat ttttaaagat gttcttagtt aaatagcttt      660
tgacttgatg gggtgaagac acaagaggtt gttgttgcga tgtgattttg gctgaatatg      720
catgcctgct gaacattgac ttcattgtta aatcaaaatt aatcccatag acctattgta      780
ttatttaagg ggatcaattt cataaatcaa aatttattgg ttggggaaaa aaacaatgtt      840
tagtagttcc cagtcatatt cagaaaccta caaattaact atccccccatg ttaatgaagc      900 aaggtgtggg ggaaggaaag agtcagcatc agtgaagtag agagggggt tggtgatttt      960 ggtgggaata aattggctat attgcccccca ccaacctcgt tgctaccaaa taccaacaac     1020
actgactcac tgagaattgg gaaagaaact taaaaccaag tcttgcagtg acgtacatgc     1080
agtgtgtgca tcacacattc aggtttccag tcaaattgta gaacaaatga atttcttgct     1140
ttaacttaag ttgaagttta agaagtgaag ctgatgcttg ttttttgaatg aaaagccttt     1200 gatagtttga tgtaagcatt ttccaaattt aactcttccc atgcttgaca gagccaatta     1260
agctaactgg tttgataaca agtaaacttc taaatctatg agtatgagtg catgcagcac     1320
accttttaaa cacaagccac tgttttgtct ttttttatcaa cagaaagaga atcctactaa     1380
taacactaat caagatcgct gctcttttct gtttattttt cttaataaat taactttgt      1440 tttgtactcc tgttaaacaa ctgctctatt tgtttcatgt gttgcattaa ataacatggt     1500
tttattcaca tctacaagca aaatttccta aaaactgtga atgatgtaga agcaagtcat     1560
ttatgttttg aaattcacgc attggagttt ctaacgccca accaaccaaa cggtaatatg     1620
aatatcgtgt ttggaacaaa ttagaattta ggacataatt tttcacatca gaataaatgt     1680
taggaatttt tgcttttacg ttttttcgcat taaaataatg tgatttatcg gttgttcctg     1740
aacaataacc atcgatgtaa ttataaaatt ctatttgtc ctatcctggg gcgtcaacgt      1800
ccagccaaat gcgtaacatt tattctgatg taaaaaatta ttattattat tatagataat     1860
aaaatcttgt tcctgaacaa taaccatcaa tgtaattata aaattgaatc ttagactcaa     1920
```

```
aactagttat taatctggaa caatgtttac tcaaaactag ttattaatag tattttttaag    1980 ttaatttgaa atttttttt cggcgttaaa caaatactag atgtttatac tacaaatatt     2040
gattattgat tataaattta taatgttaa aaaaaaaaaa aagagaaaac aaagaattga     2100
agttgtggtt ggtagtaaac cagcaccagg cgaacaagtg gacacaattt acctacaagt    2160
aactaaccaa ccggaagcac aggctacaac ggtcctttca cacccggtct caaagctttt    2220
aaaaacgaac acatacgcac tcacatttcc attccacctc aacaaacaca acaacactct    2280
ctcttctcgc tcttggcttt tcgctcttca ctcactctca ttcattcatt tccaccgttc    2340
```

<210> SEQ ID NO 5
<211> LENGTH: 24
<212> TYPE: DNA
<213> ORGANISM: Artificial Sequence
<220> FEATURE:
<223> OTHER INFORMATION: DNA Primer

<400> SEQUENCE: 5
gggctatgaa gggaatggaa agga                                              24

<210> SEQ ID NO 6
<211> LENGTH: 24
<212> TYPE: DNA
<213> ORGANISM: Artificial Sequence
<220> FEATURE:
<223> OTHER INFORMATION: DNA Primer

<400> SEQUENCE: 6
cccatattga agatttgaag taat                                              24

<210> SEQ ID NO 7
<211> LENGTH: 22
<212> TYPE: DNA
<213> ORGANISM: Artificial Sequence
<220> FEATURE:
<223> OTHER INFORMATION: DNA Primer

<400> SEQUENCE: 7
gcgtggtttt tcgctggata ta                                                22

<210> SEQ ID NO 8
<211> LENGTH: 25
<212> TYPE: DNA
<213> ORGANISM: Artificial Sequence
<220> FEATURE:
<223> OTHER INFORMATION: DNA Primer

<400> SEQUENCE: 8
gcgcatttcg taacatattt ttcac                                             25

<210> SEQ ID NO 9
<211> LENGTH: 20
<212> TYPE: DNA
<213> ORGANISM: Artificial Sequence
<220> FEATURE:
<223> OTHER INFORMATION: DNA Primer

<400> SEQUENCE: 9
agcgggaatt gaaggttttt                                                   20

<210> SEQ ID NO 10
<211> LENGTH: 24
<212> TYPE: DNA

<213> ORGANISM: Artificial Sequence
<220> FEATURE:
<223> OTHER INFORMATION: DNA Primer

<400> SEQUENCE: 10
ggaatctcat ctgaaaataa tgga                                              24

<210> SEQ ID NO 11
<211> LENGTH: 26
<212> TYPE: DNA
<213> ORGANISM: Artificial Sequence
<220> FEATURE:
<223> OTHER INFORMATION: DNA Primer

<400> SEQUENCE: 11
gcgccagcaa caaagttcct gacaaa                                            26

<210> SEQ ID NO 12
<211> LENGTH: 22
<212> TYPE: DNA
<213> ORGANISM: Artificial Sequence
<220> FEATURE:
<223> OTHER INFORMATION: DNA Primer

<400> SEQUENCE: 12
gcgcatgcaa atgaaataat aa                                                22

<210> SEQ ID NO 13
<211> LENGTH: 21
<212> TYPE: DNA
<213> ORGANISM: Artificial Sequence
<220> FEATURE:
<223> OTHER INFORMATION: DNA Primer

<400> SEQUENCE: 13
gcgccttcaa attggcgtct t                                                 21

<210> SEQ ID NO 14
<211> LENGTH: 24
<212> TYPE: DNA
<213> ORGANISM: Artificial Sequence
<220> FEATURE:
<223> OTHER INFORMATION: DNA Primer

<400> SEQUENCE: 14
gcgccttaaa taaaacccga aact                                              24

<210> SEQ ID NO 15
<211> LENGTH: 21
<212> TYPE: DNA
<213> ORGANISM: Artificial Sequence
<220> FEATURE:
<223> OTHER INFORMATION: DNA Primer

<400> SEQUENCE: 15
tgttacttag taattatgaa g                                                 21

<210> SEQ ID NO 16
<211> LENGTH: 21
<212> TYPE: DNA
<213> ORGANISM: Artificial Sequence
<220> FEATURE:
<223> OTHER INFORMATION: DNA Primer

<400> SEQUENCE: 16
aataatgatt tgttgatcga t                                                 21

<210> SEQ ID NO 17
<211> LENGTH: 26
<212> TYPE: DNA
<213> ORGANISM: Artificial Sequence
<220> FEATURE:
<223> OTHER INFORMATION: DNA Primer

<400> SEQUENCE: 17
gcgaagccca tactccgaac ctgcca                                        26

<210> SEQ ID NO 18
<211> LENGTH: 25
<212> TYPE: DNA
<213> ORGANISM: Artificial Sequence
<220> FEATURE:
<223> OTHER INFORMATION: DNA Primer

<400> SEQUENCE: 18
gcctccaaaa actcaacccc atcaa                                         25

<210> SEQ ID NO 19
<211> LENGTH: 24
<212> TYPE: DNA
<213> ORGANISM: Artificial Sequence
<220> FEATURE:
<223> OTHER INFORMATION: DNA Primer

<400> SEQUENCE: 19
gggctatgaa gggaatggaa agga                                          24

<210> SEQ ID NO 20
<211> LENGTH: 24
<212> TYPE: DNA
<213> ORGANISM: Artificial Sequence
<220> FEATURE:
<223> OTHER INFORMATION: DNA Primer

<400> SEQUENCE: 20
cccatattga agatttgaag taat                                          24

<210> SEQ ID NO 21
<211> LENGTH: 23
<212> TYPE: DNA
<213> ORGANISM: Artificial Sequence
<220> FEATURE:
<223> OTHER INFORMATION: DNA Primer

<400> SEQUENCE: 21
gatgccttac gcctgtcact aac                                           23

<210> SEQ ID NO 22
<211> LENGTH: 24
<212> TYPE: DNA
<213> ORGANISM: Artificial Sequence
<220> FEATURE:
<223> OTHER INFORMATION: DNA Primer

<400> SEQUENCE: 22
gcagaacagt agaacaagtc cagt                                          24

<210> SEQ ID NO 23
<211> LENGTH: 23
<212> TYPE: DNA
<213> ORGANISM: Artificial Sequence
<220> FEATURE:

```
<223> OTHER INFORMATION: DNA Primer

<400> SEQUENCE: 23
gcccaccagt tgttgtgtaa gac                                           23

<210> SEQ ID NO 24
<211> LENGTH: 22
<212> TYPE: DNA
<213> ORGANISM: Artificial Sequence
<220> FEATURE:
<223> OTHER INFORMATION: DNA Primer

<400> SEQUENCE: 24
gcgtgcgatg agaaactcag ac                                            22

<210> SEQ ID NO 25
<211> LENGTH: 22
<212> TYPE: DNA
<213> ORGANISM: Artificial Sequence
<220> FEATURE:
<223> OTHER INFORMATION: DNA Primer

<400> SEQUENCE: 25
gcgtggtttt tcgctggata ta                                            22

<210> SEQ ID NO 26
<211> LENGTH: 25
<212> TYPE: DNA
<213> ORGANISM: Artificial Sequence
<220> FEATURE:
<223> OTHER INFORMATION: DNA Primer

<400> SEQUENCE: 26
gcgcatttcg taacatattt ttcac                                         25

<210> SEQ ID NO 27
<211> LENGTH: 24
<212> TYPE: DNA
<213> ORGANISM: Artificial Sequence
<220> FEATURE:
<223> OTHER INFORMATION: DNA Primer

<400> SEQUENCE: 27
gaagttggtg actgcgggaa atgc                                          24

<210> SEQ ID NO 28
<211> LENGTH: 24
<212> TYPE: DNA
<213> ORGANISM: Artificial Sequence
<220> FEATURE:
<223> OTHER INFORMATION: DNA Primer

<400> SEQUENCE: 28
ttcaatgcac cgatccaaca agga                                          24

<210> SEQ ID NO 29
<211> LENGTH: 21
<212> TYPE: DNA
<213> ORGANISM: Artificial Sequence
<220> FEATURE:
<223> OTHER INFORMATION: DNA Primer

<400> SEQUENCE: 29
tacaagtcag taatataacc t                                             21
```

```
<210> SEQ ID NO 30
<211> LENGTH: 21
<212> TYPE: DNA
<213> ORGANISM: Artificial Sequence
<220> FEATURE:
<223> OTHER INFORMATION: DNA Primer

<400> SEQUENCE: 30
ctgagtagat agcagtgaca t                                             21

<210> SEQ ID NO 31
<211> LENGTH: 21
<212> TYPE: DNA
<213> ORGANISM: Artificial Sequence
<220> FEATURE:
<223> OTHER INFORMATION: DNA Primer

<400> SEQUENCE: 31
actgcttatg gttgcagaat c                                             21

<210> SEQ ID NO 32
<211> LENGTH: 20
<212> TYPE: DNA
<213> ORGANISM: Artificial Sequence
<220> FEATURE:
<223> OTHER INFORMATION: DNA Primer

<400> SEQUENCE: 32
gagtatgtaa atgacatctt                                               20

<210> SEQ ID NO 33
<211> LENGTH: 21
<212> TYPE: DNA
<213> ORGANISM: Artificial Sequence
<220> FEATURE:
<223> OTHER INFORMATION: DNA Primer

<400> SEQUENCE: 33
tatgactgca gaagtcaagt c                                             21

<210> SEQ ID NO 34
<211> LENGTH: 21
<212> TYPE: DNA
<213> ORGANISM: Artificial Sequence
<220> FEATURE:
<223> OTHER INFORMATION: DNA Primer

<400> SEQUENCE: 34
tgaccttgaa gaggagatag a                                             21

<210> SEQ ID NO 35
<211> LENGTH: 20
<212> TYPE: DNA
<213> ORGANISM: Artificial Sequence
<220> FEATURE:
<223> OTHER INFORMATION: DNA Primer

<400> SEQUENCE: 35
acaacactct ctcttctcgc                                               20

<210> SEQ ID NO 36
<211> LENGTH: 21
<212> TYPE: DNA
<213> ORGANISM: Artificial Sequence
<220> FEATURE:
<223> OTHER INFORMATION: DNA Primer
```

<400> SEQUENCE: 36
cagattatga gttttggcct g                                              21

<210> SEQ ID NO 37
<211> LENGTH: 21
<212> TYPE: DNA
<213> ORGANISM: Artificial Sequence
<220> FEATURE:
<223> OTHER INFORMATION: DNA Primer

<400> SEQUENCE: 37
atttcactta tataaatatg c                                              21

<210> SEQ ID NO 38
<211> LENGTH: 21
<212> TYPE: DNA
<213> ORGANISM: Artificial Sequence
<220> FEATURE:
<223> OTHER INFORMATION: DNA Primer

<400> SEQUENCE: 38 tctctttat atgctacaat a                                               21

<210> SEQ ID NO 39
<211> LENGTH: 22
<212> TYPE: DNA
<213> ORGANISM: Artificial Sequence
<220> FEATURE:
<223> OTHER INFORMATION: DNA Primer

<400> SEQUENCE: 39
ggtaccatct tccttagaat gg                                             22

<210> SEQ ID NO 40
<211> LENGTH: 22
<212> TYPE: DNA
<213> ORGANISM: Artificial Sequence
<220> FEATURE:
<223> OTHER INFORMATION: DNA Primer

<400> SEQUENCE: 40
tgtgggaaag agacaacaaa cc                                             22

<210> SEQ ID NO 41
<211> LENGTH: 20
<212> TYPE: DNA
<213> ORGANISM: Artificial Sequence
<220> FEATURE:
<223> OTHER INFORMATION: DNA Primer

<400> SEQUENCE: 41
ttcgttggct cccactgctc                                                20

<210> SEQ ID NO 42
<211> LENGTH: 20
<212> TYPE: DNA
<213> ORGANISM: Artificial Sequence
<220> FEATURE:
<223> OTHER INFORMATION: DNA Primer

<400> SEQUENCE: 42
tctggtacac gtcaatgggc                                                20

<210> SEQ ID NO 43
<211> LENGTH: 20

```
<212> TYPE: DNA
<213> ORGANISM: Artificial Sequence
<220> FEATURE:
<223> OTHER INFORMATION: DNA Primer

<400> SEQUENCE: 43
acgaagagat cctgaaggag                                               20

<210> SEQ ID NO 44
<211> LENGTH: 20
<212> TYPE: DNA
<213> ORGANISM: Artificial Sequence
<220> FEATURE:
<223> OTHER INFORMATION: DNA Primer

<400> SEQUENCE: 44
attcccaagg gttggaaggc                                               20

<210> SEQ ID NO 45
<211> LENGTH: 21
<212> TYPE: DNA
<213> ORGANISM: Artificial Sequence
<220> FEATURE:
<223> OTHER INFORMATION: DNA Primer

<400> SEQUENCE: 45
tcaagcattg tttggagatg g                                             21

<210> SEQ ID NO 46
<211> LENGTH: 21
<212> TYPE: DNA
<213> ORGANISM: Artificial Sequence
<220> FEATURE:
<223> OTHER INFORMATION: DNA Primer

<400> SEQUENCE: 46
acagaagcat ttgcagggca g                                             21

<210> SEQ ID NO 47
<211> LENGTH: 20
<212> TYPE: DNA
<213> ORGANISM: Artificial Sequence
<220> FEATURE:
<223> OTHER INFORMATION: DNA Primer

<400> SEQUENCE: 47
accttcgttg gatgcaaggc                                               20

<210> SEQ ID NO 48
<211> LENGTH: 21
<212> TYPE: DNA
<213> ORGANISM: Artificial Sequence
<220> FEATURE:
<223> OTHER INFORMATION: DNA Primer

<400> SEQUENCE: 48
cttggtccaa aattgcgggt c                                             21

<210> SEQ ID NO 49
<211> LENGTH: 22
<212> TYPE: DNA
<213> ORGANISM: Artificial Sequence
<220> FEATURE:
<223> OTHER INFORMATION: DNA Primer

<400> SEQUENCE: 49
```
cgtggcaatt tttcgaaggt ag                                              22

<210> SEQ ID NO 50
<211> LENGTH: 22
<212> TYPE: DNA
<213> ORGANISM: Artificial Sequence
<220> FEATURE:
<223> OTHER INFORMATION: DNA Primer

<400> SEQUENCE: 50
caactcaaaa ccacattgag gc                                              22

<210> SEQ ID NO 51
<211> LENGTH: 22
<212> TYPE: DNA
<213> ORGANISM: Artificial Sequence
<220> FEATURE:
<223> OTHER INFORMATION: DNA Primer

<400> SEQUENCE: 51
agcaacacac gcaaaccaaa tc                                              22

<210> SEQ ID NO 52
<211> LENGTH: 21
<212> TYPE: DNA
<213> ORGANISM: Artificial Sequence
<220> FEATURE:
<223> OTHER INFORMATION: DNA Primer

<400> SEQUENCE: 52
tgcaattcat cctacggtgg c                                               21

<210> SEQ ID NO 53
<211> LENGTH: 21
<212> TYPE: DNA
<213> ORGANISM: Artificial Sequence
<220> FEATURE:
<223> OTHER INFORMATION: DNA Primer

<400> SEQUENCE: 53
tcaggacatg tttgttggtg g                                               21

<210> SEQ ID NO 54
<211> LENGTH: 21
<212> TYPE: DNA
<213> ORGANISM: Artificial Sequence
<220> FEATURE:
<223> OTHER INFORMATION: DNA Primer

<400> SEQUENCE: 54
cacactcagt tcagcttata g                                               21

<210> SEQ ID NO 55
<211> LENGTH: 21
<212> TYPE: DNA
<213> ORGANISM: Artificial Sequence
<220> FEATURE:
<223> OTHER INFORMATION: DNA Primer

<400> SEQUENCE: 55
atacgtgggc ccaactaaga c                                               21

<210> SEQ ID NO 56
<211> LENGTH: 20
<212> TYPE: DNA
<213> ORGANISM: Artificial Sequence
<220> FEATURE:
<223> OTHER INFORMATION: DNA Primer

<400> SEQUENCE: 56
tgtcgtctta ggtgagaggc                                              20

<210> SEQ ID NO 57
<211> LENGTH: 22
<212> TYPE: DNA
<213> ORGANISM: Artificial Sequence
<220> FEATURE:
<223> OTHER INFORMATION: DNA Primer

<400> SEQUENCE: 57
tggctgttcc tagaaggctg tg                                           22

<210> SEQ ID NO 58
<211> LENGTH: 24
<212> TYPE: DNA
<213> ORGANISM: Artificial Sequence
<220> FEATURE:
<223> OTHER INFORMATION: DNA Primer

<400> SEQUENCE: 58
tggagttgga tcggaggatt aagg                                         24

<210> SEQ ID NO 59
<211> LENGTH: 21
<212> TYPE: DNA
<213> ORGANISM: Artificial Sequence
<220> FEATURE:
<223> OTHER INFORMATION: DNA Primer

<400> SEQUENCE: 59
aagggagact ggataaccat c                                            21

<210> SEQ ID NO 60
<211> LENGTH: 21
<212> TYPE: DNA
<213> ORGANISM: Artificial Sequence
<220> FEATURE:
<223> OTHER INFORMATION: DNA Primer

<400> SEQUENCE: 60
ccgctcattt ggtgagtcat g                                            21

<210> SEQ ID NO 61
<211> LENGTH: 21
<212> TYPE: DNA
<213> ORGANISM: Artificial Sequence
<220> FEATURE:
<223> OTHER INFORMATION: DNA Primer

<400> SEQUENCE: 61
atgtgctcgc tgttggtgat g                                            21

<210> SEQ ID NO 62
<211> LENGTH: 23
<212> TYPE: DNA
<213> ORGANISM: Artificial Sequence
<220> FEATURE:
<223> OTHER INFORMATION: DNA Primer

<400> SEQUENCE: 62
gcaccatgga ggtgaaaaaa ata                                          23

<210> SEQ ID NO 63
<211> LENGTH: 20
<212> TYPE: DNA
<213> ORGANISM: Artificial Sequence
<220> FEATURE:
<223> OTHER INFORMATION: DNA Primer

<400> SEQUENCE: 63
ggacggttcg ctggctaaga                                          20

<210> SEQ ID NO 64
<211> LENGTH: 24
<212> TYPE: DNA
<213> ORGANISM: Artificial Sequence
<220> FEATURE:
<223> OTHER INFORMATION: DNA Primer

<400> SEQUENCE: 64
tcactgcctt cctcttcttc ttca                                     24

<210> SEQ ID NO 65
<211> LENGTH: 24
<212> TYPE: DNA
<213> ORGANISM: Artificial Sequence
<220> FEATURE:
<223> OTHER INFORMATION: DNA Primer

<400> SEQUENCE: 65
tccaccgagc aactaccata tctt                                     24

<210> SEQ ID NO 66
<211> LENGTH: 22
<212> TYPE: DNA
<213> ORGANISM: Artificial Sequence
<220> FEATURE:
<223> OTHER INFORMATION: DNA Primer

<400> SEQUENCE: 66
acgagcacat agccaggcat ta                                       22

<210> SEQ ID NO 67
<211> LENGTH: 21
<212> TYPE: DNA
<213> ORGANISM: Artificial Sequence
<220> FEATURE:
<223> OTHER INFORMATION: DNA Primer

<400> SEQUENCE: 67
gcgccttcaa attggcgtct t                                        21

<210> SEQ ID NO 68
<211> LENGTH: 24
<212> TYPE: DNA
<213> ORGANISM: Artificial Sequence
<220> FEATURE:
<223> OTHER INFORMATION: DNA Primer

<400> SEQUENCE: 68
gcgccttaaa taaacccga aact                                      24

<210> SEQ ID NO 69
<211> LENGTH: 23
<212> TYPE: DNA
<213> ORGANISM: Artificial Sequence
<220> FEATURE:
<223> OTHER INFORMATION: DNA Primer

```
<400> SEQUENCE: 69
ttactttggg tcagcattttt ggc                                              23

<210> SEQ ID NO 70
<211> LENGTH: 24
<212> TYPE: DNA
<213> ORGANISM: Artificial Sequence
<220> FEATURE:
<223> OTHER INFORMATION: DNA Primer

<400> SEQUENCE: 70
tattgttgat atattatatt gtcc                                              24

<210> SEQ ID NO 71
<211> LENGTH: 22
<212> TYPE: DNA
<213> ORGANISM: Artificial Sequence
<220> FEATURE:
<223> OTHER INFORMATION: DNA Primer

<400> SEQUENCE: 71 acccttttttg cagtatttat gc                                               22

<210> SEQ ID NO 72
<211> LENGTH: 23
<212> TYPE: DNA
<213> ORGANISM: Artificial Sequence
<220> FEATURE:
<223> OTHER INFORMATION: DNA Primer

<400> SEQUENCE: 72
ctaggtaact cttttagccg tga                                               23

<210> SEQ ID NO 73
<211> LENGTH: 20
<212> TYPE: DNA
<213> ORGANISM: Artificial Sequence
<220> FEATURE:
<223> OTHER INFORMATION: DNA Primer

<400> SEQUENCE: 73
acaacactct ctcttctcgc                                                   20

<210> SEQ ID NO 74
<211> LENGTH: 21
<212> TYPE: DNA
<213> ORGANISM: Artificial Sequence
<220> FEATURE:
<223> OTHER INFORMATION: DNA Primer

<400> SEQUENCE: 74
cagattatga gttttggcct g                                                 21

<210> SEQ ID NO 75
<211> LENGTH: 21
<212> TYPE: DNA
<213> ORGANISM: Artificial Sequence
<220> FEATURE:
<223> OTHER INFORMATION: DNA Primer

<400> SEQUENCE: 75
caggccaaaa ctcataatct g                                                 21

<210> SEQ ID NO 76
```

```
<211> LENGTH: 21
<212> TYPE: DNA
<213> ORGANISM: Artificial Sequence
<220> FEATURE:
<223> OTHER INFORMATION: DNA Primer

<400> SEQUENCE: 76
cagattatga gttttggcct g                                              21

<210> SEQ ID NO 77
<211> LENGTH: 22
<212> TYPE: DNA
<213> ORGANISM: Artificial Sequence
<220> FEATURE:
<223> OTHER INFORMATION: DNA Primer

<400> SEQUENCE: 77
taattttggt tggagaacaa tg                                             22

<210> SEQ ID NO 78
<211> LENGTH: 21
<212> TYPE: DNA
<213> ORGANISM: Artificial Sequence
<220> FEATURE:
<223> OTHER INFORMATION: DNA Primer

<400> SEQUENCE: 78
ctaatccttg tacttcattt c                                              21

<210> SEQ ID NO 79
<211> LENGTH: 21
<212> TYPE: DNA
<213> ORGANISM: Artificial Sequence
<220> FEATURE:
<223> OTHER INFORMATION: DNA Primer

<400> SEQUENCE: 79
atggatccag taagcgtgtg g                                              21

<210> SEQ ID NO 80
<211> LENGTH: 23
<212> TYPE: DNA
<213> ORGANISM: Artificial Sequence
<220> FEATURE:
<223> OTHER INFORMATION: DNA Primer

<400> SEQUENCE: 80
ctaatccttg tacttcattt cag                                            23

<210> SEQ ID NO 81
<211> LENGTH: 23
<212> TYPE: DNA
<213> ORGANISM: Artificial Sequence
<220> FEATURE:
<223> OTHER INFORMATION: DNA Primer

<400> SEQUENCE: 81
gttaaccttc aagtcccaat ctg                                            23

<210> SEQ ID NO 82
<211> LENGTH: 23
<212> TYPE: DNA
<213> ORGANISM: Artificial Sequence
<220> FEATURE:
<223> OTHER INFORMATION: DNA Primer

<400> SEQUENCE: 82
```
agaagaattt ggagcagaaa gtg                                           23

<210> SEQ ID NO 83
<211> LENGTH: 28
<212> TYPE: DNA
<213> ORGANISM: Artificial Sequence
<220> FEATURE:
<223> OTHER INFORMATION: DNA Primer

<400> SEQUENCE: 83
aattgagctc caatggcacc aatgccca                                      28

<210> SEQ ID NO 84
<211> LENGTH: 32
<212> TYPE: DNA
<213> ORGANISM: Artificial Sequence
<220> FEATURE:
<223> OTHER INFORMATION: DNA Primer

<400> SEQUENCE: 84
aattggtacc gaacggtgga atgaatgaa tg                                  32

<210> SEQ ID NO 85
<211> LENGTH: 33
<212> TYPE: DNA
<213> ORGANISM: Artificial Sequence
<220> FEATURE:
<223> OTHER INFORMATION: DNA Primer

<400> SEQUENCE: 85
aaaaaagcag gctatcaatg gcaccaatgc cca                                33

<210> SEQ ID NO 86
<211> LENGTH: 36
<212> TYPE: DNA
<213> ORGANISM: Artificial Sequence
<220> FEATURE:
<223> OTHER INFORMATION: DNA Primer

<400> SEQUENCE: 86
aagaaagctg ggtagaacgg tggaaatgaa tgaatg                             36

<210> SEQ ID NO 87
<211> LENGTH: 29
<212> TYPE: DNA
<213> ORGANISM: Artificial Sequence
<220> FEATURE:
<223> OTHER INFORMATION: DNA Primer

<400> SEQUENCE: 87
ggggacaagt ttgtacaaaa aagcaggct                                     29

<210> SEQ ID NO 88
<211> LENGTH: 29
<212> TYPE: DNA
<213> ORGANISM: Artificial Sequence
<220> FEATURE:
<223> OTHER INFORMATION: DNA Primer

<400> SEQUENCE: 88
ggggaccact ttgtacaaga aagctgggt                                     29

<210> SEQ ID NO 89
<211> LENGTH: 36
<212> TYPE: DNA

```
<213> ORGANISM: Artificial Sequence
<220> FEATURE:
<223> OTHER INFORMATION: DNA Primer

<400> SEQUENCE: 89
aattggcgcg cctgcaggca atggcaccaa tgccca                                36

<210> SEQ ID NO 90
<211> LENGTH: 22
<212> TYPE: DNA
<213> ORGANISM: Artificial Sequence
<220> FEATURE:
<223> OTHER INFORMATION: DNA Primer

<400> SEQUENCE: 90
aattgagctc gattccgcgg ca                                               22

<210> SEQ ID NO 91
<211> LENGTH: 23
<212> TYPE: DNA
<213> ORGANISM: Artificial Sequence
<220> FEATURE:
<223> OTHER INFORMATION: DNA Primer

<400> SEQUENCE: 91
aattgagctc atcgcctccg aga                                              23

<210> SEQ ID NO 92
<211> LENGTH: 36
<212> TYPE: DNA
<213> ORGANISM: Artificial Sequence
<220> FEATURE:
<223> OTHER INFORMATION: DNA Primer

<400> SEQUENCE: 92
aattggtacc tgcaggccag attttatggt gcccaa                                36

<210> SEQ ID NO 93
<211> LENGTH: 35
<212> TYPE: DNA
<213> ORGANISM: Artificial Sequence
<220> FEATURE:
<223> OTHER INFORMATION: DNA Primer

<400> SEQUENCE: 93
aaaaaagcag gctattacgg cggcaatgaa tacat                                 35

<210> SEQ ID NO 94
<211> LENGTH: 35
<212> TYPE: DNA
<213> ORGANISM: Artificial Sequence
<220> FEATURE:
<223> OTHER INFORMATION: DNA Primer

<400> SEQUENCE: 94
aagaaagctg ggtactgaag tctagggctt tttct                                 35

<210> SEQ ID NO 95
<211> LENGTH: 31
<212> TYPE: DNA
<213> ORGANISM: Artificial Sequence
<220> FEATURE:
<223> OTHER INFORMATION: DNA Primer

<400> SEQUENCE: 95
atgcggattc ggcaatgaat acatcgacca g                                     31
```

<210> SEQ ID NO 96
<211> LENGTH: 32
<212> TYPE: DNA
<213> ORGANISM: Artificial Sequence
<220> FEATURE:
<223> OTHER INFORMATION: DNA Primer

<400> SEQUENCE: 96
ttgggtacct gtctagggct ttttcttcca ag                         32

<210> SEQ ID NO 97
<211> LENGTH: 24
<212> TYPE: DNA
<213> ORGANISM: Artificial Sequence
<220> FEATURE:
<223> OTHER INFORMATION: DNA Primer

<400> SEQUENCE: 97
tgaaaaagac tttgagcaga ttgg                                  24

<210> SEQ ID NO 98
<211> LENGTH: 20
<212> TYPE: DNA
<213> ORGANISM: Artificial Sequence
<220> FEATURE:
<223> OTHER INFORMATION: DNA Primer

<400> SEQUENCE: 98
ttgccatgct ccttctggat                                       20

<210> SEQ ID NO 99
<211> LENGTH: 40
<212> TYPE: PRT
<213> ORGANISM: Glycine max

<400> SEQUENCE: 99

Cys Arg Gly Ile Glu Leu Ile Ala Ser Glu Asn Phe Thr Ser Phe Ala
1               5                   10                  15

Val Ile Glu Ala Leu Gly Ser Ala Leu Thr Asn Lys Tyr Ser Glu Gly
            20                  25                  30

Met Pro Gly Asn Arg Tyr Tyr Gly
        35                  40

<210> SEQ ID NO 100
<211> LENGTH: 50
<212> TYPE: PRT
<213> ORGANISM: Glycine max

<400> SEQUENCE: 100

His Leu Asp Ala Gln Ser Trp Gly Val Asn Val Gln Pro Tyr Ser Gly
1               5                   10                  15

Ser Pro Ala Asn Phe Ala Ala Tyr Thr Ala Val Leu Asn Pro His Asp
            20                  25                  30

Arg Ile Met Gly Leu Asp Leu Arg Ser Gly Gly His Leu Thr His Gly
        35                  40                  45

Tyr Tyr
    50

<210> SEQ ID NO 101
<211> LENGTH: 20
<212> TYPE: PRT
<213> ORGANISM: Glycine max

<400> SEQUENCE: 101

Arg Pro Leu Gly Leu Thr Gly Tyr Lys Val Glu Lys Leu Cys Asp Leu
1               5                   10                  15

Cys Asn Ile Thr
            20

<210> SEQ ID NO 102
<211> LENGTH: 40
<212> TYPE: PRT
<213> ORGANISM: Glycine max

<400> SEQUENCE: 102

Cys Arg Gly Ile Glu Leu Ile Ala Ser Glu Asn Phe Thr Ser Phe Ala
1               5                   10                  15

Val Ile Glu Ala Leu Gly Ser Ala Leu Thr Asn Lys Tyr Ser Glu Gly
            20                  25                  30

Met Pro Gly Asn Arg Tyr Tyr Gly
        35                  40

<210> SEQ ID NO 103
<211> LENGTH: 50
<212> TYPE: PRT
<213> ORGANISM: Glycine max

<400> SEQUENCE: 103

His Leu Asp Ala Gln Ser Trp Gly Val Asn Val Gln Pro Tyr Ser Gly
1               5                   10                  15

Ser Pro Ala Asn Phe Ala Ala Tyr Thr Ala Val Leu Asn Pro His Asp
            20                  25                  30

Arg Ile Met Gly Leu Asp Leu Arg Ser Gly Gly His Leu Thr His Gly
        35                  40                  45

Tyr Tyr
    50

<210> SEQ ID NO 104
<211> LENGTH: 20
<212> TYPE: PRT
<213> ORGANISM: Glycine max

<400> SEQUENCE: 104

Arg Pro Leu Gly Leu Thr Gly Tyr Lys Val Glu Lys Leu Cys Asp Leu
1               5                   10                  15

Cys Asn Ile Thr
            20

<210> SEQ ID NO 105
<211> LENGTH: 471
<212> TYPE: PRT
<213> ORGANISM: Glycine max

<400> SEQUENCE: 105

Met Asp Pro Val Ser Val Trp Gly Asn Thr Pro Leu Ala Thr Val Asp
1               5                   10                  15

Pro Glu Ile His Asp Leu Ile Glu Lys Glu Lys Arg Arg Gln Cys Arg
            20                  25                  30

Gly Ile Glu Leu Ile Ala Ser Glu Asn Phe Thr Ser Phe Ala Val Ile
        35                  40                  45

Glu Ala Leu Gly Ser Ala Leu Thr Asn Lys Tyr Ser Lys Gly Met Pro
    50                  55                  60

```
Gly Asn Arg Tyr Tyr Gly Asn Glu Tyr Ile Asp Gln Ile Glu Asn
 65                  70                  75                  80

Leu Cys Arg Ser Arg Ala Leu Gln Ala Phe His Leu Asp Ala Gln Ser
                 85                  90                  95

Trp Gly Val Asn Val Gln Pro Tyr Ser Gly Ser Pro Ala Asn Phe Ala
                100                 105                 110

Ala Tyr Thr Ala Val Leu Asn Pro His Asp Arg Ile Met Gly Leu Asp
            115                 120                 125

Leu Arg Ser Gly Gly His Leu Thr His Gly Tyr Tyr Thr Ser Gly Gly
        130                 135                 140

Lys Lys Ile Ser Ala Thr Ser Ile Tyr Phe Glu Ser Leu Pro Tyr Lys
145                 150                 155                 160

Val Asn Ser Thr Thr Gly Tyr Ile Asp Tyr Asp Arg Leu Glu Glu Lys
                165                 170                 175

Ala Leu Asp Phe Arg Pro Lys Leu Ile Ile Cys Gly Gly Ser Ala Tyr
            180                 185                 190

Pro Arg Asp Trp Asp Tyr Lys Arg Phe Arg Glu Val Ala Asp Lys Cys
        195                 200                 205

Gly Ala Leu Leu Leu Cys Asp Met Ala His Thr Ser Gly Leu Val Ala
210                 215                 220

Ala Gln Glu Val Asn Ser Pro Phe Glu Tyr Cys Asp Ile Val Thr Thr
225                 230                 235                 240

Thr Thr His Lys Ser Leu Arg Gly Pro Arg Ala Gly Met Ile Phe Tyr
                245                 250                 255

Arg Lys Gly Pro Lys Pro Pro Lys Gly Gln Pro Glu Asn Ala Val
                260                 265                 270

Tyr Asp Phe Glu Asp Lys Ile Asn Phe Ala Val Phe Pro Ser Leu Gln
            275                 280                 285

Gly Gly Pro His Asn His Gln Ile Gly Ala Leu Ala Val Ala Leu Lys
        290                 295                 300

Gln Ala Ala Ser Pro Gly Phe Lys Ala Tyr Ala Lys Gln Val Lys Ala
305                 310                 315                 320

Asn Ala Val Ala Leu Gly Lys Tyr Leu Met Gly Lys Gly Tyr Ser Leu
                325                 330                 335

Val Thr Gly Gly Thr Glu Asn His Leu Val Leu Trp Asp Leu Arg Pro
            340                 345                 350

Leu Gly Leu Thr Gly Tyr Lys Val Glu Lys Leu Cys Asp Leu Cys Asn
        355                 360                 365

Ile Thr Val Asn Lys Asn Ala Val Phe Gly Asp Ser Ser Ala Leu Ala
        370                 375                 380

Pro Gly Gly Val Arg Ile Gly Ala Pro Ala Met Thr Ser Arg Gly Leu
385                 390                 395                 400

Val Glu Lys Asp Phe Glu Gln Ile Gly Glu Phe Leu His Arg Ala Val
                405                 410                 415

Thr Leu Thr Leu Glu Ile Gln Lys Glu His Gly Lys Leu Leu Lys Asp
                420                 425                 430

Phe Asn Lys Gly Leu Val Asn Asn Lys Ala Ile Glu Asp Leu Lys Ala
            435                 440                 445

Asp Val Glu Lys Phe Ser Ala Leu Phe Asp Met Pro Gly Phe Leu Val
        450                 455                 460

Ser Glu Met Lys Tyr Lys Asp
465                 470
```

<210> SEQ ID NO 106
<211> LENGTH: 471
<212> TYPE: PRT
<213> ORGANISM: Glycine max

<400> SEQUENCE: 106

```
Met Asp Pro Val Ser Val Trp Gly Asn Thr Pro Leu Ala Thr Val Asp
1               5                   10                  15

Pro Glu Ile His Asp Leu Ile Glu Lys Glu Lys Arg Arg Gln Cys Arg
            20                  25                  30

Gly Ile Glu Leu Ile Ala Ser Glu Asn Phe Thr Ser Phe Ala Val Ile
        35                  40                  45

Glu Ala Leu Gly Ser Ala Leu Thr Asn Lys Tyr Ser Glu Gly Met Pro
    50                  55                  60

Gly Asn Arg Tyr Tyr Gly Gly Asn Glu Tyr Ile Asp Gln Ile Glu Asn
65                  70                  75                  80

Leu Cys Arg Ser Arg Ala Leu Gln Ala Phe His Leu Asp Ala Gln Ser
                85                  90                  95

Trp Gly Val Asn Val Gln Pro Tyr Ser Gly Ser Pro Ala Asn Phe Ala
            100                 105                 110

Ala Tyr Thr Ala Val Leu Asn Pro His Asp Arg Ile Ile Gly Leu Asp
        115                 120                 125

Leu Arg Ser Gly Gly His Leu Thr His Gly Tyr Tyr Thr Ser Gly Gly
    130                 135                 140

Lys Lys Ile Ser Ala Thr Ser Ile Tyr Phe Glu Ser Leu Pro Tyr Lys
145                 150                 155                 160

Val Asn Ser Thr Thr Gly Tyr Ile Asp Tyr Asp Arg Leu Glu Glu Lys
                165                 170                 175

Ala Leu Asp Phe Arg Pro Lys Leu Ile Ile Cys Gly Gly Ser Ala Tyr
            180                 185                 190

Pro Arg Asp Trp Asp Tyr Lys Arg Phe Arg Glu Val Ala Asp Lys Cys
        195                 200                 205

Gly Ala Leu Leu Leu Cys Asp Met Ala His Thr Ser Gly Leu Val Ala
    210                 215                 220

Ala Gln Glu Val Asn Ser Pro Phe Glu Tyr Cys Asp Ile Val Thr Thr
225                 230                 235                 240

Thr Thr His Lys Ser Leu Arg Gly Pro Arg Ala Gly Met Ile Phe Tyr
                245                 250                 255

Arg Lys Gly Pro Lys Pro Pro Lys Lys Gly Gln Pro Glu Asn Ala Val
            260                 265                 270

Tyr Asp Phe Glu Asp Lys Ile Asn Phe Ala Val Phe Pro Ser Leu Gln
        275                 280                 285

Gly Gly Pro His Asn His Gln Ile Gly Ala Leu Ala Val Ala Leu Lys
    290                 295                 300

Gln Ala Ala Ser Pro Gly Phe Lys Ala Tyr Ala Lys Gln Val Lys Ala
305                 310                 315                 320

Asn Ala Val Ala Leu Gly Lys Tyr Leu Met Gly Lys Gly Tyr Ser Leu
                325                 330                 335

Val Thr Gly Gly Thr Glu Asn His Leu Val Leu Trp Asp Leu Arg Pro
            340                 345                 350

Leu Gly Leu Thr Gly Tyr Lys Val Glu Lys Leu Cys Asp Leu Cys Asn
        355                 360                 365

Ile Thr Val Asn Lys Asn Ala Val Phe Gly Asp Ser Ser Ala Leu Ala
    370                 375                 380
```

```
Pro Gly Gly Val Arg Ile Gly Ala Pro Ala Met Thr Ser Arg Gly Leu
385                 390                 395                 400

Val Glu Lys Asp Phe Glu Gln Ile Gly Glu Phe Leu His Arg Ala Val
                405                 410                 415

Thr Leu Thr Leu Glu Ile Gln Lys Glu His Gly Lys Leu Leu Lys Asp
            420                 425                 430

Phe Asn Lys Gly Leu Val Asn Asn Lys Ala Ile Glu Asp Leu Lys Ala
            435                 440                 445

Asp Val Glu Lys Phe Ser Ala Leu Phe Asp Met Pro Gly Phe Leu Val
        450                 455                 460

Ser Glu Met Lys Tyr Lys Asp
465             470

<210> SEQ ID NO 107
<211> LENGTH: 40
<212> TYPE: PRT
<213> ORGANISM: Glycine max

<400> SEQUENCE: 107

Cys Arg Gly Ile Glu Leu Ile Ala Ser Glu Asn Phe Thr Ser Phe Ala
1               5                   10                  15

Val Ile Glu Ala Leu Gly Ser Ala Leu Thr Asn Lys Tyr Ser Glu Gly
            20                  25                  30

Met Pro Gly Asn Arg Tyr Tyr Gly
            35                  40

<210> SEQ ID NO 108
<211> LENGTH: 50
<212> TYPE: PRT
<213> ORGANISM: Glycine max

<400> SEQUENCE: 108

His Leu Asp Ala Gln Ser Trp Gly Val Asn Val Gln Pro Tyr Ser Gly
1               5                   10                  15

Ser Pro Ala Asn Phe Ala Ala Tyr Thr Ala Val Leu Asn Pro His Asp
            20                  25                  30

Arg Ile Met Gly Leu Asp Leu Pro Ser Gly Gly His Leu Thr His Gly
            35                  40                  45

Tyr Tyr
    50

<210> SEQ ID NO 109
<211> LENGTH: 20
<212> TYPE: PRT
<213> ORGANISM: Glycine max

<400> SEQUENCE: 109

Arg Pro Leu Gly Leu Thr Gly Asn Lys Val Glu Lys Leu Cys Asp Leu
1               5                   10                  15

Cys Asn Ile Thr
            20

<210> SEQ ID NO 110
<211> LENGTH: 60
<212> TYPE: DNA
<213> ORGANISM: Glycine max

<400> SEQUENCE: 110
cccaaagtgt tgtcagtgtt cgagaaccgt gggagaaagc tacacaccac tcgatcatgg    60
```

```
<210> SEQ ID NO 111
<211> LENGTH: 60
<212> TYPE: DNA
<213> ORGANISM: Glycine max

<400> SEQUENCE: 111
cttggtaacg atattacctt caaggggaa agcttatcag ctacaaaatt ggcacacaag    60

<210> SEQ ID NO 112
<211> LENGTH: 60
<212> TYPE: DNA
<213> ORGANISM: Glycine max

<400> SEQUENCE: 112
tataaatgcc gcaagaaatt tagtctcctc aacctgaact atccctcaat cacagtccca    60

<210> SEQ ID NO 113
<211> LENGTH: 60
<212> TYPE: DNA
<213> ORGANISM: Glycine max

<400> SEQUENCE: 113
tacattgctc atgttcagaa cccgtatgga atcaccgttt ctgtgaagcc aagcatcttg    60

<210> SEQ ID NO 114
<211> LENGTH: 60
<212> TYPE: DNA
<213> ORGANISM: Glycine max

<400> SEQUENCE: 114
cccaaagtgt tgtcagcgtt cgagaaccgt gggagaaagc tacacaccac tcgatcatgg    60

<210> SEQ ID NO 115
<211> LENGTH: 60
<212> TYPE: DNA
<213> ORGANISM: Glycine max

<400> SEQUENCE: 115
cttggtaacg atattacctt caaggggaa agcttatcag ctacaaaatt ggcacacaag    60

<210> SEQ ID NO 116
<211> LENGTH: 60
<212> TYPE: DNA
<213> ORGANISM: Glycine max

<400> SEQUENCE: 116
tataaatgcc gcaagaaatt tagtctcctc aacctgaact atccctaat cacagtccca    60

<210> SEQ ID NO 117
<211> LENGTH: 60
<212> TYPE: DNA
<213> ORGANISM: Glycine max

<400> SEQUENCE: 117
tacattgctc atgttcaaaa cccgtatgga atcaccgttt ctgtgaagcc aagcatcttg    60

<210> SEQ ID NO 118
<211> LENGTH: 60
<212> TYPE: DNA
<213> ORGANISM: Glycine max

<400> SEQUENCE: 118
```
cccaaagtgt tgtcagtgtt cgagaaccgt gggagaaagc tacacaccac tcgatcatgg    60

<210> SEQ ID NO 119
<211> LENGTH: 60
<212> TYPE: DNA
<213> ORGANISM: Glycine max

<400> SEQUENCE: 119
cttggtaacg atattacctt gaagggggaa agcttatcag ctacaaaatt ggcacacaag    60

<210> SEQ ID NO 120
<211> LENGTH: 60
<212> TYPE: DNA
<213> ORGANISM: Glycine max

<400> SEQUENCE: 120
tataaatgcc gcaagaaatt tagtctcctc aacctgaact atccctcaat cacagtccca    60

<210> SEQ ID NO 121
<211> LENGTH: 60
<212> TYPE: DNA
<213> ORGANISM: Glycine max

<400> SEQUENCE: 121
tacattgctc atgttcaaaa cccgtatgga atcaccgttt ctgtgaagcc aagcatcttg    60

<210> SEQ ID NO 122
<211> LENGTH: 2339
<212> TYPE: DNA
<213> ORGANISM: Glycine max

<400> SEQUENCE: 122
caatggcacc aatgcccaat gggagattta agtcaagccc aacatcaacc tctgaaatta    60
tgaattatga aattaaaatg cttcctagta agtgaactag ttgcatctca tttatatcat   120
aaatttcgaa ctcgactttt cttggccatg ttagtaaagt ttgggggatt gttcaaaatt   180
ggtggagtgg ttcagcttaa tctccaaatt atttgttcta agttgttttg gtaggcaggt   240
ttaatttttt cctgatcctg ggaaaaaaat tattgatacc atattaacat ctcttgacga   300
tgctacgaga tttctcatga ttatagaact gagtagggtg gcttaaaagg ttttatttta   360
aatataattt caccacattg aattgggtat tagtaaactg gttactggta tgcctgtaaa   420
gtggacaatg ataaatgttt ttatagaagt tggtatggat tttaaaatag ctcatgtata   480
aaatgtgaaa aaggaaacgt gaactaaaat gctaataata aaagataaag actaaattaa   540
ttaaagttaa aggataaaat gcttgttaca tcaagtcatt ttaaaggtgc actattagag   600
gctgcacagt aaaagttaac actgatatat ttttaaagat gttcttagtt aaatagcttt   660
tgacttgatg gggtgaagac acaagaggtt gttgttgcga tgtgattttg gctgaatatg   720
catgcctgct gaacattgac ttcattgtta aatcaaaatt aatccccatag acctattgta   780
ttatttaagg ggatcaattt cataaatcaa aatttattgg ttggggaaaa aaacaatgtt   840
tagtagttcc cagtcatatt cagaaaccta caaattaact atcccccatg ttaatgaagc   900
aaggtgtggg ggaaggaaag agtcagcatc agtgaagtag agaggggggt tggtgatttt   960
ggtgggaata aattggctat attgccccca ccaacctcgt tgctaccaaa taccaacaac  1020
actgactcac tgagaattgg gaaagaaact taaaaccaag tcttgcagtg acgtacatgt  1080
agtgtgtgca tcacacattc aggtttccag tcaaattgta gaacaaatga atttcttgct  1140
ttaacttaag ttgaagttta agaagtgaag ctgatgcttg ttttttgaatg aaaagccttt  1200

```
gatagtttga tgtaagcatt ttccaaattt aactcttccc atgcttgaca gagccaatta    1260
agctaactgg tttgataaca agtaaacttc taaatctatg agtatgagtg catgcagcac    1320
accttttaaa cacaagccac tgttttgtct tttttatcaa cagaaagaga atcctactaa    1380
taacactaat caagatcgct gctcttttct gtttattttt cttaataaat taacttttgt    1440
tttgtactcc tgttaaacaa ctgctctatt tgtttcatgt gttgcattaa ataacatggt    1500
tttattcaca tctacaagca aaatttccta aaaactgtga atgatgtaga agcaagtcat    1560
ttatgttttg aaattcacgc attggagttt ctaacgccca accaaccaaa cggtaatatg    1620
aatatcgtgt ttggaacaaa ttagaattta ggacataatt tttcacatca gaataaatgt    1680
taggaatttt tgcttttacg ttttttcgcat taaaataatg tgatttatcg gttgttcctg    1740
aacaataacc atcgatgtaa ttataaaatt ctaatttgtc ctatcctggg gcgtcaacgt    1800
ccagccaaat gcgtaacatt tattctgatg taaaaaatta ttattattat tatagataat    1860
aaaatcttgt tcctgaacaa taaccatcaa tgtaattata aaattgaatc ttagactcaa    1920
aactagttat taatctggaa caatgtttac tcaaaactag ttattaatag tattttttaag   1980 ttaatttgaa attttttttt cggcgttaaa caaatactag atgtttatac tacaaatatt    2040
gattattgat tataaattta taaatgttaa aaaaaaaaaa agagaaaaca aagaattgaa    2100
gttgtggttg gtagtaaacc agcaccaggc gaacaagtgg acacaattta cctacaagta    2160
actaaccaac cggaagcaca ggctacaacg gtcctttcac acccggtctc aaagctttta    2220
aaaacgaaca catacgcact catatttcca ttccacctca acaaacacaa caacactctc    2280
tcttctcgct cttggctttt cgctcttcac tcactctcat tcattcattt ccaccgttc     2339
```

<210> SEQ ID NO 123
<211> LENGTH: 2340
<212> TYPE: DNA
<213> ORGANISM: Glycine max

<400> SEQUENCE: 123

```
caatggcacc aatgcccaat gggagattta agtcaagccc aacatcaacc tctgaaatta     60
tgaattatga aattaaaatg cttcctagta agtgaactag ttgcatctca tttatatcat    120
aaatttcgaa ctacgacttt cttggccatg ttagtaaagt ttgggggatt gttcaaaatt    180
ggtggagtgg ttcagcttaa tctccaaatt atttgttcta agttgttttg gtaggcaggt    240 ttaattttttt cctgatcctg ggaaaaaaat tattgatacc atattaacat ctcttgacga    300
tgctacgaga tttctcatga ttatagaact gagtaggggtg gcttaaaagg ttttatttta    360
aatataattt caccacattg aattgggtat tagtaaactg gttactggta tgcctgtaaa    420
gtggacaatg ataaatgttt ttatagaagt tggtatggat tttaaaatag ctcatgtata    480
aaatgtgaaa aaggaaacgt gaactaaaat gctaataata aaagataaag actaaattaa    540
ttaaagttaa aggataaaat gcttgttaca tcaagtcatt ttaaaggtgc actattagag    600
gctgcacagt aaaagttaac actgatatat ttttaaagat gttcttagtt aaatagcttt    660
tgacttgatg gggtgaagac acaagaggtt gttgttgcga tgtgattttg gctgaatatg    720
catgcctgct gaacattgac ttcattgtta atcaaaatt aatcccatag acctattgta    780
ttatttaagg ggatcaattt cataaatcaa aatttattgg ttggggaaaa aaacaatgtt    840
tagtagttcc cagtcatatt cagaaaccta caaattaact atcccccatg ttaatgaagc    900
aaggtgtggg ggaaggaaag agtcagcatc agtgaagtag agagggggt tggtgatttt    960
```

-continued

```
ggtgggaata aattggctat attgccccca ccaacctcgt tgctaccaaa taccaacaac    1020
actgactcac tgagaattgg gaaagaaact taaaaccaag tcttgcagtg acgtacatgc    1080
agtgtgtgca tcacacattc aggtttccag tcaaattgta gaacaaatga atttcttgct    1140
ttaacttaag ttgaagttta agaagtgaag ctgatgcttg tttttgaatg aaaagccttt    1200
gatagtttga tgtaagcatt ttccaaattt aactcttccc atgcttgaca gagccaatta    1260
agctaactgg tttgataaca agtaaacttc taaatctatg agtatgagtg catgcagcac    1320
accttttaaa cacaagccac tgttttgtct tttttatcaa cagaaagaga atcctactaa    1380
taacactaat caagatcgct gctcttttct gtttatttt  cttaataaat taacttttgt    1440
tttgtactcc tgttaaacaa ctgctctatt tgtttcatgt gttgcattaa ataacatggt    1500
tttattcaca tctacaagca aaatttccta aaaactgtga atgatgtaga agcaagtcat    1560
ttatgttttg aaattcacgc attggagttt ctaacgccca accaaccaaa cggtaatatg    1620
aatatcgtgt ttggaacaaa ttagaattta ggacataatt tttcacatca gaataaatgt    1680
taggaatttt tgcttttacg tttttcgcat taaaataatg tgatttatcg gttgttcctg    1740
aacaataacc atcgatgtaa ttataaaatt ctaatttgtc ctatcctggg gcgtcaacgt    1800
ccagccaaat gcgtaacatt tattctgatg taaaaaatta ttattattat tatagataat    1860
aaaatcttgt tcctgaacaa taaccatcaa tgtaattata aaattgaatc ttagactcaa    1920
aactagttat taatctggaa caatgtttac tcaaaactag ttattaatag tattttttaag 1980 ttaatttgaa atttttttt  cggcgttaaa caaatactag atgtttatac tacaaatatt    2040
gattattgat tataaattta taaatgttaa aaaaaaaaaa aagagaaaac aaagaattga    2100
agttgtggtt ggtagtaaac cagcaccagg cgaacaagtg gacacaattt acctacaagt    2160
aactaaccaa ccggaagcac aggctacaac ggtcctttca cacccggtct caaagctttt    2220
aaaaacgaac acatacgcac tcacatttcc attccacctc aacaaacaca acaacactct    2280
ctcttctcgc tcttggcttt tcgctcttca ctcactctca ttcattcatt tccaccgttc    2340
```